United States Patent
Giesen et al.

(10) Patent No.: US 7,465,471 B2
(45) Date of Patent: Dec. 16, 2008

(54) PALATABILITY OF AQUACULTURE FEED

(75) Inventors: Andrew F. Giesen, Defiance, MO (US); Mercedes Vazquez-Anon, Chesterfield, MO (US)

(73) Assignee: Novus International, Inc., St. Louis, MO (US)

(*) Notice: Subject to any disclaimer, the term of this patent is extended or adjusted under 35 U.S.C. 154(b) by 683 days.

(21) Appl. No.: 11/078,093

(22) Filed: Mar. 11, 2005

(65) Prior Publication Data
US 2005/0215623 A1 Sep. 29, 2005

Related U.S. Application Data

(63) Continuation-in-part of application No. 10/652,745, filed on Aug. 29, 2003.

(60) Provisional application No. 60/465,549, filed on Apr. 25, 2003, provisional application No. 60/456,673, filed on Mar. 21, 2003, provisional application No. 60/456,732, filed on Mar. 21, 2003.

(51) Int. Cl.
*A23J 1/00* (2006.01)
(52) U.S. Cl. .................. 426/656; 426/805; 426/807
(58) Field of Classification Search ............ 426/656, 426/805, 807
See application file for complete search history.

(56) References Cited

U.S. PATENT DOCUMENTS

| | | | |
|---|---|---|---|
| 2,707,682 A * | 5/1955 | Arkens | 426/319 |
| 2,938,053 A | 5/1960 | Blake et al. | |
| 3,284,212 A * | 11/1966 | Tribble et al. | 426/64 |
| 4,762,854 A | 8/1988 | Lloyd et al. | |
| 5,591,467 A | 1/1997 | Bland et al. | |
| 5,795,602 A | 8/1998 | Craig et al. | |
| 5,928,689 A | 7/1999 | Milkowski et al. | |
| 5,985,336 A | 11/1999 | Ivey et al. | |
| 6,008,409 A | 12/1999 | Hasseberg et al. | |
| 6,355,289 B1 | 3/2002 | Rolow et al. | |
| 2002/0172737 A1 | 11/2002 | Pinski et al. | |
| 2003/0077254 A1 | 4/2003 | Ramaekers | |

FOREIGN PATENT DOCUMENTS

| | | |
|---|---|---|
| CA | 1261855 | 9/1989 |
| EP | 0 937 706 A1 | 8/1999 |
| EP | 1 062 879 A1 | 12/2000 |
| EP | 1 205 115 A2 | 5/2002 |
| FR | 2795919 A1 | 1/2001 |
| JP | 08 107757 A1 | 4/1996 |
| JP | 10 327751 A1 | 12/1998 |
| JP | 03 107789 B | 11/2000 |
| JP | 03 270588 B | 4/2002 |
| WO | WO 96/35337 A1 | 11/1996 |
| WO | WO 99/04646 A1 | 2/1999 |
| WO | WO 00/59877 A1 | 10/2000 |
| WO | WO 03/037103 A1 | 5/2003 |
| WO | WO 03/084346 A1 | 10/2003 |

OTHER PUBLICATIONS

Tacon, "The Nutrition and Feeding of Farmed Fish and Shrimp—A Training Manual 3. Feeding Methods" 25 pages, downloaded from http://www.fao.org/documents, 1987.*

Doerr, J.A., et al., Possible Anti-Fungal Effects Of Hydroxy-Methylthio-Butanoic Acid (HMB), Poultry Science, 1995, vol. 74(1), p. 23, Abstracts of Papers.

Anderson, David B., et al., "Gut microbiology and growth-promoting antibiotics in swine", *Pig News and Information*, 1999, pp. 115N-122N, Vol. 20, No. 4, CABI Publishing, Farnham Royal, England.

BASF Fine Chemicals, "Effect of Luprosil® NC applications to litter on the health and performance of turkeys", 1990, BASF Technical Bulletin KC 9037.

Bedford, Michael, "Removal of antibiotic growth promoters from poultry diets: implications and strategies to minimise subsequent problems", *World's Poultry Science Journal*. Dec. 2000, pp. 347-365, vol. 56.

Bolduan, Von G., et al., "Die wirkung von Propion-und Ameisensaure in der Ferkelaufzucht", *J. Anim. Physiol. a. Anim. Nutr.*, 1988, pp. 72-78, vol. 59.

Bone, Elizabeth, et al., "The production of urinary phenols by gut bacteria and their possible role in the causation of large bowel cancer", *The American Journal of Clinical Nutrition*, Dec. 1976, pp. 1448-1454, vol. 29, No. 12.

Botermans, J.A.M., et al., "The exocrine pancreas in pig growth and performance", Biology of the Pancreas in Growing Animals, 1999, pp. 395-408, Elsevier Science.

Brachet, Patrick, et al., "Transport of Methionine Hydroxy Analog across the Brush Border Membrane of Rat Jejunum", *The Journal of Nutrition*, 1987, pp. 1241-1246, vol. 117, Wistar Institute of Anatomy and Biology, Philadelphia.

(Continued)

*Primary Examiner*—C. Sayala
(74) *Attorney, Agent, or Firm*—Polsinelli Shalton Flanigan Suelthaus PC

(57) ABSTRACT

A method for enhancing the palatability of aquaculture food, the method comprising treating the food with a compound of Formula I:

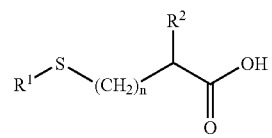

wherein $R^1$, $R^2$, $R^3$, and n are as defined herein, are disclosed.

11 Claims, 19 Drawing Sheets

OTHER PUBLICATIONS

Burns et al. "Sulfur Amino Acid Requirements of Immature Beagle Dogs" Journal of Nutrition, vol. 111, No. 12 (1981) pp. 2117-2124.
Cha, Yong-Jun, et al., "Identification of Aroma-Active Compounds in Korean Salt-Fermented Fishes by Aroma Extract Dilution Analysis 1. Aroma-Active Components in Salt-Fermented Anchovy on the Market," Korean Society of Food Science and Nutrition, 1999, pp. 312-318, vol. 28, No. 2, Abstract only.
Chaveerach, P., et al., "In Vitro Study on the Effect of Organic Acids on *Campylobacter jejuni/coli* Populations in Mixtures of Water and Feed", *Poultry Science*, May 2002, pp. 621-628, vol. 81, No. 5.
Cherrington, C.A., et al., "Organic Acids: Chemistry, Antibacterial Activity and Practical Applications", *Advances in Microbial Physiology*, 1991, pp. 87-108, vol. 32.
Coates, M.E., et al., "The Effect of Antibiotics on the Intestine of the Chick", *The British Journal of Nutrition*, 1955, pp. 110-119, vol. 9, No. 1, Cambridge University Press, Cambridge, England.
Cole, D.J.A., et al., "The Effect on Performance and Bacterial Flora of Lactic acid, Propionic acid, Calcium propionate and Calcium acrylate in the Drinking Water of Weaned Pigs", *The Veterinary Record*, Nov. 2, 1968, pp. 459-464, vol. 83, British Veterinary Association, London.
Corthier, G., et al., "Interrelationships between Digestive Proteolytic Activities and Production and Quantitation of Toxins in Pseudomembranous Colitis Induced by *Clostridium difficile* in Gnotobiotic Mice", *Infection and Immunity*, Dec. 1989, pp. 3922-3927, vol. 57, No. 12, American Society for Microbiology, Washington.
Cranwell, P.D., "Development of the Neonatal Gut and Enzyme Systems", The Neonatal Pig—Development and Survival, 1995, pp. 99-154, M.A. Varley, CAB International, Oxon.
Dierick, N.A., et al., "Influence of the gut flora and of some growth promoting feed additives on nitrogen metabolism in pigs, I. Studies in virto", *Livestock Production Science*, 1986, pp. 161-176, vol. 14, Elsevier Science Publishers, Amsterdam.
Dierick, N.A., et al., " Influence of the gut flora and of some growth promoting feed additives on nitrogen metabolism in pigs. II. Studies in vivo", *Livestock Production Science*, 1986, pp. 177-193, vol. 14, Elsevier Science Publishers, Amsterdam.
Dunnington, E.A., et al. "Enzyme Activity and Organ Development in Newly Hatched Chicks Selected for High or Low Eight-Week Body Weight", *Poultry Science*, 1995, pp. 761-770, vol. 74, No. 5.
Eckel, Von B., et al., "Zum Einfluβ von Ameisensaure auf die Konzentrationen an Ammoniak und biogenen Aminen im Gastrointestinaltrakt", *J. Anim. Physiol. a. Anim. Nutr.*, 1992, pp. 198-205, vol. 67.
Eidelsburger, U., et al., "Zum Einfluβ von Fumarsäure, Salzsäure, Natriumformiate, Tylosin und Toyocerin auf tägliche Zunahmen, Futteraufnagme, Futterverwertung und Verdaulichkeit", *J. Anim. Physiol. a. Anim. Nutr.*, 1992, pp. 82-92, vol. 68.
Eidelsburger, Von U., et al., "Zum Elnfluβ von Amelsensäure, Calciumformiat und Natriumhydrogencarbonat auf pH-Wert, Trockenmassegehalt, Konzentration an Carbonsäuren und Ammoniak in verschledenen Segmenten des Gastrointestinaltraktes", *J. Anim. Physiol. A. Anim. Nutr.*, 1992, pp. 20-32, vol. 68.
Engelhardt, W. Von, et al., "Absorption of Short-chain fatty Acids and Their Role in the Hindgut of Monogastric Animals", *Animal Feed Science and Technology*, 1989, pp. 43-53, vol. 23, Elsevier Science Publishers, Amsterdam.
Enthoven, P., et al., "Antibacterial properties of 2-hydroxy-4-(methylthio)butyric Acid (HMB, alimet)", Eur. Assoc. Anim. Prod. Proc., 2002, EEAP, Cairo.
Franti, C.E., et al., "Antibiotic Growth Promotion: Effects of Zinc Bacitracin and Oxytetracycline on the Digestive, Circulatory, and Excretory Systems of New Hampshire Cockerels", *Poultry Science*, 1972, pp. 1137-1145, vol. 51, No. 4.
Gabert, V.M, et al., "The effect of fumaric acid and sodium fumarate supplementation to diets for weanling pigs on amino acid digestibility and volatile fatty acid concentrations in ileal digesta", *Animal Feed Science and Technology*, 1995, pp. 243-254, vol. 53, Elsevier Science.

Gedek, Von Brigitte, et al., "Zum Einfluβ von Fumarsäure, Salzsäure, Natriumformiat, Tylosin und Toyocerin auf die Keimzahien der Mikroflora und deren Zusammensetzung in verschiedenen Segmenten des Gastrointestinaltraktes", *J. Anim. Physiol. a, Anim. Nutr.*, 1992, pp. 209-217, vol. 68.
Hadorn, R., et al., "Effect of different dosages of an organic-acid mixture in broiler diets", Archiv fuer Gefluegelkunde, 2001, pp. 22-27, vol. 65.
Harada, Etsumori, et al., "Effect of short-chain fatty acids on the secretory response of the ovine exocrine pancreas", *American Journal of Physiology*, Mar. 1983, pp. G284-G290, vol. 244, No. 3, The American Physiological Society.
Harada, Etsumori, et al., "Postnatal development of biliary and pancreatic exocrine secretion in piglets", *Comparative Biochemistry and Physiology*, 1988, pp. 43-51, vol. 91A, No. 1, Pergamon Press, London.
Harada, Etsumori, et al., "Comparison of Pancreatic Exocrine Secretin via Endogenous Secretin by Intestinal Infusion of Hydrochloric Acid and Monocarboxylic Acid in Anesthetized Piglets", *Japanese Journal of Physiology*, 1986, pp. 843-856, vol. 36, No. 5.
Huyghebaert, Gerard, "The influence of the addition of 'organic acid'—preparations on the zootechnical performances of broiler chickens", Report: CLO-DVV, 1999.
Kato, Seiyu, et al., "Effect of Short-Chain Fatty Acids on Pancreatic Exocrine Secretion in Calves Aged 2 Weeks and 13 Weeks", *Japanese Veterinary Science*, Dec. 1989, pp. 1123-1127, vol. 51, No. 6, Japanese Society of Veterinary Science.
Knight, Christopher D., et al., "Comparative Absorption of 2-Hydroxy-4 (Methylthio) butanoic Acid and L-Methonine in the Broiler Chick", *Journal of Nutrition*, Nov. 1984, pp. 2179-2186, vol. 114, No. 11, Wistar Institute of Anatomy and Biology, Philadelphia.
Lamikanra, O. et al., "Biochemical and Microbial Changes during the Storage of Minimally Processed Cantaloupe", *Journal of Agricultural and Food Chemistry*, 2000, vol. 48(12), Abstract, American Chemical Society.
Makkink, Carolien, "Acid binding capacity in feedstuffs", *Feed International*, Oct. 2001, pp. 24-27.
Martin, F.L., et al., "The Effect of Tuber Composition on Potato Crisp Flavour," Department of Food Science & Technology, University of Reading, Proceedings of the Weurman Flavour Research Symposium, Germany, Jun. 22-25, 1999, Chemical Abstracts, Database No. 136:69008, Abstract only.
Mroz, Z., "Supplementary organic acids and their interactive effects with microbial phytase in diets for pigs and poultry", Proceedings, Annual Conference on Phytase in Animal Nutrition, 2000, pp. 1-25, Lubin, Poland.
Nitsan, Zafrira, et al., "Growth and development of the digestive organs and some enzymes in broiler chicks after hatching", *British Poultry Science*, Jul. 1991, pp. 515-523, vol. 32, No. 3.
Nitsan, Zafrira, et al., "The effects of force-feeding on enzymes of the liver, kidney, pancreas and digestive tract of chicks", *The British Journal of Nutrition*, Sep. 1974, pp. 241-247, vol. 32 No. 2, Cambridge University Press, England.
Ozer, Barbaros et al., "Effect of addition of amino acids, treatment with beta -galactosidase and use of heat-shocked cultures on the acetaldehyde level in yoghurt", *International Journal of Dairy Technology*, 2002, vol. 55(4), Abstract, Blackwell Science Ltd.
Partanen, Kirsi, "Organic acids—their efficacy and modes of action in pigs", Gut Environment of Pigs, 2001, pp. 201, Nottingham University Press, Nottingham, UK.
Partanen, Kirsi H., et al., "Organic acids for performance enhancement in pig diets", *Nutr. Res. Rev.*, 1999, pp. 117-145, vol. 12.
Robinson, et al., "Influence of Abomasal Infusion of High Levels of Lysine or Methionine, or Both, on Ruminal Fermentation, Eating Behaviour and Performance of Lactating Dairy Cows," Journal of Animal Science, 2000, pp. 1067-1077, vol. 78, No. 4, Abstract Only.
Roura, Eugeni, et al., "Prevention of Immunologic Stress Contributes to the Growth-Permitting Ability of Dietary Antibiotics of Chicks", *The Journal of Nutrition*, 1992, pp. 2383-2390, vol. 122, Wistar Institute of Anatomy and Biology, Philadelphia.
Scipioni, Rosanna, et al., "Ricerche sull'impiego di diete acidificante nello svezzamento precoce del suinetti", *Zool. Nutr. Anim.*, 1978, pp. 201-218, vol. 4.

Smit, G., et al., "Flavour Formation by Enzymatic Conversion of Amino Acids," Proceedings of the Weurman Flavour Research Symposium, Germany, Jun. 22-25, 1999, Chemical Abstracts, Database No. 136:84940, Abstract only.

Smulders, A.C.M.J., et al., "Effect of antimicrobial growth promoter in feeds with different levels of undigestible protein on broiler performance", Proceedings, World's Poultry Sci. Meeting, Aug. 1999, pp. 177-179, Veldhoven, Netherlands.

Thaela, M.-J., et al., "Effect of lactic acid supplementation in pigs after weaning", *Journal of Animal And Feed Science*, 1998, pp. 181, vol. 7.

Thomlinson, J.R., et al., "Dietary manipulation of gastric pH in the prophylaxis of eneteric disease in weaned pigs: Some field observations", *The Veterinary Record*, Aug. 1981, pp. 120-122, vol. 109, British Veterinary Associate, London.

Visek, W.J., "The mode of growth promotion by antibiotics", *Journal of Animal Science*, Apr. 1978, pp. 1447-1469, vol. 46, No. 5, American Society of Animal Science.

* cited by examiner

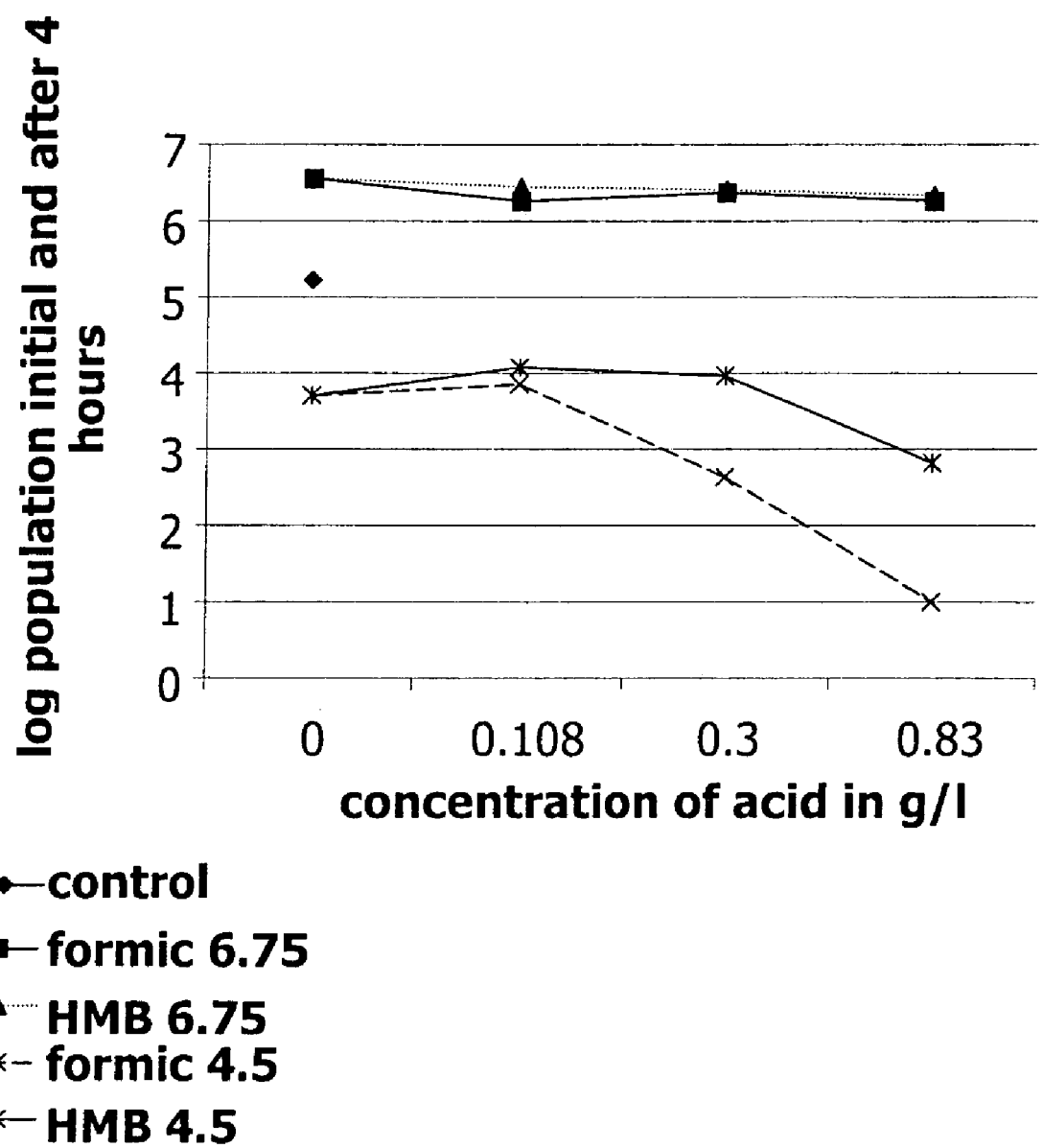

PALATABILITY OF AQUACULTURE FEED

REFERENCE TO RELATED APPLICATIONS

This application is a continuation-in-part of U.S. application Ser. No. 10/652,745 which claims the benefit under 35 U.S.C. 119(e) of U.S. Provisional Application No. 60/456,673, filed Mar. 21, 2003, Provisional Application No. 60/456,732, filed Mar. 21, 2003, and Provisional Application No. 60/465,549, filed Apr. 25, 2003; which is hereby incorporated by reference in its entirety.

FIELD OF THE INVENTION

The present invention generally relates to methods of increasing the palatability of aquaculture feed.

BACKGROUND OF THE INVENTION

Enhancing the palatability of animal food is a continuing endeavor by food manufacturers. Addition of palatants to the food is desirable as a means to increase acceptance by the animals, resulting in improved health of the animal, increased weight gain, etc. In order to provide a cost-effective feeding program aquaculture feeds should be easily sensed by the animal and stimulate the animal to seek out the food. Thus, palatants are used in foods for aquaculture to maximize the amount of food eaten. Particularly, in aquaculture feeds, acceptance of the feed by fish is decreased as fishmeal is replaced with vegetable proteins.

Supplemental methionine has occasionally been used to balance rations to accepted or perceived amino acid requirements for select aquatic species. L-methionine is known as an attractant for some species and a repellant for other species. Accordingly, a need has remained for a pallatant for aquaculture that excites the species to accept the aquaculture feed in a greater amount.

SUMMARY OF THE INVENTION

The present invention is directed to a method of enhancing the palatability of feed for aquaculture, particularly feed for fish and shellfish. The method comprises treating the feed for aquaculture with a compound of formula I, wherein the concentration of the compound of formula I is from about 0.005 wt. % to about 0.5 wt. % based on the total weight of the aquaculture feed.

Another aspect of the present invention is a method of feeding fish. The method comprises feeding the fish a fish food comprising a compound of formula I wherein the concentration of said compound of formula I is effective to enhance the palatability of said fish food.

Yet another aspect of the present invention is a method of feeding fish comprising feeding the fish a fish food comprising a compound of formula I wherein the concentration of the compound of formula I in the fish food is more than about 0.001 wt. % and less than 0.05 wt. %.

A further aspect of the present invention is a method of feeding fish comprising feeding the fish a fish food comprising a compound of formula I wherein the fish being fed comprise fish other than catfish and salmon.

Still another aspect of the present invention is a fish food composition comprising a compound of formula I wherein the concentration of the compound of formula I in the fish food is more than about 0.001 wt. % and less than 0.05 wt. %.

Other objects and features will be in part apparent and in part pointed out hereinafter.

BRIEF DESCRIPTION OF THE DRAWINGS

FIG. 2D is a graph illustrating the pH-dependent antibacterial effect of formic acid and Alimet® on the number of colony forming units of $C.$ $jejuni$.

DETAILED DESCRIPTION OF THE PREFERRED EMBODIMENTS

Figure 1A:
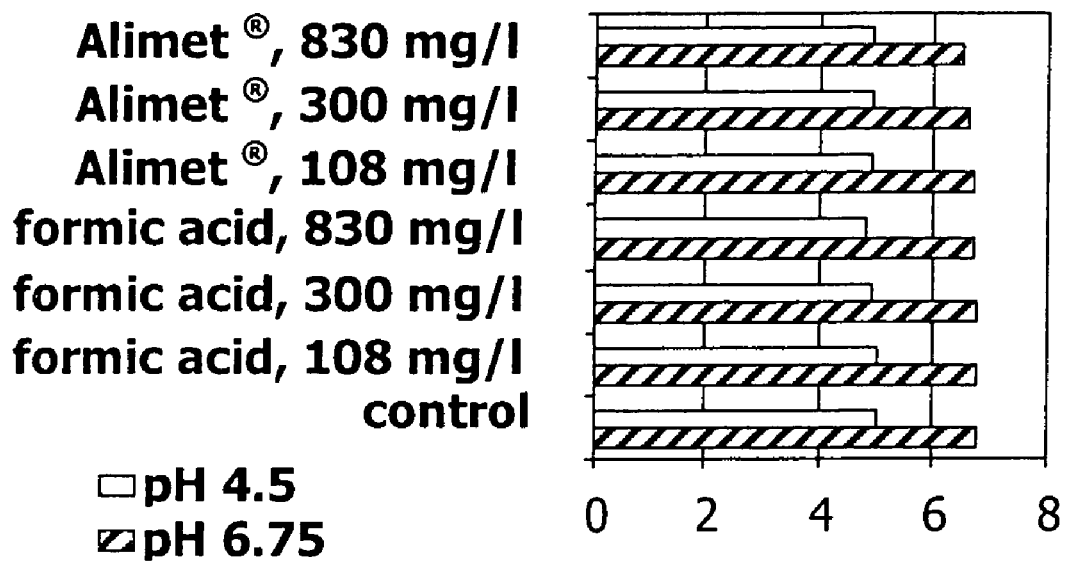
FIG. 1A is a graph illustrating the effect of varying doses (0.108, 0.3, and 0.83 g/L) of formic acid and a concentrated aqueous solution of 2-hydroxy-4-methylthiobutanoic acid (sold under the trade designation Alimet®) at pH 4.5 and 6.75 on the number of colony forming units of $S.$ $enteritidis$ after 4 hours.
Figure 1B:
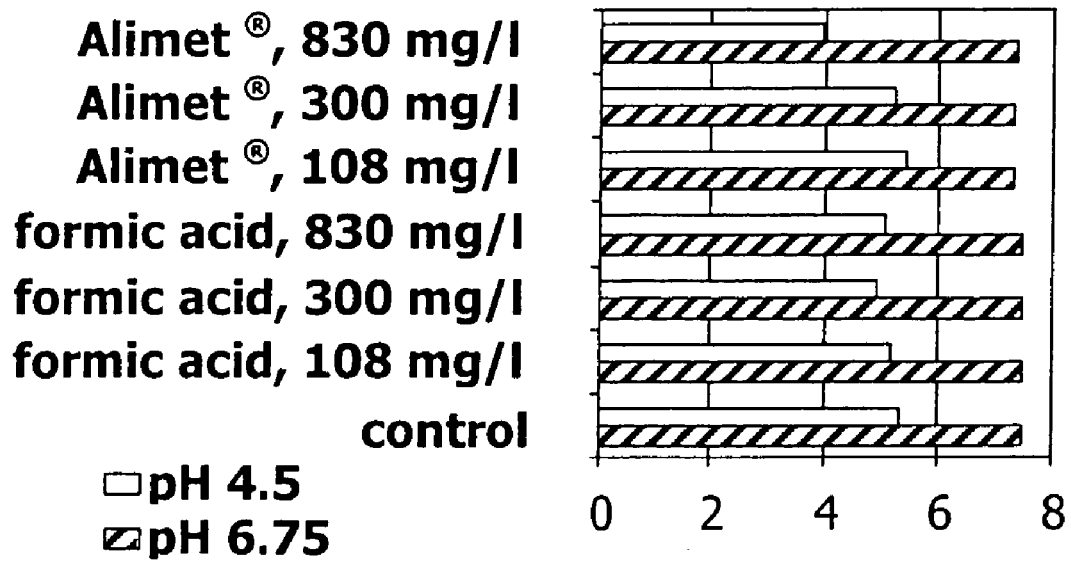
FIG. 1B is a graph illustrating the effect of varying doses (0.108, 0.3, and 0.83 g/L) of formic acid and Alimet® at pH 4.5 and 6.75 on the number of colony forming units of $E.$ $coli$ after 4 hours.
Figure 1C:
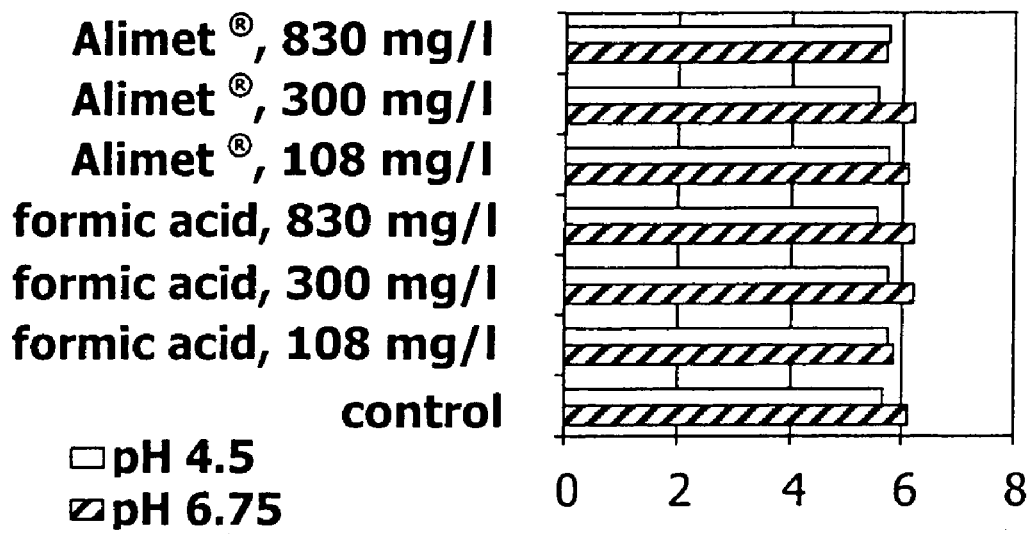
FIG. 1C is a graph illustrating the effect of varying doses (0.108, 0.3, and 0.83 g/L) of formic acid and Alimet® at pH 4.5 and 6.75 on the number of colony forming units of $L.$ $plantarum$ after 6 hours.
Figure 1D:
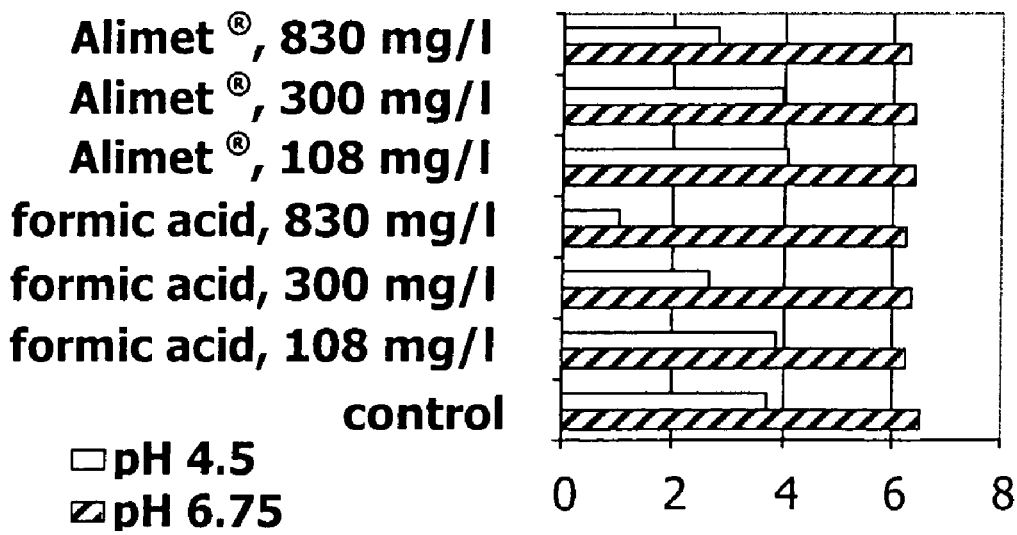
FIG. 1D is a graph illustrating the effect of varying doses (0.108, 0.3, and 0.83 g/L) of formic acid and Alimet® at pH 4.5 and 6.75 on the number of colony forming units of $C.$ $jejuni$ after 6 hours.
Figure 2A:
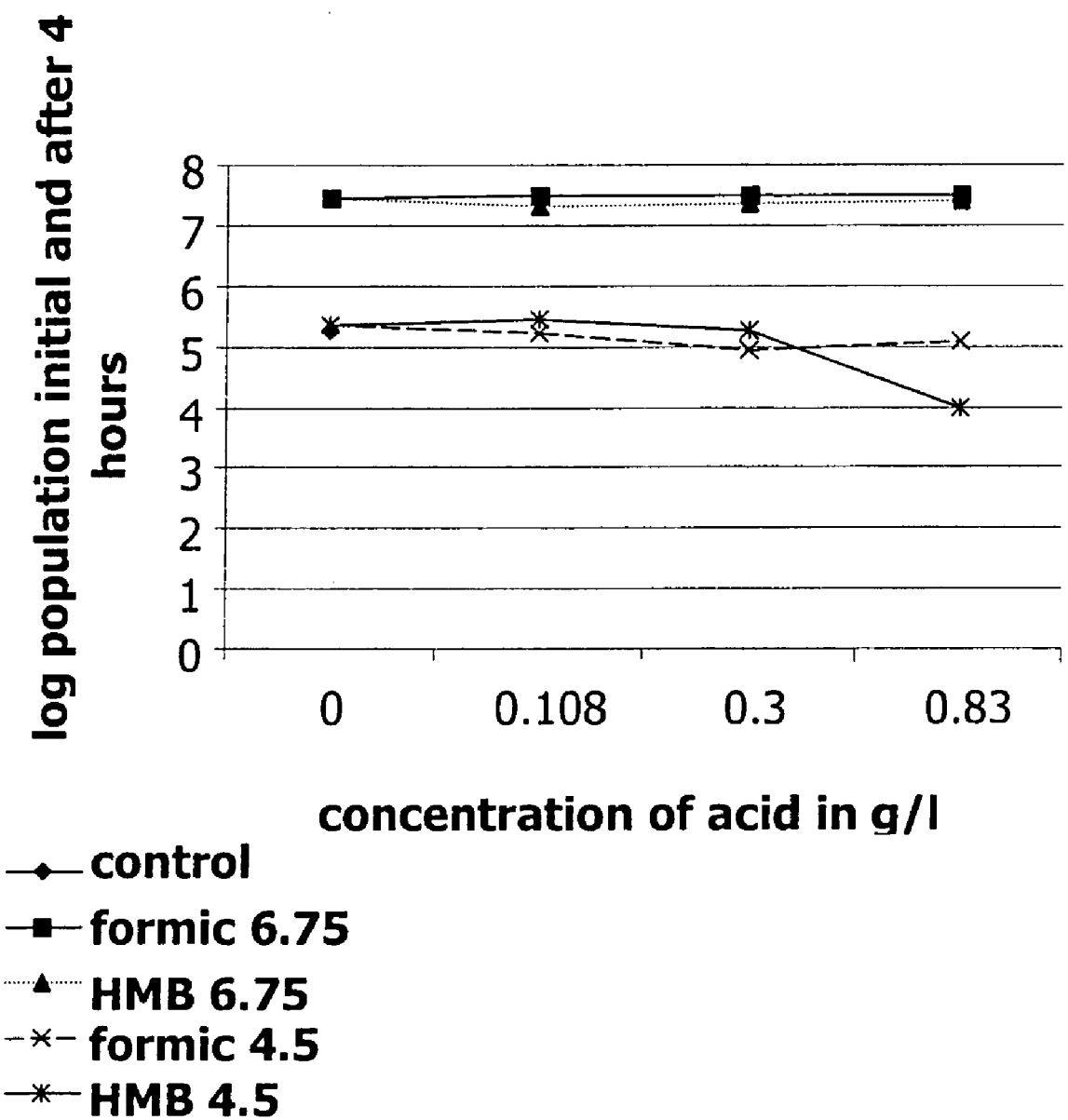
FIG. 2A is a graph illustrating the pH-dependent antibacterial effect of formic acid and Alimet® on the number of colony forming units of $S.$ $enteritidis$.
Figure 2B:
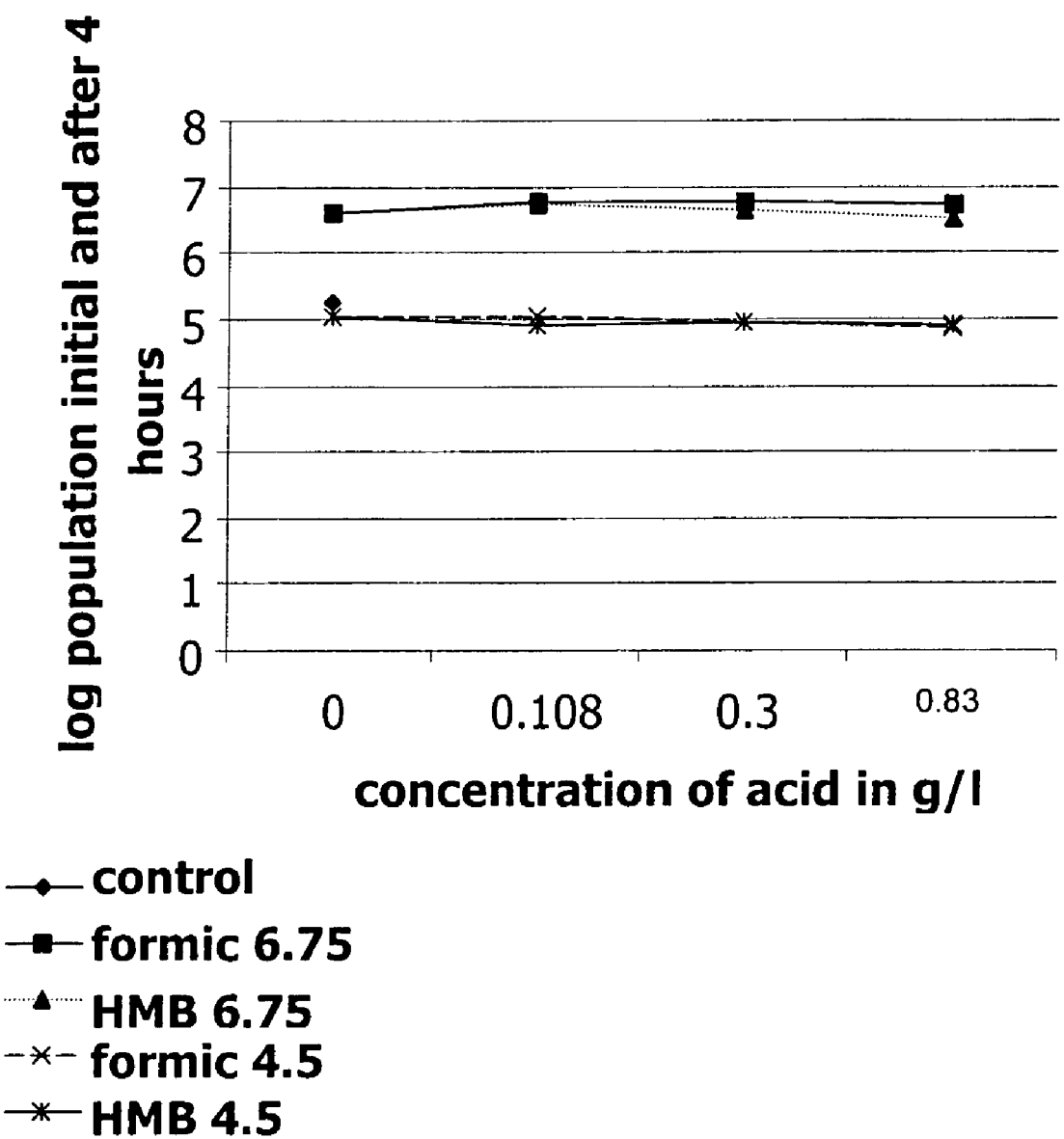
FIG. 2B is a graph illustrating the pH-dependent antibacterial effect of formic acid and Alimet® on the number of colony forming units of $E.$ $coli$.
Figure 2C:
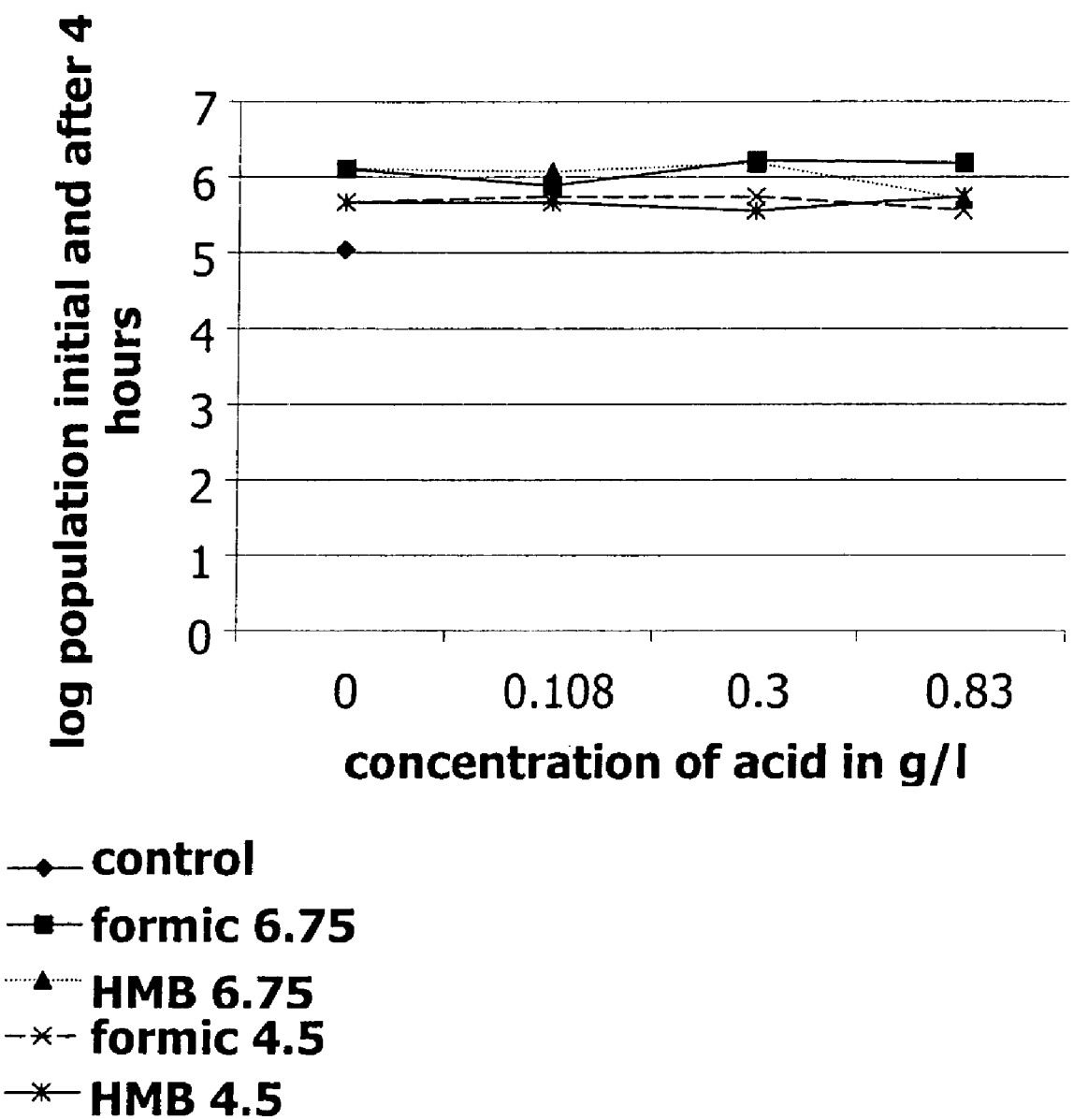
FIG. 2C is a graph illustrating the pH-dependent antibacterial effect of formic acid and Alimet® on the number of colony forming units of $L.$ $plantarum$.
Figure 3:
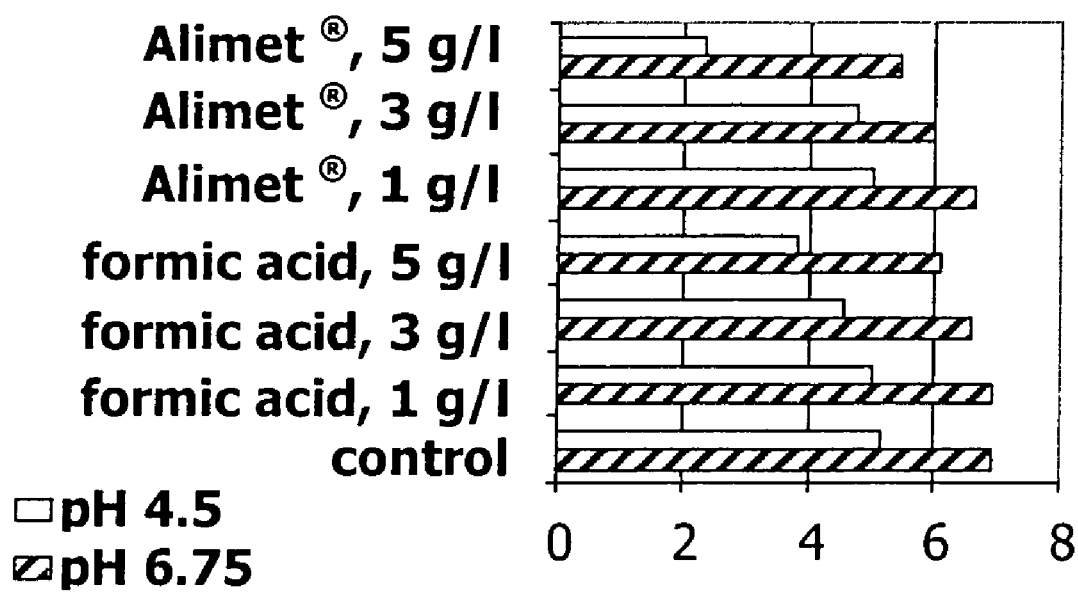
FIG. 3 is a graph illustrating the effect of varying doses (1, 3 and 5 g/L) formic acid and Alimet® on the number of colony forming units of $S.$ $enteritidis$ after 4 hours at pH 4.5 and 6.75.
Figure 4A:
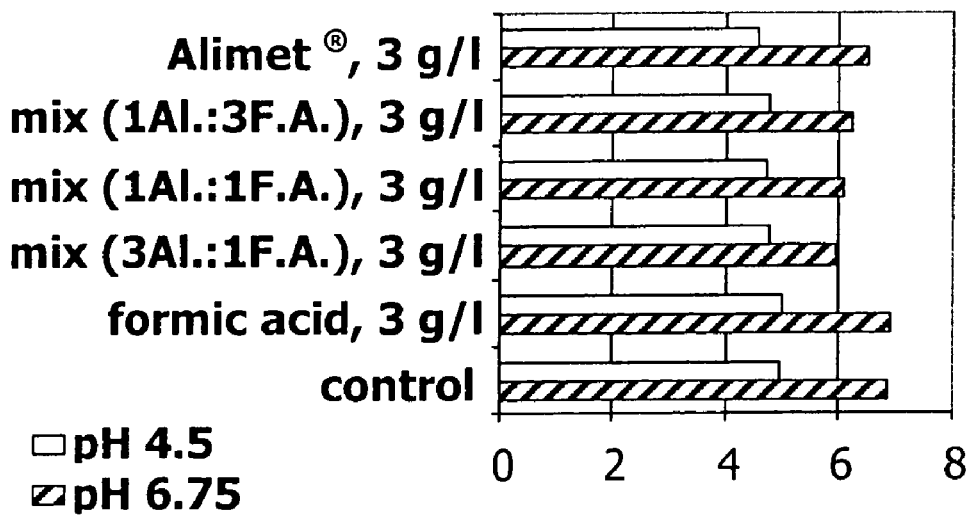
FIGS. 4A and 4B are graphs illustrating the effect of varying doses of a combination of formic acid and Alimet® on the number of colony forming units of $S.$ $enteritidis$ after 4 hours at pH 4.5 and 6.75.
Figure 4B:
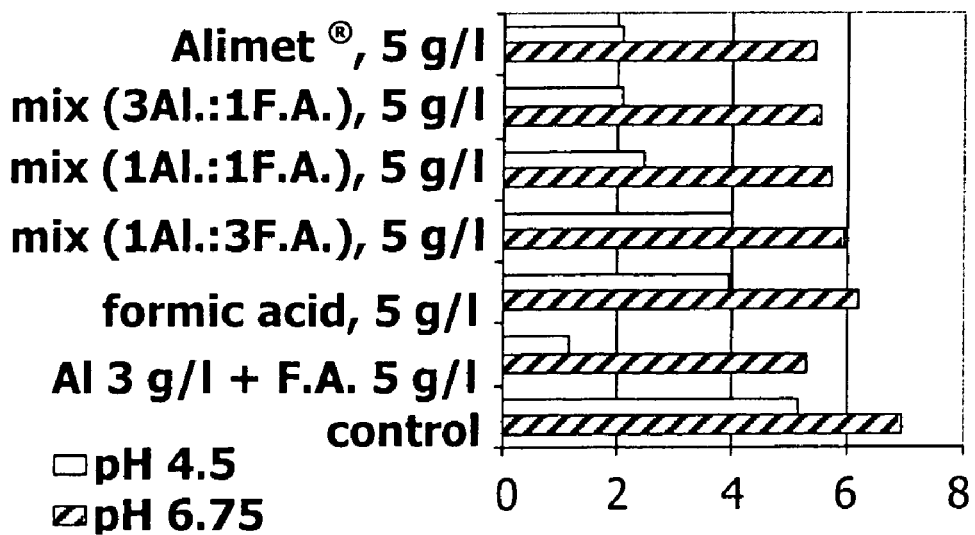

In accordance with then invention described herein, various useful and salutary applications have been discovered wherein the compound of formula I is incorporated into, or otherwise used to treat animal feeds. A further application which has now been discovered comprises a method for enhancing the palatability of feed for aquaculture, the method comprising treating the feed with a compound of formula I, preferably by incorporating such compound in the feed formulation. With the change in feed for aquaculture from fishmeal-based feeds to vegetable protein-based feeds, the problem of palatability of aquaculture feeds has increased. Thus, in order to enhance growth and general health, there has been a need for a palatant (e.g., attractant) that alters the aquatic species feeding behavior by increasing the number of contacts of the species with the feed. For certain species, this altered feeding behavior is exhibited by an increase in the number of bites of the feed the species takes over a time period. Generally, for the compounds of formula I, a relatively low concentration in the aquaculture feed is needed to induce this increase in contacts with the feed.

Another aspect of the present invention is a method inhibiting microbes in animal feed, said method comprising treating said feed with a compound of Formula I.

Compounds of Formula I have the following structure:

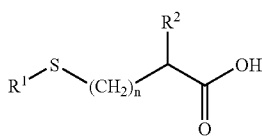

wherein $R^1$ is an alkyl group having from one to four carbon atoms;

n is an integer from 0 to 2;

$R^2$ is selected from the group consisting of hydroxy, amino, —$OCOR^3$, or —$NHCOR^3$;

and wherein $R^3$ is an organic acid derivative;

or a salt thereof.

The term "organic acid derivative" means a derivative of any suitable organic acid resulting from removal of the carboxyl function from the acid. Preferably, the organic acid has from one to eight carbon atoms. Suitable organic acid derivatives include, but are not limited to, derivatives of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid.

Preferably, $R^1$ is methyl, ethyl, propyl (including n-propyl and isopropyl), or butyl (including n-butyl, sec-butyl, and t-butyl). In another embodiment, preferably, $R^2$ is selected from the group consisting of hydroxy, —$OCOR^3$, or —$NHCOR^3$;

In a preferred embodiment, the compound of Formula I is selected from the following list of compounds:

1-hydroxy-1-(methylthio)acetic acid;
1-hydroxy-1-(ethylthio)acetic acid;
1-hydroxy-1-(propylthio)acetic acid;
1-hydroxy-1-(butylthio)acetic acid;
1-amino-1-(methylthio)acetic acid;
1-amino-1-(ethylthio)acetic acid;
1-amino-1-(propylthio)acetic acid;
1-amino-1-(butylthio)acetic acid;
1-carboxy-1-(methylthio)acetic acid;
1-acetyloxy-1-(methylthio)acetic acid;
1-propionyloxy-1-(methylthio)acetic acid;
1-butyryloxy-1-(methylthio)acetic acid;
1-benzoyloxy-1-(methylthio)acetic acid;
1-lactoyloxy-1-(methylthio)acetic acid;
1-[2-carboxy-2-(hydroxy)propionyloxy]-1-(methylthio)acetic acid;
1-[2-carboxy-1-(hydroxy)propionyloxy]-1-(methylthio)acetic acid;
1-[2-carboxy-1,2-(dihydroxy)propionyloxy]-1-(methylthio)acetic acid;
1-[hydroxy(phenyl)acetyl]oxy-1-(methylthio)acetic acid;
1-[2,3-dicarboxy-2-(hydroxy)butyryloxy]-1-(methylthio)acetic acid;
1-[2-carboxy-1-carboxymethyl-1-(hydroxy)propionyloxy]-1-(methylthio)acetic acid;
1-(3-carboxyacryloyl)oxy-1-(methylthio)acetic acid;
1-(2,4-pentadienoyloxy)-1-(methylthio)acetic acid;
1-(2-carboxypropionyloxy)-1-(methylthio)acetic acid;
1-[(4-carboxy)amyloxy]-1-(methylthio)acetic acid;
1-glycoloyloxy-1-(methylthio)acetic acid;
1-glutaroyloxy-1-(methylthio)acetic acid;
1-formylamino-1-(methylthio)acetic acid;
1-acetylamino-1-(methylthio)acetic acid;
1-propionylamino-1-(methylthio)acetic acid;
1-butyrylamino-1-(methylthio)acetic acid;
1-benzoylamino-1-(methylthio)acetic acid;
1-lactoylamino-1-(methylthio)acetic acid;
1-[2-carboxy-2-(hydroxy)propionylamino]-1-(methylthio)acetic acid;
1-[2-carboxy-1-(hydroxy)propionylamino]-1-(methylthio)acetic acid;
1-[2-carboxy-1,2-(dihydroxy)propionylamino]-1-(methylthio)acetic acid;
1-[hydroxy(phenyl)acetyl]amino-1-(methylthio)acetic acid;
1-[2,3-dicarboxy-2-(hydroxy)butyrylamino]-1-(methylthio)acetic acid;
1-[2-carboxy-1-carboxymethyl-1-(hydroxy)propionylamino]-1-(methylthio)acetic acid;
1-(3-carboxyacryloyl)amino-1-(methylthio)acetic acid;
1-(2,4-pentadienoylamino)-1-(methylthio)acetic acid;
1-(2-carboxypropionylamino)-1-(methylthio)acetic acid;
1-[(4-carboxy)amylamino]-1-(methylthio)acetic acid;
1-glycoloylamino-1-(methylthio)acetic acid;
1-glutaroylamino-1-(methylthio)acetic acid;
1-carboxy-(ethylthio)acetic acid;
1-acetyloxy-(ethylthio)acetic acid;
1-propionyloxy-(ethylthio)acetic acid;
1-butyryloxy-(ethylthio)acetic acid;
1-benzoyloxy-(ethylthio)acetic acid;
1-lactoyloxy-(ethylthio)acetic acid;

1-[2-carboxy-2-(hydroxy)propionyloxy]-(ethylthio)acetic acid;
1-[2-carboxy-1-(hydroxy)propionyloxy]-(ethylthio)acetic acid;
1-[2-carboxy-1,2-(dihydroxy)propionyloxy]-(ethylthio)acetic acid;
1-[hydroxy(phenyl)acetyl]oxy-(ethylthio)acetic acid;
1-[2,3-dicarboxy-2-(hydroxy)butyryloxy]-(ethylthio)acetic acid;
1-[2-carboxy-1-carboxymethyl-1-(hydroxy)propionyloxy]-(ethylthio)acetic acid;
1-(3-carboxyacryloyl)oxy-(ethylthio)acetic acid;
1-(2,4-pentadienoyloxy)-(ethylthio)acetic acid;
1-(2-carboxypropionyloxy)-(ethylthio)acetic acid;
1-[(4-carboxy)amyloxy]-(ethylthio)acetic acid;
1-glycoloyloxy-(ethylthio)acetic acid;
1-glutaroyloxy-(ethylthio)acetic acid;
1-formylamino-(ethylthio)acetic acid;
1-acetylamino-(ethylthio)acetic acid;
1-propionylamino-(ethylthio)acetic acid;
1-butyrylamino-(ethylthio)acetic acid;
1-benzoylamino-(ethylthio)acetic acid;
1-lactoylamino-(ethylthio)acetic acid;
1-[2-carboxy-2-(hydroxy)propionylamino]-(ethylthio)acetic acid;
1-[2-carboxy-1-(hydroxy)propionylamino]-(ethylthio)acetic acid;
1-[2-carboxy-1,2-(dihydroxy)propionylamino]-(ethylthio)acetic acid;
1-[hydroxy(phenyl)acetyl]amino-(ethylthio)acetic acid;
1-[2,3-dicarboxy-2-(hydroxy)butyrylamino]-(ethylthio)acetic acid;
1-[2-carboxy-1-carboxymethyl-1-(hydroxy)propionylamino]-(ethylthio)acetic acid;
1-(3-carboxyacryloyl)amino-(ethylthio)acetic acid;
1-(2,4-pentadienoylamino)-(ethylthio)acetic acid;
1-(2-carboxypropionylamino)-(ethylthio)acetic acid;
1-[(4-carboxy)amylamino]-(ethylthio)acetic acid;
1-glycoloylamino-(ethylthio)acetic acid;
1-glutaroylamino-(ethylthio)acetic acid;
1-carboxy-(propylthio)acetic acid;
1-acetyloxy-(propylthio)acetic acid;
1-propionyloxy-(propylthio)acetic acid;
1-butyryloxy-(propylthio)acetic acid;
1-benzoyloxy-(propylthio)acetic acid;
1-lactoyloxy-(propylthio)acetic acid;
1-[2-carboxy-2-(hydroxy)propionyloxy]-(propylthio)acetic acid;
1-[2-carboxy-1-(hydroxy)propionyloxy]-(propylthio)acetic acid;
1-[2-carboxy-1,2-(dihydroxy)propionyloxy]-(propylthio)acetic acid;
1-[hydroxy(phenyl)acetyl]oxy-(propylthio)acetic acid;
1-[2,3-dicarboxy-2-(hydroxy)butyryloxy]-(propylthio)acetic acid;
1-[2-carboxy-1-carboxymethyl-1-(hydroxy)propionyloxy]-(propylthio)acetic acid;
1-(3-carboxyacryloyl)oxy-(propylthio)acetic acid;
1-(2,4-pentadienoyloxy)-(propylthio)acetic acid;
1-(2-carboxypropionyloxy)-(propylthio)acetic acid;
1-[(4-carboxy)amyloxy]-(propylthio)acetic acid;
1-glycoloyloxy-(propylthio)acetic acid;
1-glutaroyloxy-(propylthio)acetic acid;
1-formylamino-(propylthio)acetic acid;
1-acetylamino-(propylthio)acetic acid;
1-propionylamino-(propylthio)acetic acid;
1-butyrylamino-(propylthio)acetic acid;
1-benzoylamino-(propylthio)acetic acid;
1-lactoylamino-(propylthio)acetic acid;
1-[2-carboxy-2-(hydroxy)propionylamino]-(propylthio)acetic acid;
1-[2-carboxy-1-(hydroxy)propionylamino]-(propylthio)acetic acid;
1-[2-carboxy-1,2-(dihydroxy)propionylamino]-(propylthio)acetic acid;
1-[hydroxy(phenyl)acetyl]amino-(propylthio)acetic acid;
1-[2,3-dicarboxy-2-(hydroxy)butyrylamino]-(propylthio)acetic acid;
1-[2-carboxy-1-carboxymethyl-1-(hydroxy)propionylamino]-(propylthio)acetic acid;
1-(3-carboxyacryloyl)amino-(propylthio)acetic acid;
1-(2,4-pentadienoylamino)-(propylthio)acetic acid;
1-(2-carboxypropionylamino)-(propylthio)acetic acid;
1-[(4-carboxy)amylamino]-(propylthio)acetic acid;
1-glycoloylamino-(propylthio)acetic acid;
1-glutaroylamino-(propylthio)acetic acid;
1-carboxy-(butylthio)acetic acid;
1-acetyloxy-(butylthio)acetic acid;
1-propionyloxy-(butylthio)acetic acid;
1-butyryloxy-(butylthio)acetic acid;
1-benzoyloxy-(butylthio)acetic acid;
1-lactoyloxy-(butylthio)acetic acid;
1-[2-carboxy-2-(hydroxy)propionyloxy]-(butylthio)acetic acid;
1-[2-carboxy-1-(hydroxy)propionyloxy]-(butylthio)acetic acid;
1-[2-carboxy-1,2-(dihydroxy)propionyloxy]-(butylthio)acetic acid;
1-[hydroxy(phenyl)acetyl]oxy-(butylthio)acetic acid;
1-[2,3-dicarboxy-2-(hydroxy)butyryloxy]-(butylthio)acetic acid;
1-[2-carboxy-1-carboxymethyl-1-(hydroxy)propionyloxy]-(butylthio)acetic acid;
1-(3-carboxyacryloyl)oxy-(butylthio)acetic acid;
1-(2,4-pentadienoyloxy)-(butylthio)acetic acid;
1-(2-carboxypropionyloxy)-(butylthio)acetic acid;
1-[(4-carboxy)amyloxy]-(butylthio)acetic acid;
1-glycoloyloxy-(butylthio)acetic acid;
1-glutaroyloxy-(butylthio)acetic acid;
1-formylamino-(butylthio)acetic acid;
1-acetylamino-(butylthio)acetic acid;
1-propionylamino-(butylthio)acetic acid;
1-butyrylamino-(butylthio)acetic acid;
1-benzoylamino-(butylthio)acetic acid;
1-lactoylamino-(butylthio)acetic acid;
1-[2-carboxy-2-(hydroxy)propionylamino]-(butylthio)acetic acid;
1-[2-carboxy-1-(hydroxy)propionylamino]-(butylthio)acetic acid;
1-[2-carboxy-1,2-(dihydroxy)propionylamino]-(butylthio)acetic acid;
1-[hydroxy(phenyl)acetyl]amino-(butylthio)acetic acid;
1-[2,3-dicarboxy-2-(hydroxy)butyrylamino]-(butylthio)acetic acid;
1-[2-carboxy-1-carboxymethyl-1-(hydroxy)propionylamino]-(butylthio)acetic acid;
1-(3-carboxyacryloyl)amino-(butylthio)acetic acid;
1-(2,4-pentadienoylamino)-(butylthio)acetic acid;
1-(2-carboxypropionylamino)-(butylthio)acetic acid;
1-[(4-carboxy)amylamino]-(butylthio)acetic acid;
1-glycoloylamino-(butylthio)acetic acid;
1-glutaroylamino-(butylthio)acetic acid;
2-hydroxy-3-(methylthio)propanoic acid;
2-hydroxy-3-(ethylthio)propanoic acid;

2-hydroxy-3-(propylthio)propanoic acid;
2-hydroxy-3-(butylthio)propanoic acid;
2-amino-3-(methylthio)propanoic acid;
2-amino-3-(ethylthio)propanoic acid;
2-amino-3-(propylthio)propanoic acid;
2-amino-3-(butylthio)propanoic acid;
2-carboxy-3-(methylthio)propanoic acid;
2-acetyloxy-3-(methylthio)propanoic acid;
2-propionyloxy-3-(methylthio)propanoic acid;
2-butyryloxy-3-(methylthio)propanoic acid;
2-benzoyloxy-3-(methylthio)propanoic acid;
2-lactoyloxy-3-(methylthio)propanoic acid;
2-[2-carboxy-2-(hydroxy)propionyloxy]-3-(methylthio)propanoic acid;
2-[2-carboxy-1-(hydroxy)propionyloxy]-3-(methylthio)propanoic acid;
2-[2-carboxy-1,2-(dihydroxy)propionyloxy]-3-(methylthio)propanoic acid;
2-[hydroxy(phenyl)acetyl]oxy-3-(methylthio)propanoic acid;
2-[2,3-dicarboxy-2-(hydroxy)butyryloxy]-3-(methylthio)propanoic acid;
2-[2-carboxy-1-carboxymethyl-1-(hydroxy)propionyloxy]-3-(methylthio)propanoic acid;
2-(3-carboxyacryloyl)oxy-3-(methylthio)propanoic acid;
2-(2,4-pentadienoyloxy)-3-(methylthio)propanoic acid;
2-(2-carboxypropionyloxy)-3-(methylthio)propanoic acid;
2-[(4-carboxy)amyloxy]-3-(methylthio)propanoic acid;
2-glycoloyloxy-3-(methylthio)propanoic acid;
2-glutaroyloxy-3-(methylthio)propanoic acid;
2-formylamino-3-(methylthio)propanoic acid;
2-acetylamino-3-(methylthio)propanoic acid;
2-propionylamino-3-(methylthio)propanoic acid;
2-butyrylamino-3-(methylthio)propanoic acid;
2-benzoylamino-3-(methylthio)propanoic acid;
2-lactoylamino-3-(methylthio)propanoic acid;
2-[2-carboxy-2-(hydroxy)propionylamino]-3-(methylthio)propanoic acid;
2-[2-carboxy-1-(hydroxy)propionylamino]-3-(methylthio)propanoic acid;
2-[2-carboxy-1,2-(dihydroxy)propionylamino]-3-(methylthio)propanoic acid;
2-[hydroxy(phenyl)acetyl]amino-3-(methylthio)propanoic acid;
2-[2,3-dicarboxy-2-(hydroxy)butyrylamino]-3-(methylthio)propanoic acid;
2-[2-carboxy-1-carboxymethyl-1-(hydroxy)propionylamino]-3-(methylthio)propanoic acid;
2-(3-carboxyacryloyl)amino-3-(methylthio)propanoic acid;
2-(2,4-pentadienoylamino)-3-(methylthio)propanoic acid;
2-(2-carboxypropionylamino)-3-(methylthio)propanoic acid;
2-[(4-carboxy)amylamino]-3-(methylthio)propanoic acid;
2-glycoloylamino-3-(methylthio)propanoic acid;
2-glutaroylamino-3-(methylthio)propanoic acid;
2-carboxy-3-(ethylthio)propanoic acid;
2-acetyloxy-3-(ethylthio)propanoic acid;
2-propionyloxy-3-(ethylthio)propanoic acid;
2-butyryloxy-3-(ethylthio)propanoic acid;
2-benzoyloxy-3-(ethylthio)propanoic acid;
2-lactoyloxy-3-(ethylthio)propanoic acid;
2-[2-carboxy-2-(hydroxy)propionyloxy]-3-(ethylthio)propanoic acid;
2-[2-carboxy-1-(hydroxy)propionyloxy]-3-(ethylthio)propanoic acid;
2-[2-carboxy-1,2-(dihydroxy)propionyloxy]-3-(ethylthio)propanoic acid;
2-[hydroxy(phenyl)acetyl]oxy-3-(ethylthio)propanoic acid;
2-[2,3-dicarboxy-2-(hydroxy)butyryloxy]-3-(ethylthio)propanoic acid;
2-[2-carboxy-1-carboxymethyl-1-(hydroxy)propionyloxy]-3-(ethylthio)propanoic acid;
2-(3-carboxyacryloyl)oxy-3-(ethylthio)propanoic acid;
2-(2,4-pentadienoyloxy)-3-(ethylthio)propanoic acid;
2-(2-carboxypropionyloxy)-3-(ethylthio)propanoic acid;
2-[(4-carboxy)amyloxy]-3-(ethylthio)propanoic acid;
2-glycoloyloxy-3-(ethylthio)propanoic acid;
2-glutaroyloxy-3-(ethylthio)propanoic acid;
2-formylamino-3-(ethylthio)propanoic acid;
2-acetylamino-3-(ethylthio)propanoic acid;
2-propionylamino-3-(ethylthio)propanoic acid;
2-butyrylamino-3-(ethylthio)propanoic acid;
2-benzoylamino-3-(ethylthio)propanoic acid;
2-lactoylamino-3-(ethylthio)propanoic acid;
2-[2-carboxy-2-(hydroxy)propionylamino]-3-(ethylthio)propanoic acid;
2-[2-carboxy-1-(hydroxy)propionylamino]-3-(ethylthio)propanoic acid;
2-[2-carboxy-1,2-(dihydroxy)propionylamino]-3-(ethylthio)propanoic acid;
2-[hydroxy(phenyl)acetyl]amino-3-(ethylthio)propanoic acid;
2-[2,3-dicarboxy-2-(hydroxy)butyrylamino]-3-(ethylthio)propanoic acid;
2-[2-carboxy-1-carboxymethyl-1-(hydroxy)propionylamino]-3-(ethylthio)propanoic acid;
2-(3-carboxyacryloyl)amino-3-(ethylthio)propanoic acid;
2-(2,4-pentadienoylamino)-3-(ethylthio)propanoic acid;
2-(2-carboxypropionylamino)-3-(ethylthio)propanoic acid;
2-[(4-carboxy)amylamino]-3-(ethylthio)propanoic acid;
2-glycoloylamino-3-(ethylthio)propanoic acid;
2-glutaroylamino-3-(ethylthio)propanoic acid;
2-carboxy-3-(propylthio)propanoic acid;
2-acetyloxy-3-(propylthio)propanoic acid;
2-propionyloxy-3-(propylthio)propanoic acid;
2-butyryloxy-3-(propylthio)propanoic acid;
2-benzoyloxy-3-(propylthio)propanoic acid;
2-lactoyloxy-3-(propylthio)propanoic acid;
2-[2-carboxy-2-(hydroxy)propionyloxy]-3-(propylthio)propanoic acid;
2-[2-carboxy-1-(hydroxy)propionyloxy]-3-(propylthio)propanoic acid;
2-[2-carboxy-1,2-(dihydroxy)propionyloxy]-3-(propylthio)propanoic acid;
2-[hydroxy(phenyl)acetyl]oxy-3-(propylthio)propanoic acid;
2-[2,3-dicarboxy-2-(hydroxy)butyryloxy]-3-(propylthio)propanoic acid;
2-[2-carboxy-1-carboxymethyl-1-(hydroxy)propionyloxy]-3-(propylthio)propanoic acid;
2-(3-carboxyacryloyl)oxy-3-(propylthio)propanoic acid;
2-(2,4-pentadienoyloxy)-3-(propylthio)propanoic acid;
2-(2-carboxypropionyloxy)-3-(propylthio)propanoic acid;
2-[(4-carboxy)amyloxy]-3-(propylthio)propanoic acid;
2-glycoloyloxy-3-(propylthio)propanoic acid;
2-glutaroyloxy-3-(propylthio)propanoic acid;
2-formylamino-3-(propylthio)propanoic acid;
2-acetylamino-3-(propylthio)propanoic acid;
2-propionylamino-3-(propylthio)propanoic acid;

2-butyrylamino-3-(propylthio)propanoic acid;
2-benzoylamino-3-(propylthio)propanoic acid;
2-lactoylamino-3-(propylthio)propanoic acid;
2-[2-carboxy-2-(hydroxy)propionylamino]-3-(propylthio)propanoic acid;
2-[2-carboxy-1-(hydroxy)propionylamino]-3-(propylthio)propanoic acid;
2-[2-carboxy-1,2-(dihydroxy)propionylamino]-3-(propylthio)propanoic acid;
2-[hydroxy(phenyl)acetyl]amino-3-(propylthio)propanoic acid;
2-[2,3-dicarboxy-2-(hydroxy)butyrylamino]-3-(propylthio)propanoic acid;
2-[2-carboxy-1-carboxymethyl-1-(hydroxy)propionylamino]-3-(propylthio)propanoic acid;
2-(3-carboxyacryloyl)amino-3-(propylthio)propanoic acid;
2-(2,4-pentadienoylamino)-3-(propylthio)propanoic acid;
2-(2-carboxypropionylamino)-3-(propylthio)propanoic acid;
2-[(4-carboxy)amylamino]-3-(propylthio)propanoic acid;
2-glycoloylamino-3-(propylthio)propanoic acid;
2-glutaroylamino-3-(propylthio)propanoic acid;
2-carboxy-3-(butylthio)propanoic acid;
2-acetyloxy-3-(butylthio)propanoic acid;
2-propionyloxy-3-(butylthio)propanoic acid;
2-butyryloxy-3-(butylthio)propanoic acid;
2-benzoyloxy-3-(butylthio)propanoic acid;
2-lactoyloxy-3-(butylthio)propanoic acid;
2-[2-carboxy-2-(hydroxy)propionyloxy]-3-(butylthio)propanoic acid;
2-[2-carboxy-1-(hydroxy)propionyloxy]-3-(butylthio)propanoic acid;
2-[2-carboxy-1,2-(dihydroxy)propionyloxy]-3-(butylthio)propanoic acid;
2-[hydroxy(phenyl)acetyl]oxy-3-(butylthio)propanoic acid;
2-[2,3-dicarboxy-2-(hydroxy)butyryloxy]-3-(butylthio)propanoic acid;
2-[2-carboxy-1-carboxymethyl-1-(hydroxy)propionyloxy]-3-(butylthio)propanoic acid;
2-(3-carboxyacryloyl)oxy-3-(butylthio)propanoic acid;
2-(2,4-pentadienoyloxy)-3-(butylthio)propanoic acid;
2-(2-carboxypropionyloxy)-3-(butylthio)propanoic acid;
2-[(4-carboxy)amyloxy]-3-(butylthio)propanoic acid;
2-glycoloyloxy-3-(butylthio)propanoic acid;
2-glutaroyloxy-3-(butylthio)propanoic acid;
2-formylamino-3-(butylthio)propanoic acid;
2-acetylamino-3-(butylthio)propanoic acid;
2-propionylamino-3-(butylthio)propanoic acid;
2-butyrylamino-3-(butylthio)propanoic acid;
2-benzoylamino-3-(butylthio)propanoic acid;
2-lactoylamino-3-(butylthio)propanoic acid;
2-[2-carboxy-2-(hydroxy)propionylamino]-3-(butylthio)propanoic acid;
2-[2-carboxy-1-(hydroxy)propionylamino]-3-(butylthio)propanoic acid;
2-[2-carboxy-1,2-(dihydroxy)propionylamino]-3-(butylthio)propanoic acid;
2-[hydroxy(phenyl)acetyl]amino-3-(butylthio)propanoic acid;
2-[2,3-dicarboxy-2-(hydroxy)butyrylamino]-3-(butylthio)propanoic acid;
2-[2-carboxy-1-carboxymethyl-1-(hydroxy)propionylamino]-3-(butylthio)propanoic acid;
2-(3-carboxyacryloyl)amino-3-(butylthio)propanoic acid;
2-(2,4-pentadienoylamino)-3-(butylthio)propanoic acid;
2-(2-carboxypropionylamino)-3-(butylthio)propanoic acid;
2-[(4-carboxy)amylamino]-3-(butylthio)propanoic acid;
2-glycoloylamino-3-(butylthio)propanoic acid;
2-glutaroylamino-3-(butylthio)propanoic acid;
2-hydroxy-4-(methylthio)butanoic acid;
2-hydroxy-4-(ethylthio)butanoic acid;
2-hydroxy-4-(propylthio)butanoic acid;
2-hydroxy-4-(butylthio)butanoic acid;
2-amino-4-(methylthio)butanoic acid;
2-amino-4-(ethylthio)butanoic acid;
2-amino-4-(propylthio)butanoic acid;
2-amino-4-(butylthio)butanoic acid;
2-carboxy-4-(methylthio)butanoic acid;
2-acetyloxy-4-(methylthio)butanoic acid;
2-propionyloxy-4-(methylthio)butanoic acid;
2-butyryloxy-4-(methylthio)butanoic acid;
2-benzoyloxy-4-(methylthio)butanoic acid;
2-lactoyloxy-4-(methylthio)butanoic acid;
2-[2-carboxy-2-(hydroxy)propionyloxy]-4-(methylthio)butanoic acid;
2-[2-carboxy-1-(hydroxy)propionyloxy]-4-(methylthio)butanoic acid;
2-[2-carboxy-1,2-(dihydroxy)propionyloxy]-4-(methylthio)butanoic acid;
2-[hydroxy(phenyl)acetyl]oxy-4-(methylthio)butanoic acid;
2-[2,3-dicarboxy-2-(hydroxy)butyryloxy]-4-(methylthio)butanoic acid;
2-[2-carboxy-1-carboxymethyl-1-(hydroxy)propionyloxy]-4-(methylthio)butanoic acid;
2-(3-carboxyacryloyl)oxy-4-(methylthio)butanoic acid;
2-(2,4-pentadienoyloxy)-4-(methylthio)butanoic acid;
2-(2-carboxypropionyloxy)-4-(methylthio)butanoic acid;
2-[(4-carboxy)amyloxy]-4-(methylthio)butanoic acid;
2-glycoloyloxy-4-(methylthio)butanoic acid;
2-glutaroyloxy-4-(methylthio)butanoic acid;
2-formylamino-4-(methylthio)butanoic acid;
2-acetylamino-4-(methylthio)butanoic acid;
2-propionylamino-4-(methylthio)butanoic acid;
2-butyrylamino-4-(methylthio)butanoic acid;
2-benzoylamino-4-(methylthio)butanoic acid;
2-lactoylamino-4-(methylthio)butanoic acid;
2-[2-carboxy-2-(hydroxy)propionylamino]-4-(methylthio)butanoic acid;
2-[2-carboxy-1-(hydroxy)propionylamino]-4-(methylthio)butanoic acid;
2-[2-carboxy-1,2-(dihydroxy)propionylamino]-4-(methylthio)butanoic acid;
2-[hydroxy(phenyl)acetyl]amino-4-(methylthio)butanoic acid;
2-[2,3-dicarboxy-2-(hydroxy)butyrylamino]-4-(methylthio)butanoic acid;
2-[2-carboxy-1-carboxymethyl-1-(hydroxy)propionylamino]-4-(methylthio)butanoic acid;
2-(3-carboxyacryloyl)amino-4-(methylthio)butanoic acid;
2-(2,4-pentadienoylamino)-4-(methylthio)butanoic acid;
2-(2-carboxypropionylamino)-4-(methylthio)butanoic acid;
2-[(4-carboxy)amylamino]-4-(methylthio)butanoic acid;
2-glycoloylamino-4-(methylthio)butanoic acid;
2-glutaroylamino-4-(methylthio)butanoic acid;
2-carboxy-4-(ethylthio)butanoic acid;
2-acetyloxy-4-(ethylthio)butanoic acid;
2-propionyloxy-4-(ethylthio)butanoic acid;
2-butyryloxy-4-(ethylthio)butanoic acid;
2-benzoyloxy-4-(ethylthio)butanoic acid;

2-lactoyloxy-4-(ethylthio)butanoic acid;
2-[2-carboxy-2-(hydroxy)propionyloxy]-4-(ethylthio)butanoic acid;
2-[2-carboxy-1-(hydroxy)propionyloxy]-4-(ethylthio)butanoic acid;
2-[2-carboxy-1,2-(dihydroxy)propionyloxy]-4-(ethylthio)butanoic acid;
2-[hydroxy(phenyl)acetyl]oxy-4-(ethylthio)butanoic acid;
2-[2,3-dicarboxy-2-(hydroxy)butyryloxy]-4-(ethylthio)butanoic acid;
2-[2-carboxy-1-carboxymethyl-1-(hydroxy)propionyloxy]-4-(ethylthio)butanoic acid;
2-(3-carboxyacryloyl)oxy-4-(ethylthio)butanoic acid;
2-(2,4-pentadienoyloxy)-4-(ethylthio)butanoic acid;
2-(2-carboxypropionyloxy)-4-(ethylthio)butanoic acid;
2-[(4-carboxy)amyloxy]-4-(ethylthio)butanoic acid;
2-glycoloyloxy-4-(ethylthio)butanoic acid;
2-glutaroyloxy-4-(ethylthio)butanoic acid;
2-formylamino-4-(ethylthio)butanoic acid;
2-acetylamino-4-(ethylthio)butanoic acid;
2-propionylamino-4-(ethylthio)butanoic acid;
2-butyrylamino-4-(ethylthio)butanoic acid;
2-benzoylamino-4-(ethylthio)butanoic acid;
2-lactoylamino-4-(ethylthio)butanoic acid;
2-[2-carboxy-2-(hydroxy)propionylamino]-4-(ethylthio)butanoic acid;
2-[2-carboxy-1-(hydroxy)propionylamino]-4-(ethylthio)butanoic acid;
2-[2-carboxy-1,2-(dihydroxy)propionylamino]-4-(ethylthio)butanoic acid;
2-[hydroxy(phenyl)acetyl]amino-4-(ethylthio)butanoic acid;
2-[2,3-dicarboxy-2-(hydroxy)butyrylamino]-4-(ethylthio)butanoic acid;
2-[2-carboxy-1-carboxymethyl-1-(hydroxy)propionylamino]-4-(ethylthio)butanoic acid;
2-(3-carboxyacryloyl)amino-4-(ethylthio)butanoic acid;
2-(2,4-pentadienoylamino)-4-(ethylthio)butanoic acid;
2-(2-carboxypropionylamino)-4-(ethylthio)butanoic acid;
2-[(4-carboxy)amylamino]-4-(ethylthio)butanoic acid;
2-glycoloylamino-4-(ethylthio)butanoic acid;
2-glutaroylamino-4-(ethylthio)butanoic acid;
2-carboxy-4-(propylthio)butanoic acid;
2-acetyloxy-4-(propylthio)butanoic acid;
2-propionyloxy-4-(propylthio)butanoic acid;
2-butyryloxy-4-(propylthio)butanoic acid;
2-benzoyloxy-4-(propylthio)butanoic acid;
2-lactoyloxy-4-(propylthio)butanoic acid;
2-[2-carboxy-2-(hydroxy)propionyloxy]-4-(propylthio)butanoic acid;
2-[2-carboxy-1-(hydroxy)propionyloxy]-4-(propylthio)butanoic acid;
2-[2-carboxy-1,2-(dihydroxy)propionyloxy]-4-(propylthio)butanoic acid;
2-[hydroxy(phenyl)acetyl]oxy-4-(propylthio)butanoic acid;
2-[2,3-dicarboxy-2-(hydroxy)butyryloxy]-4-(propylthio)butanoic acid;
2-[2-carboxy-1-carboxymethyl-1-(hydroxy)propionyloxy]-4-(propylthio)butanoic acid;
2-(3-carboxyacryloyl)oxy-4-(propylthio)butanoic acid;
2-(2,4-pentadienoyloxy)-4-(propylthio)butanoic acid;
2-(2-carboxypropionyloxy)-4-(propylthio)butanoic acid;
2-[(4-carboxy)amyloxy]-4-(propylthio)butanoic acid;
2-glycoloyloxy-4-(propylthio)butanoic acid;
2-glutaroyloxy-4-(propylthio)butanoic acid;
2-formylamino-4-(propylthio)butanoic acid;
2-acetylamino-4-(propylthio)butanoic acid;
2-propionylamino-4-(propylthio)butanoic acid;
2-butyrylamino-4-(propylthio)butanoic acid;
2-benzoylamino-4-(propylthio)butanoic acid;
2-lactoylamino-4-(propylthio)butanoic acid;
2-[2-carboxy-2-(hydroxy)propionylamino]-4-(propylthio)butanoic acid;
2-[2-carboxy-1-(hydroxy)propionylamino]-4-(propylthio)butanoic acid;
2-[2-carboxy-1,2-(dihydroxy)propionylamino]-4-(propylthio)butanoic acid;
2-[hydroxy(phenyl)acetyl]amino-4-(propylthio)butanoic acid;
2-[2,3-dicarboxy-2-(hydroxy)butyrylamino]-4-(propylthio)butanoic acid;
2-[2-carboxy-1-carboxymethyl-1-(hydroxy)propionylamino]-4-(propylthio)butanoic acid;
2-(3-carboxyacryloyl)amino-4-(propylthio)butanoic acid;
2-(2,4-pentadienoylamino)-4-(propylthio)butanoic acid;
2-(2-carboxypropionylamino)-4-(propylthio)butanoic acid;
2-[(4-carboxy)amylamino]-4-(propylthio)butanoic acid;
2-glycoloylamino-4-(propylthio)butanoic acid;
2-glutaroylamino-4-(propylthio)butanoic acid;
2-carboxy-4-(butylthio)butanoic acid;
2-acetyloxy-4-(butylthio)butanoic acid;
2-propionyloxy-4-(butylthio)butanoic acid;
2-butyryloxy-4-(butylthio)butanoic acid;
2-benzoyloxy-4-(butylthio)butanoic acid;
2-lactoyloxy-4-(butylthio)butanoic acid;
2-[2-carboxy-2-(hydroxy)propionyloxy]-4-(butylthio)butanoic acid;
2-[2-carboxy-1-(hydroxy)propionyloxy]-4-(butylthio)butanoic acid;
2-[2-carboxy-1,2-(dihydroxy)propionyloxy]-4-(butylthio)butanoic acid;
2-[hydroxy(phenyl)acetyl]oxy-4-(butylthio)butanoic acid;
2-[2,3-dicarboxy-2-(hydroxy)butyryloxy]-4-(butylthio)butanoic acid;
2-[2-carboxy-1-carboxymethyl-1-(hydroxy)propionyloxy]-4-(butylthio)butanoic acid;
2-(3-carboxyacryloyl)oxy-4-(butylthio)butanoic acid;
2-(2,4-pentadienoyloxy)-4-(butylthio)butanoic acid;
2-(2-carboxypropionyloxy)-4-(butylthio)butanoic acid;
2-[(4-carboxy)amyloxy]-4-(butylthio)butanoic acid;
2-glycoloyloxy-4-(butylthio)butanoic acid;
2-glutaroyloxy-4-(butylthio)butanoic acid;
2-formylamino-4-(butylthio)butanoic acid;
2-acetylamino-4-(butylthio)butanoic acid;
2-propionylamino-4-(butylthio)butanoic acid;
2-butyrylamino-4-(butylthio)butanoic acid;
2-benzoylamino-4-(butylthio)butanoic acid;
2-lactoylamino-4-(butylthio)butanoic acid;
2-[2-carboxy-2-(hydroxy)propionylamino]-4-(butylthio)butanoic acid;
2-[2-carboxy-1-(hydroxy)propionylamino]-4-(butylthio)butanoic acid;
2-[2-carboxy-1,2-(dihydroxy)propionylamino]-4-(butylthio)butanoic acid;
2-[hydroxy(phenyl)acetyl]amino-4-(butylthio)butanoic acid;
2-[2,3-dicarboxy-2-(hydroxy)butyrylamino]-4-(butylthio)butanoic acid;
2-[2-carboxy-1-carboxymethyl-1-(hydroxy)propionylamino]-4-(butylthio)butanoic acid;
2-(3-carboxyacryloyl)amino-4-(butylthio)butanoic acid;

2-(2,4-pentadienoylamino)-4-(butylthio)butanoic acid;
2-(2-carboxypropionylamino)-4-(butylthio)butanoic acid;
2-[(4-carboxy)amylamino]-4-(butylthio)butanoic acid;
2-glycoloylamino-4-(butylthio)butanoic acid; and
2-glutaroylamino-4-(butylthio)butanoic acid.

In a more preferred embodiment, the compound of Formula I is selected from the group of compounds wherein $R^1$ is methyl; n is 2; $R^2$ is hydroxy or —$OCOR^3$; and $R^3$ is a derivative of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, or glutaric acid. In an even more preferred embodiment, the compound of Formula I is selected from the group of compounds wherein $R^1$ is methyl; n is 2; $R^2$ is hydroxy or —$OCOR^3$; and $R^3$ is a derivative of formic acid, propionic acid, butyric acid, lactic acid, citric acid, or fumaric acid.

Representative salts of the compound of Formula I include the ammonium, magnesium, calcium, lithium, sodium, potassium, selenium, iron, copper, and zinc salts. In a preferred embodiment, the compound of Formula I is in the form of the calcium salt. Representative amides include methylamide, dimethylamide, ethylmethylamide, butylamide, dibutylamide, butylmethylamide, alkyl ester of N-acyl methionates (e.g., alkyl N-acetyl methionates. Representative esters include the methyl, ethyl, n-propyl, isopropyl, butyl esters, namely n-butyl, sec-butyl, isobutyl, and t-butyl esters, pentyl esters and hexyl esters, especially n-pentyl, isopentyl, n-hexyl and isohexyl esters.

In various preferred embodiments, the compound of Formula I is 2-hydroxy-4-(methylthio)butanoic acid (HMBA) or a salt, amide or ester thereof. In still more preferred embodiments, the compound of Formula I is HMBA.

In the novel method of enhancing palatability of feed for aquaculture and methods of feeding fish, the concentration of the compound of formula I in the feed is typically from about 0.005 wt. % to about 0.5 wt. % based on the total weight of the feed composition; preferably, the concentration of the compound of formula I is from about 0.01 wt. % to about 0.1 wt. %; more preferably, from about 0.01 wt. % to about 0.08 wt. %; even more preferably, from about 0.01 wt. % to less than 0.05 wt. %; most preferably, from about 0.01 wt. % to about 0.048 wt. %; most preferably, from about 0.01 wt. % to about 0.040 wt. %.

The additive of Formula I is typically incorporated into an aquaculture feed comprising between about 20% and about 50% by weight animal and/or vegetable protein, between about 1% and about 15% by weight CF (ether extract) or EE, between about 1500 and 4500 kcal/kg of energy and between about 5% and bout 20% by weight moisture. Preferably, the additive of Formula I is typically incorporated into an aquaculture feed comprising between about 27% and about 45% by weight animal and/or vegetable protein, between about 3% and about 10% by weight CF (ether extract) or EE, between about 1750 and 3800 kcal/kg of energy and between about 8% and bout 16% by weight moisture. More preferably, the additive of Formula I is typically incorporated into an aquaculture feed comprising between about 34% and about 38% by weight animal and/or vegetable protein, between about 5% and about 8% by weight CF (ether extract) or EE, between about 2500 and 3000 kcal/kg of energy and between about 11% and bout 13% by weight moisture. CF(ether extract) or EE represent the wt. % of fat soluble lipids in the feed.

Preferably, the fat and protein are primarily of vegetable origin. For example, the feed formulation may more preferably comprise between about 20% and about 50% by weight vegetable protein, up to about 50% by weight animal protein, preferably between about 30% and about 40% by weight vegetable protein, and up to about 5% by weight animal protein. Useful sources of vegetable protein are known by one skilled in the art and include soybean meal, soybean hulls, soybean oil, cottonseed meal, cottonseed hulls, canola meal, sunflower meal, and linseed meal. Useful feed components of animal origin are known by one skilled in the art and include meat meal, bone meal and fish meal. For example, the feed formulation may consist essentially of meal produced from vegetable grains; or may, for example, comprise up to about 50% by weight fish meal or other animal feed source, the balance essentially vegetable meal except for the palatability enhancing component and various vitamins, minerals and other minor ingredients of a conventional nature.

In various preferred embodiments, for the methods of enhancing palatability of feed for aquaculture and feeding fish a fish food, the compound of formula I comprises 2-hydroxy-4-(methylthio)butanoic acid (HMTBA) or a salt, ester or amide thereof and the concentration of the HMTBA or a salt, ester or amide thereof is from about 0.001 wt. % to about 0.5 wt. %; more preferably, from about 0.001 wt. % to about 0.1 wt. %; even more preferably, from about 0.001 wt. % to less than 0.05 wt. %; most preferably, from about 0.01 wt. % to about 0.048 wt. %; most preferably, from about 0.01 wt. % to about 0.040 wt. %.

The fish food compositions can be typically prepared having the above described components and be formulated to have favorable disintegration properties. Preferably, the density of the fish food form (e.g., pellets, balls, flakes) is appropriate to provide a food that is accessible to the fish and does not quickly sink to the bottom of the pond or other enclosure and be lost as feed to the fish. In addition, the fish food form should be of a hardness that maximizes the attractiveness of the food to the fish, while minimizing the disintegration of the food form and premature dispersal and loss of food to the feeding population. Accordingly, a person of skill in the art would know how to select fish food components to impart the properties described above.

In applications other than enhanced palatability aqualculture feeds, the concentration of the compound of Formula I in the feed compositions described herein is between about 0.01% and about 5%. In various preferred embodiments, the concentration is between 0.01% and about 4%; between 0.02% and about 3%; between 0.03% and about 2%; between 0.04% and about 1%; between about 0.05% and about 0.6%; and between about 0.06% and about 0.525%. In various particularly preferred embodiments, the concentration is about 0.075%; about 0.125%; about 0.15%; about 0.225%; about 0.25%; about 0.3%; about 0.375%; and about 0.5%.

In various embodiments of the present invention, the methods of inhibiting microbes in animal feed comprises treating said feed with a compound of Formula I and one or more organic acids. Preferably, the organic acid has a $pK_a<5.5$. In many embodiments, the organic acid comprises a carboxyl-substituted hydrocarbon moiety. The hydrocarbon moiety may be further substituted by one or more substituents such as halogen; oxygen-containing groups such as alkoxy, aryloxy, hydroxy, protected hydroxy, keto, acyl, acyloxy; nitrogen-containing groups such as nitro, amino, amido, cyano; and sulfur-containing groups such as thiol, thioalkyl, and sulfonyl. In a preferred embodiment, said organic acids are selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid, or combinations thereof. In one embodiment, the organic acid is formic acid, propionic acid, butyric acid, lactic acid, or combinations thereof.

Preferably, for antimicrobial compositions, the combined concentration of the compound of Formula I and the organic acid or mixture of organic acids in the food compositions described herein is between about 0.01% and about 5%. In various preferred embodiments, the combined concentration is between about 0.015% and about 4%; between about 0.02% and about 3%; between about 0.05% and about 2.5%; between about 0.075% and about 2%; between about 0.1% and about 1.5%; between about 0.15% and about 1%; between about 0.4% and about 0.9%; between about 0.5% and about 0.8%; between about 0.01% and about 5%; between about 0.01% and about 4.5%; between about 0.05% and about 4%; between about 0.08% and about 3%; between about 0.1% and about 2.5%; between about 0.01% and about 0.8%; between about 0.01% and about 0.5%; between about 0.05% and about 0.6%; and between about 0.06% and about 0.525%.

In various other preferred embodiments, the concentration of said compound of Formula I and said organic acid in the food compositions described herein is as follows:

| Concentration of the compound of Formula I | Concentration of the organic acid |
|---|---|
| between about 0.01% and about 0.5% | between about 0.01% and about 0.5% |
| between about 0.1% and about 0.4% | between about 0.1% and about 0.5% |
| about 0.125% | about 0.375% |
| about 0.225% | about 0.225% |
| about 0.25% | about 0.25% |
| about 0.375% | about 0.125% |
| about 0.3% | about 0.5% |

In a preferred embodiment of the present invention, the antimicrobial compositions comprises a compound of Formula I and one or more other acidulants. Such acidulants are typically strong acids, and are preferably mineral acids. Examples of such acidulants include phosphoric acid, phosphorous acid, sulfuric acid, hydrochloric acid, hydrobromic acid, and nitric acid. In one embodiment, the acidulant is phosphoric acid.

In a more preferred embodiment, the antimicrobial compositions comprise a compound of Formula I, one or more organic acids, as defined above, and one or more other acidulants as defined above.

Preferably, the pH of the feed is between about 3 and about 8. Even more preferably, the pH is between about 4 and about 7. Still more preferably, the pH is between about 4.5 and about 6.75. The pH may be measured by placing a known quantity of the feed and placing it in a known quantity of distilled water. The pH of the resulting solution, after sitting, may be measured by any standard means for measuring pH.

The following embodiments are particularly preferred for the addition of combinations of an 88 wt. % 88 wt. % 2-hydroxy-4-methylthiobutanoic acid (sold under the tradename Alimet®) and formic acid to feed (concentrations expressed in wt % of feed composition):

about 0.125% Alimet® and about 0.375% formic acid at pH from about 4.5 to about 6.75;

about 0.25% Alimet® and about 0.25% formic acid at pH from about 4.5 to about 6.75;

about 0.375% Alimet® and about 0.125% formic acid at pH from about 4.5 to about 6.75;

about 0.5% Alimet® at pH from about 4.5 to about 6.75;

about 0.3% Alimet® and about 0.5% formic acid at pH from about 4.5 to about 6.75.

In another preferred embodiment, the above-mentioned organic acid is a mixture of formic acid and propionic acid, wherein the formic acid comprises from about 95% to about 5% of the organic acid mixture and the propionic acid comprises from about 5% to about 95% of the organic mixture. Preferably, formic acid comprises from about 85% to about 15% of the organic acid mixture, and propionic acid comprises from about 15% to about 85% of the organic acid mixture. In another preferred embodiment, formic acid comprises from about 85% to about 65% of the organic acid mixture, and propionic acid comprises from about 15% to 35% of the organic acid mixture. In another preferred embodiment, formic acid comprises about 75% of the organic acid mixture, and propionic acid comprises about 25% of the organic acid mixture. This formic/propionic acid mixture can then be combined with the compound of Formula I according to the ratios described above.

In a preferred embodiment, the antimicrobial compositions comprise a compound of Formula I, preferably HMBA or a salt thereof, and a first organic acid, as defined herein. Preferably, the first organic acid is selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid. In another preferred embodiment, the antimicrobial compositions may further comprise one or more components selected from: a second organic acid, a third organic acid, and an acidulant. Preferably, the second organic acid and third organic acid are independently selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid. Preferably, the acidulant is selected from the group consisting of phosphoric acid, sulfuric acid, phosphorous acid, hydrochloric acid, hydrobromic acid, and nitric acid.

It has been discovered that certain antimicrobial compositions of the invention have an improved odor, when the compound of Formula I is Alimet®, compared to similar compositions without Alimet®. For example, blends comprising formic acid have a pungent odor. In such blends without Alimet®, this odor is more readily detectable than in the same blends containing Alimet®. Without being limited to a particular theory, it is believed that the Alimet® in the blends may lower the vapor pressure of the other organic acids in the blends. Alternatively, the Alimet® may mask the disagreeable odors.

In another preferred embodiment is provided a method for inhibiting bacteria in silage, said method comprising treating said silage with an anti-bacterial composition comprising a compound of Formula I. Preferably, the compound of Formula I is added to the silage at about 1 lb/ton to 80 lb/ton of fresh forage, more preferably at about 2 lb/ton to 50 lb/ton of fresh forage, more preferably about 3 lb/ton to 45 lb/ton of fresh forage, more preferably about 4 lb/ton to 40 lb/ton of fresh forage, more preferably about 5 lb/ton to 35 lb/ton of fresh forage, more preferably about 7 lb/ton to 30 lb/ton of fresh forage, more preferably about 9 lb/ton to 25 lb/ton of fresh forage, more preferably about 10 lb/ton to 20 lb/ton of fresh forage. Optionally, the compositions may further comprise an acidulant, as described herein.

In another preferred embodiment is provided a method for inhibiting bacteria in silage, said method comprising treating said silage with an anti-bacterial composition comprising a compound of Formula I and one or more organic acids as described above. Preferably, the compound of Formula I and other organic acid(s) are added to the silage at about 2 lb/ton to 125 lb/ton of fresh forage combined. In one embodiment, the compound of Formula I and other organic acid(s) are added to the silage at about 4 lb/ton to 100 lb/ton of fresh forage combined. In another embodiment, the compound of Formula I and other organic acid(s) are added to the silage at about 5 lb/ton to 90 lb/ton of fresh forage combined, more preferably about 7 lb/ton to 80 lb/ton of fresh forage combined, more preferably about 8 lb/ton to 70 lb/ton of fresh forage combined, more preferably about 9 lb/ton to 60 lb/ton of fresh forage combined, more preferably about 10 lb/ton to 55 lb/ton of fresh forage combined, more preferably about 12 lb/ton to 50 lb/ton of fresh forage combined, more preferably about 15 lb/ton to 30 lb/ton of fresh forage combined. Optionally, the compositions may further comprise an acidulant, as described herein.

In a preferred embodiment of the invention, the bacteria inhibited according to the methods of the present invention is from the family Enterobacteriaceae, *Campylobacter* or *Lactobacillaceae*. In another preferred embodiment, the bacteria is from the family *Campylobacter* or *Lactobacillaceae*. In another preferred embodiment, the bacteria is from the genus *Lactobacillus* or *Campylobacter*. In another preferred embodiment, the bacteria is *L. plantarum* or *C. jejuni*. In a particularly preferred embodiment, the bacteria is from the family Enterobacteriaceae. In an even more preferred embodiment, the bacteria is from the genus *Salmonella* or *Escherichia*. In a still more preferred embodiment, the bacteria is *S. enteritidis* or *E. coli*.

In yet another embodiment of the present invention, the above-mentioned compounds of Formula I may be used in the manufacture of a nutrient composition for inhibiting bacteria in animal feed. These nutrient compositions may further comprise one or more organic acids, as described above. Optionally, the compositions may further comprise an acidulant, as described herein.

In still yet another embodiment of the present invention, the above-mentioned compounds of Formula I may be used in a method for inhibiting bacteria in animal feed comprising computing the concentration in said feed of said compound of Formula I necessary to inhibit bacteria present in said animal feed, and applying said compound of Formula I to said feed in an amount sufficient to achieve said concentration.

In another embodiment of the present invention, the above-mentioned compounds of Formula I and above-mentioned organic acids may be used in a method of inhibiting bacteria in animal feed comprising computing the concentration in said feed of a compound of Formula I and another organic acid or mixture of organic acids necessary to inhibit bacteria present in said animal feed, and applying said compound of Formula I and said organic acid or mixture of organic acids to said feed in an amount sufficient to achieve said concentration.

In still yet another embodiment of the present invention, the above-mentioned compounds of Formula I may be used in a method of method for inhibiting mold in animal feed comprising directly or indirectly making information available for computing the concentration in said feed of a compound of Formula I necessary to inhibit bacteria present in said animal feed, and directly or indirectly making information available for applying said compound of Formula I to said feed in an amount sufficient to achieve said concentration.

In another embodiment of the present invention, the above-mentioned compounds of Formula I and above-mentioned organic acids may be used in a method of method for inhibiting mold in animal feed comprising directly or indirectly making information available for computing the concentration in said feed of said compound of Formula I and said organic acid or mixture of organic acids necessary to inhibit bacteria present in said animal feed, and directly or indirectly making information available for applying said compound of Formula I and said organic acid or mixture of organic acids to said feed in an amount sufficient to achieve said concentration.

In another embodiment of the present invention, the above-mentioned animal feeds may be heat-treated, either before or after administration of the above-mentioned compounds of Formula I and/or organic acids.

In yet another embodiment of the present invention, the above-mentioned compounds of Formula I may be used in a method of inhibiting bacteria in animal feed, the method comprising monitoring the concentration of methionine supplement in said feed composition, adding additional amounts of said methionine supplement as needed to achieve an anti-bacterially effective concentration of methionine supplement in said feed composition.

Treatment of the animal feed compositions with the compounds of Formula I and with the other organic acids disclosed herein may be done by mixing the compound of Formula I (and other organic acid, if present) with the other ingredients in the feed, such as the corn, soybean meal, meat meal premix, other feed supplements, etc., as the feed is being formulated. Alternatively, the compound of Formula I and optional other organic acid(s) may be applied to a pre-mixed or pre-pelleted feed. In either case, the compound of Formula I and optional organic acid(s) are preferably added as liquids, and uniformly disperse throughout the bulk of the feed composition when applied. When the compound of Formula I and another organic acid are both used in the methods of the present invention, preferably said compound of Formula I and said other organic acid or acids are mixed together before application to the animal feeds. This pre-mixed compound of Formula I/organic acid(s) blend can be applied to the animal feed ingredients during formulation of the feed compositions, or can be applied to pre-mixed or pre-pelleted feed.

In one embodiment of the present invention is presented a method of inhibiting mold in an animal feed composition, the method comprising applying a compound of Formula I to said feed composition, wherein said feed composition comprises corn and soy.

In another embodiment of the present invention, the methods of inhibiting mold in animal feed comprises treating said feed with an antifungally-effective amount of a compound of Formula I and one or more organic acids as described above.

In another preferred embodiment, the above-mentioned organic acid is a mixture of formic acid and propionic acid, wherein the formic acid comprises from about 95% to about 5% of the organic acid mixture and the propionic acid comprises from about 5% to about 95% of the organic mixture. Preferably, formic acid comprises from about 85% to about 15% of the organic acid mixture, and propionic acid comprises from about 15% to about 85% of the organic acid mixture. In another preferred embodiment, formic acid comprises from about 85% to about 65% of the organic acid mixture, and propionic acid comprises from about 15% to 35% of the organic acid mixture. This organic acid mixture can then be combined with the compound of Formula I according to the ratios described above.

In another embodiment of the present invention is presented a method of inhibiting mold in an animal feed composition, the method comprising applying a compound of Formula I and one or more organic acids to said feed composition, wherein said feed composition comprises corn and soy. In one embodiment, said organic acid is selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid, or combinations thereof. In another embodiment, the organic acid is formic acid, propionic acid, or combinations thereof.

In yet another embodiment of the present invention, the above-mentioned compounds of Formula I may be used in a method for delaying the formation of mold in an animal feed composition, the method comprising applying a compound of Formula I to said feed composition, wherein said feed composition comprises corn and soy.

In yet another embodiment of the present invention, the above-mentioned compounds of Formula I and above-mentioned organic acids may be used in a method for delaying the formation of mold in an animal feed composition, the method comprising applying a compound of Formula I and one or more organic acids to said feed composition, wherein said feed composition comprises corn and soy.

In yet another embodiment of the present invention, the above-mentioned compounds of Formula I may be used in a method of inhibiting the formation of mold in an animal feed composition, the method comprising applying a compound of Formula I to said feed composition, wherein said feed composition has a moisture content of abut 17% or less. Preferably, the moisture content is at least 0.01%. In another embodiment, the moisture content is at least 1%. In another embodiment, the moisture content is at least 5%. In another embodiment, the moisture content is at least 10%.

In yet another embodiment of the present invention, the above-mentioned compounds of Formula I and above-mentioned organic acids may be used in a method of inhibiting the formation of mold in an animal feed composition, the method comprising applying a compound of Formula I and one or more organic acids to said feed composition, wherein said feed composition has a moisture content of about 17% or less. Preferably, the moisture content is at least 0.01%. In another embodiment, the moisture content is at least 1%. In another embodiment, the moisture content is at least 5%. In another embodiment, the moisture content is at least 10%.

In yet another embodiment of the present invention is provided a method for inhibiting mold in silage, said method comprising treating said silage with an anti-fungal composition comprising a compound of Formula I. Preferably, the compound of Formula I is added to the silage at about 1 lb/ton to 40 lb/ton of fresh forage, more preferably about 5 lb/ton to 30 lb/ton of fresh forage, more preferably about 7 lb/ton to 25 lb/ton of fresh forage, more preferably about 10 lb/ton to 20 lb/ton of fresh forage.

In yet another embodiment of the present invention is provided a method for inhibiting mold in silage, said method comprising treating said silage with an anti-fungal composition comprising a compound of Formula I and one or more organic acids. Preferably, the compound of Formula I and other organic acid(s) are added to the silage at about 5 lb/ton to 50 lb/ton of fresh forage combined, more preferably about 8 lb/ton to 40 lb/ton of fresh forage combined, more preferably about 10 lb/ton to 30 lb/ton of fresh forage combined, more preferably about 15 lb/ton to 25 lb/ton of fresh forage combined.

In yet another embodiment of the present invention, the above-mentioned compounds of Formula I may be used in a method for inhibiting the growth of mold in an animal feed composition, the method comprising computing the concentration in said feed of a compound of Formula I necessary to inhibit the growth of mold in said feed composition; and applying said compound of Formula I to said feed composition in said concentration.

In yet another embodiment of the present invention, the above-mentioned compounds of Formula I and organic acids may be used in a method for inhibiting the growth of mold in an animal feed composition, the method comprising computing the concentration in said feed of a compound of Formula I and another organic acid or mixture of organic acids necessary to inhibit the growth of mold in said feed composition; and applying said compound of Formula I and said organic acid or mixture of organic acids to said feed composition in said concentration.

In yet another embodiment of the present invention, the above-mentioned compounds of Formula I may be used in a method for inhibiting the growth of mold in animal feed comprising computing the concentration in said feed of a compound of Formula I necessary to inhibit the growth of mold in said animal feed; and applying said compound of Formula I to said feed in said concentration.

In yet another embodiment of the present invention, the above-mentioned compounds of Formula I and organic acids may be used in a method for inhibiting the growth of mold in animal feed comprising computing the concentration in said feed of a compound of Formula I and another organic acid or mixture of organic acids necessary to inhibit the growth of mold in said animal feed; and applying said compound of Formula I and said organic acid or mixture of organic acids to said feed in said concentration.

In yet another embodiment of the present invention, the above-mentioned compounds of Formula I may be used in a method for improving the mold resistance of an animal feed composition, the method comprising discontinuing the use of DL-methionine as a feed supplement; computing the concentration in said feed of a compound of Formula I necessary to inhibit the growth of mold in said animal feed; and applying said compound of Formula I to said feed in said concentration.

In yet another embodiment of the present invention, the above-mentioned compounds of Formula I and said organic acids may be used in a method for improving the mold resistance of an animal feed composition, the method comprising discontinuing the use of DL-methionine as a feed supplement; computing the concentration in said feed of a compound of Formula I and another organic acid or mixture of organic acids necessary to inhibit the growth of mold in said animal feed; and applying said compound of Formula I and said organic acid or mixture of organic acids to said feed in said concentration.

In yet another embodiment of the present invention, the above-mentioned compounds of Formula I may be used in a method for inhibiting mold in animal feed directly or indirectly making information available for computing the concentration in said feed of said compound of Formula I necessary to inhibit mold present in said animal feed; and directly or indirectly making information available for applying said compound of Formula I to said feed in said concentration.

In yet another embodiment of the present invention, the above-mentioned compounds of Formula I and organic acids may be used in a method for inhibiting mold in animal feed directly or indirectly making information available for computing the concentration in said feed of said compound of Formula I and the concentration of said organic acid or mixture of organic acids necessary to inhibit mold present in said animal feed; and directly or indirectly making information available for applying said compound of Formula I and said organic acid or mixture of organic acids to said feed in said concentration.

In yet another embodiment of the present invention, the above-mentioned compounds of Formula I may be used in the manufacture of a nutrient composition for inhibiting mold in animal feed by treating said feed with said nutrient composition in an anti-mold effective amount. In another embodiment, the nutrient composition may also comprise one or more of the above-mentioned organic acids, or a mixture thereof.

In yet another embodiment of the present invention, the above-mentioned compounds of Formula I may be used in a method of inhibiting mold in an animal feed composition, the method comprising monitoring the concentration of methionine supplement in said feed composition, adding additional amounts of said methionine supplement as needed to achieve an anti-mold effective concentration of methionine supplement in said feed composition.

In yet another embodiment of the present invention, the above-mentioned compounds of Formula I may be used in a method of enhancing the palatability of animal food, the method comprising treating the food with a compound of Formula I in an amount sufficient to give a concentration of the compound of Formula I in the food of between about 0.01 wt. % and about 0.5 wt. %. Preferably, the food is food for canines or felines. For dogs, the concentration of the compound of Formula I in the food is preferably between about 0.05% and about 0.15%; for cats, it is preferably between about 0.20% and 0.30%. For both dogs and cats, the compound of Formula I is preferably HMBA or DLM.

In a preferred embodiment, the compositions or combinations described herein comprise HMBA, or a salt, ester or amide thereof; and a first organic acid selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid. Even more preferably, the first organic acid is selected from the group consisting of formic acid, propionic acid, butyric acid, and lactic acid.

In various preferred embodiments, the compositions or combinations further comprise an acidulant selected from the group consisting of mineral acids, preferably selected from the group consisting of phosphoric acid, sulfuric acid, phosphorous acid, hydrochloric acid, hydrobromic acid, and nitric acid; a second organic acid selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid. In even more preferred embodiments, the first organic acid and second organic acid are independently selected from the group consisting of formic acid, propionic acid, butyric acid, and lactic acid; and/or a third organic acid selected from the group consisting of formic acid, acetic acid, propionic acid, butyric acid, benzoic acid, lactic acid, malic acid, tartaric acid, mandelic acid, citric acid, fumaric acid, sorbic acid, boric acid, succinic acid, adipic acid, glycolic acid, and glutaric acid.

In a still more preferred embodiment, the compositions and combinations described herein comprise HMBA, formic acid, propionic acid, and phosphoric acid. Preferably, the content of HMBA is from about 5% to about 20% of the sum of the HMBA, formic acid, propionic acid, and phosphoric acid content; the content of the formic acid is from about 65% to about 85% of said sum; the content of the propionic acid is from about 1% to about 15% of said sum; and the content of the phosphoric acid is from about 5% to about 20% of said sum. Even more preferably, the content of HMBA is about 10% of said sum; the content of the formic acid is about 75% of said sum; the content of the propionic acid is about 5% of said sum; and the content of the phosphoric acid is about 10% of said sum. Alternatively, the content of HMBA is from about 20% to about 40% of said sum, the content of the formic acid is from about 45% to about 65% of said sum, the content of the propionic acid is from about 1% to about 20% of said sum, and the content of the phosphoric acid is from about 1% to about 15% of said sum; even more preferably, the content of HMBA is about 30% of said sum, the content of the formic acid is about 55% of said sum, the content of the propionic acid is about 10% of said sum, and the content of the phosphoric acid is about 5% of said sum.

In another more preferred embodiment, the compositions and combinations described herein comprise HMBA, butyric acid, lactic acid, and phosphoric acid. Preferably, the content of HMBA is from about 20% to about 40% of the sum of the HMBA, butyric acid, lactic acid, and phosphoric acid content; the content of the butyric acid is from about 10% to about 30% of said sum; the content of the lactic acid is from about 10% to about 30% of said sum; and the content of the phosphoric acid is from about 20% to about 40% of said sum. Even more preferably, the content of HMBA is about 30% of said sum; the content of the butyric acid is about 20% of said sum; the content of the lactic acid is about 20% of said sum; and the content of the phosphoric acid is about 30% of said sum. Alternatively, the content of HMBA is from about 20% to about 40% of said sum of the 2-hydroxy-4-(methylthio)butanoic acid, butyric acid, lactic acid, and phosphoric acid content, the content of the butyric acid is from about 5% to about 25% of said sum, the content of the lactic acid is from about 10% to about 30% of said sum, and the content of the phosphoric acid is from about 25% to about 45% of said sum; more preferably, the content of HMBA is about 30% of said sum, the content of the butyric acid is about 15% of said sum, the content of the lactic acid is about 20% of said sum, and the content of the phosphoric acid is about 35% of said sum.

In yet another more preferred embodiment, the compositions and combinations described herein comprise HMBA, butyric acid, formic acid, lactic acid, and phosphoric acid. Preferably, the content of HMBA is from about 10% to about 30% of the sum of the HMBA, butyric acid, formic acid, lactic acid, and phosphoric acid content; the content of the butyric acid is from about 2% to about 22% of said sum; the content of the formic acid is from about 20% to about 40% of said sum; the content of the lactic acid is from about 8% to about 28% of said sum; and the content of the phosphoric acid is from about 10% to about 30% of said sum. Even more preferably, the content of HMBA is about 20% of said sum; the content of the butyric acid is about 12% of said sum; the content of the formic acid is about 30% of said sum; the content of the lactic acid is about 18% of said sum; and the content of the phosphoric acid is about 20% of said sum.

In yet another more preferred embodiment, the compositions and combinations described herein comprise HMBA, butyric acid, lactic acid, propionic acid, and phosphoric acid. Preferably, the content of HMBA is from about 10% to about 30% of the sum of the HMBA, butyric acid, lactic acid, propionic acid, and phosphoric acid content; the content of the butyric acid is from about 2% to about 22% of said sum; the content of the lactic acid is from about 8% to about 28% of said sum; the content of the propionic acid is from about 20% to about 40% of said sum; and the content of the phosphoric acid is from about 10% to about 30% of said sum. Even more preferably, the content of HMBA is about 20% of said sum; the content of the butyric acid is about 12% of said sum; the content of the lactic acid is about 18% of said sum; the content of the propionic acid is about 30% of said sum; and the content of the phosphoric acid is about 20% of said sum.

In yet another more preferred embodiment, the compositions and combinations described herein comprise HMBA, butyric acid, formic acid, propionic acid, and phosphoric acid. Preferably, the content of HMBA is from about 1% to about 20% of the sum of the HMBA, butyric acid, formic acid, propionic acid, and phosphoric acid content; the content of the butyric acid is from about 1% to about 15% of said sum; the content of the formic acid is from about 65% to about 85% of said sum; the content of the propionic acid is from about 1% to about 15% of said sum; and the content of the phosphoric acid is from about 1% to about 15% of said sum. Even more preferably, the content of HMBA is about 10% of said sum; the content of the butyric acid is about 5% of said sum; the content of the formic acid is about 75% of said sum; the content of the propionic acid is about 5% of said sum; and the content of the phosphoric acid is about 5% of said sum.

In yet another more preferred embodiment, the compositions and combinations described herein comprise HMBA, formic acid, and propionic acid. Preferably, the content of HMBA is from about 20% to about 40% of the sum of the HMBA, formic acid, and propionic acid content; the content of the formic acid is from about 40% to about 60% of said sum; and the content of the propionic acid is from about 10% to about 30% of said sum. Even more preferably, the content of HMBA is about 30% of said sum; the content of the formic acid is about 50% of said sum; and the content of the propionic acid is about 20% of said sum.

In yet another more preferred embodiment, compositions and combinations described herein comprise HMBA and phosphoric acid. Preferably, the content of the HMBA is from about 5% to about 50% of the sum of the HMBA and phosphoric acid content. In various more preferred embodiments, the content of the HMBA is about 5%, or about 10%, or about 15%, or about 20%, or about 25%, or about 30%, or about 35%, or about 40%, or about 45%, or about 50% of said sum.

In another embodiment of the present invention is provided an animal feed composition comprising a compound of Formula I as described herein, and an acidulant as described herein.

In another embodiment of the present invention is provided a method of inhibiting or killing microbes in a subject, comprising treating said subject with a composition or combination as described herein. In a preferred embodiment, the subject to be treated is water or food, preferably selected from the group consisting of human food, livestock food, pet food, or aquaculture food.

Animals for which the food, food ingredients and/or feed compositions described herein may be provided include humans, ruminants such as dairy cows, lactating dairy cows, dairy calves, beef cattle, sheep, and goats; aquaculture such as fish and crustaceans (including, but not limited to, salmon, shrimp, carp, tilapia and shell fish; livestock such as swine and horses; poultry such as chickens, turkeys, and hatchlings thereof; and companion animals such as dogs and cats.

Generally, for the method of palatability of feed for aquaculture, the feed can be fed to fish or shellfish; preferably, to carp, tilapia, salmon, trout, smelt, shrimp or prawns; more preferably, to carp, tilapia, smelt, shrimp or prawns; more preferably, to carp. In another embodiment, for the method of palatability of feed for aquaculture, the feed can be fed to carp or salmon. Typical species contemplated or the method of palatability of feed for aquaculture include, but are not limited to, *hypophthalmichthys molitrix* (silver carp), *ctenopharyngodon idellus* (grass carp), *cyprinus carpio* (common carp), *hypophthalmichthys nobilis* (bighead carp), *carassius carassius* (crucian carp), *oreochromic niloticus* (Nile tilapia), and *salmo salar* (Atlantic salmon).

In various preferred embodiments, the methods for enhancing the palatability of feed for aquaculture and feeding fish a fish food, HMBA or salts, esters or amides thereof, or a combination of these is fed to fish or shellfish; preferably, to carp, tilapia, salmon, trout, smelt, shrimp or prawns. In such applications, the concentration of the HMBA or salt, ester or amide thereof is preferably from about 0.01 wt. % to about 0.04 wt. % for either fish or shellfish; preferably, such palatability-enhancing feed formulations can be fed to carp, tilapia, salmon, catfish, trout, smelt, shrimp or prawns; more preferably, the feed can be fed to carp, tilapia, salmon, catfish, or trout; most preferably, the feed is fed to carp.

For antimicrobial and anti-fungal applications, the exact formulation of the above-mentioned animal feed composition is not critical to the present invention. Feed ingredients are selected according to the nutrient requirements of the particular animal for which the feed is intended; these requirements depend, inter alia, upon the age and stage of development of the animal, the sex of the animal, and other factors. Feed ingredients may be grouped into eight classes on the basis of their composition and their use in formulating diets: dry forages and roughages; pasture, range plants and forages fed fresh; silages; energy feeds; protein supplements; mineral supplements; vitamin supplements; and additives. See National Research Council (U.S.) Subcommittee on Feed Composition, *United States-Canadian Tables of Feed Composition*, 3d rev., National Academy Press, pp. 2, 145 (1982). These classes are, to a certain extent, arbitrary, as some feed ingredients could be classified in more than one class. Typically, a feed formulation will also depend upon the costs associated with each ingredient, with the least-expensive composition of ingredients which gives the needed nutrients being the preferred formulation.

Silage is a forage product that is produced from the harvest, storage and fermentation of green forage crops such as corn and grain sorghum plants. These crops are chopped, stems and all, before the grain is ready for harvest. The plant material is stored in silos, storage bags, bunkers or covered piles causing the material to ferment, thereby lowering the pH and preserving the plant material until it can be fed. The ensiled forage is subject to changes in pH, temperature, and oxygen levels.

As noted above, feed formulations depend in part upon the age and stage of development of the animal to be fed. Leeson and Summers (*Nutrition of the Chicken*, 4th ed., pp. 502-510, University Books (2001)) describe several representative poultry diets for pullets, layers, broilers and broiler breeders. For example, most chicken diets contain energy concentrates such as corn, oats, wheat, barley, or sorghum; protein sources such as soybean meal, other oilseed meals (e.g., peanut, sesame, safflower, sunflower, etc.), cottonseed meal, animal protein sources (meat and bone meal, dried whey, fish meal, etc.), grain legumes (e.g., dry beans, field peas, etc.), and alfalfa; and vitamin and mineral supplements, if necessary (for instance, meat and bone meal is high in calcium and phosphorous, and thus these minerals do not need to be supplemented in a feed ration containing meat and bone meal). The relative amounts of the different ingredients in poultry feed depends in part upon the production stage of the bird. Starter rations are higher in protein, while grower and finisher feeds can be lower in protein since older birds require less protein. Model diets for swine and other animals are also available, and may be modified according to the particular needs of the animal(s) to be fed.

The term "inhibit" when used herein in phrases such as "inhibiting bacteria" means any one or more of (a) killing bacteria or mold; (b) any decrease in growth of the bacteria or mold, which may be measured in terms of colony counts; (c) any decrease in the concentration of bacteria or mold; or (d) the inability of bacteria or mold to grow on a particular selection medium. Each of these may be determined, for instance, by comparing the bacterial or fungal colony counts or concentration of bacteria or mold present in the absence of the application of the methods of the present invention with the bacterial or fungal colony counts or concentration of bacteria or mold after application of the methods of the present invention. Application of suitable bactericides or fungicides will show a ten-fold difference in colony counts.

Certain methods of the present invention call for computing, for instance, the concentration, of a compound of Formula I in an animal feed, necessary to inhibit bacteria or mold present in an animal feed, or the concentration of a compound of Formula I and another organic acid or acids necessary to inhibit bacteria or mold present in an animal feed. Provided herein are Examples 1-24, which illustrate amounts of compound of Formula I and/or other organic acids that are sufficient to inhibit bacteria or mold. Also provided hereinabove and hereinbelow are acceptable ranges of amounts of compound of Formula I and/or other organic acids, and ratios between the two, which are suitable for use the methods of the present invention. Other suitable concentrations, ranges and ratios can be determined as needed.

Treatment of the animal feed compositions with the compounds of Formula I and optionally with the other organic acids disclosed herein, or with the compounds of Formula I and optionally with other organic acid(s), may be done by mixing the compound of Formula I (and other organic acid, if present) with the other ingredients in the feed, such as the corn, soybean meal, other feed supplements, etc., as the feed is being formulated. Alternatively, the compound of Formula I and optional other organic acid(s) may be applied to a pre-mixed or pre-pelleted feed. In either case, the compound of Formula I and optional organic acid(s) are preferably added as liquids, and uniformly disperse throughout the bulk of the feed composition when applied. When the compound of Formula I and another organic acid are both used in the methods of the present invention, preferably said compound of Formula I and said other organic acid or acids are mixed together before application to the animal feeds. This pre-mixed compound of Formula I/organic acid(s) blend can be applied to the animal feed ingredients during formulation of the feed compositions, or can be applied to pre-mixed or pre-pelleted feed.

The term "cfu" stands for colony forming units.
The following examples illustrate the invention.

EXAMPLE 1

The effects of increasing quantities of formic acid and/or Alimet® on the colony counts of four bacteria (*E. coli, S. enteritidis, L. plantarum* and *C. jejuni*) were studied. Varying amounts of formic acid or Alimet® were added individually to cultures of these bacteria at pH 4.5 or 6.75 and the cultures were incubated for a length of time, whereupon colony counts were performed.

The *S. enteritidis* culture for the in vitro study contained a mixture of *S. enteritidis* ID-Lelystad (nalidixic acid resistant strain) and *S. enteritidis* (97.07773 RIVM, isolated from poultry). The *E. coli* culture contained a mixture of *E. coli* O149K91K88 (VA2000-08915, pig pathogen) and *E. coli* ATCC 25922. The *L. plantarum* culture studied was *L. plantarum* Bd 99.00553. The *C. jejuni* culture studied was *C. jejuni* C356, ex. ID-Lelystad.

*S. enteritidis* and *E. coli* from fresh overnight cultures in Brain Heart Infusion broth were incubated aerobically in phosphate buffered (0.11 M) salt solution (8.5 g/L NaCl) with peptone (1 g/L), except for *S. enteritidis* at pH 4.5. For this culture, medium 5 was used as the broth, and the culture was incubated aerobically for 4 hours at 37° C. Colony counts were performed according to standard operating procedures.

The fresh overnight culture of *L. plantarum* in brain heart infusion broth were used to inoculate medium 5. The test tubes were incubated under reduced oxygen atmosphere for 6 hours at 37° C. Colony counts were performed.

*C. jejuni* grown on Campylobacter blood-free selective agar was used for inoculation. Preston broth was incubated under reduced oxygen atmosphere for 6 hours at 37° C. Colony counts were performed.

Formic acid and Alimet® were added to the bacterial cultures in concentrations of 0.108 g/L, 0.30 g/L and 0.83 g/L. These dosages were chosen based on commercial use of Alimet® and an approximate 10-fold dilution in the proximal digestive tract.

A summary of the results obtained with formic acid and Alimet® on *S. enteritidis* and *E. coli* is given in Tables 1 and 2, and on *L. plantarum* and *C. jejuni* in Tables 3 and 4; the results are illustrated in FIGS. 1-4.

TABLE 1

Effect of formic acid and Alimet ® on population of
*S. enteritidis* after 4 hours at pH 4.5 and 6.75
initial colony count: 5.23 log cfu/mL

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 5.03 | −0.20 | 6.62 | 1.42 |
| 0.108 | — | 4.92 | −0.31 | 6.71 | 1.51 |
| 0.30 | — | 4.96 | −0.27 | 6.63 | 1.43 |
| 0.83 | — | 4.93 | −0.30 | 6.53 | 1.33 |
| — | 0.108 | 5.04 | −0.19 | 6.79 | 1.59 |
| — | 0.30 | 4.96 | −0.27 | 6.77 | 1.57 |
| — | 0.83 | 4.86 | −0.38 | 6.72 | 1.52 |

TABLE 2

Effect of formic acid and Alimet ® on population of
*E. coli* after 4 hours at pH 4.5 and 6.75
initial colony count: 5.24 log cfu/mL

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 5.36 | 0.12 | 7.47 | 2.23 |
| 0.108 | — | 5.45 | 0.21 | 7.33 | 2.09 |
| 0.30 | — | 5.25 | 0.01 | 7.36 | 2.12 |
| 0.83 | — | 3.96 | −1.28 | 7.39 | 2.15 |
| — | 0.108 | 5.19 | −0.05 | 7.48 | 2.24 |
| — | 0.30 | 4.96 | −0.28 | 7.50 | 2.26 |
| — | 0.83 | 5.08 | −0.16 | 7.49 | 2.25 |

TABLE 3

Effect of formic acid and Alimet ® on population of
L. plantarum after 6 hours at pH 4.5 and 6.75
initial colony count: 5.04 log cfu/mL
$\Delta \log = \log_{sample} - \log_{initial}$

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 5.67 | 0.63 | 6.10 | 1.06 |
| 0.108 | — | 5.67 | 0.63 | 6.09 | 1.05 |
| 0.30 | — | 5.57 | 0.53 | 6.20 | 1.16 |
| 0.83 | — | 5.74 | 0.70 | 5.70 | 0.66 |
| — | 0.108 | 5.75 | 0.71 | 5.88 | 0.84 |
| — | 0.30 | 5.74 | 0.70 | 6.23 | 1.19 |
| — | 0.83 | 5.56 | 0.52 | 6.19 | 1.15 |

TABLE 4

Effect of formic acid and Alimet ® on population of
C. jejuni after 6 hours at pH 4.5 and 6.75
initial colony count: 5.23 log cfu/mL

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 3.70 | −1.53 | 6.54 | 1.31 |
| 0.108 | — | 0.108 | 4.07 | −1.16 | 6.44 |
| 0.30 | — | 0.30 | 3.95 | −1.28 | 6.40 |
| 0.83 | — | 0.83 | 2.80 | −2.43 | 6.34 |
| — | 0.108 | 3.86 | −1.37 | 6.27 | 1.04 |
| — | 0.30 | 2.63 | −2.60 | 6.38 | 1.15 |
| — | 0.83 | <1.30 | <−3.93 | 6.25 | 1.02 |

*S. enteritidis*: Prior to inoculation, the *S. enteritidis* cultures had a colony count of 5.03 log cfu/mL at pH 4.5, and of 6.62 at pH 6.75. The results obtained at both pH values were similar for Alimet® and formic acid: at pH 4.5, neither had a significant effect on inhibiting the growth of *S. enteritidis*; at pH 6.75, no inhibition of *S. enteritidis* was observed.

*E. coli*: Prior to inoculation, at pH 4.5, the *E. coli* cultures had a colony count of 5.36 log cfu/mL; at pH 6.75, it was 7.47. 0.83 g/L Alimet® gave approximately a 1.3 log reduction of *E. coli* growth at pH 4.5, compared to the approximately 0.1 log reduction by the same concentration of formic acid at pH 4.5. Lower concentrations of both Alimet® and formic acid showed little or no inhibition. Neither Alimet® nor formic acid inhibited *E. coli* at pH 6.75.

*L. plantarum*: Prior to inoculation, at pH 4.5, the *L. plantarum* cultures had a colony count of 5.67 log cfu/mL; at pH 6.75, it was 6.10. Neither Alimet® nor formic acid inhibited *L. plantarum* at either pH studied.

*C. jejuni*: Prior to inoculation, at pH 4.5, the *C. jejuni* cultures had a colony count of 3.70 log cfu/mL; at pH 6.75, it was 6.54. All doses of Alimet® inhibited *C. jejuni* at pH 4.5. 0.83 g/L of Alimet® gave approximately a 2.4 log reduction of *C. jejuni* growth at this pH. Lower dosages of Alimet® (0.108 g/L and 0.30 g/L) gave approximately 1.1 and 1.2 log reductions, respectively. Formic acid demonstrated comparable inhibition. No antibacterial activity was shown against *C. jejuni* at pH 6.75 for any Alimet® or formic acid concentration studied.

These results are demonstrated graphically in FIGS. 1A, 1B, 1C, and 1D. FIGS. 2A, 2B, 2C, and 2D demonstrate the pH dependent effects of formic acid and Alimet®. None of the four bacteria studied were inhibited by either formic acid or Alimet® at pH of 6.75; in fact, at this pH, the colony forming unit count of each bacteria increased, with the *E. coli* count increasing the most, and *L. plantarum* increasing the least.

EXAMPLE 2

The effect of higher dosages of Alimet® and formic acid on the colony count of *S. enteritidis* cultures was studied, following the procedure described in Example 1. The results obtained are given in Table 5 and illustrated in FIG. 3.

TABLE 5

Effect of formic acid and Alimet ® on population of
S. enteritidis after 4 hours at pH 4.5 and 6.75
initial colony count: 5.23 log cfu/mL

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 5.15 | −0.09 | 6.92 | 1.69 |
| 1 | — | 5.02 | −0.21 | 6.61 | 1.38 |
| 3 | — | 4.76 | −0.48 | 5.97 | 0.74 |
| 5 | — | 2.37 | −2.86 | 5.43 | 0.20 |
| — | 1 | 5.01 | −0.22 | 6.92 | 1.69 |
| — | 3 | 4.55 | −0.68 | 6.58 | 1.35 |
| — | 5 | 3.83 | −1.41 | 6.10 | 0.87 |

Prior to inoculation, the *S. enteritidis* cultures had a log cfu/mL of 5.15 at pH 4.5, and of 6.92 at pH 6.75. At pH 6.75, the addition of 5 g/L formic acid or 3 g/L Alimet® gave approximately a 1 log cfu/mL growth inhibition. An addition of 5 g/L Alimet® stops the growth of *S. enteritidis*. At pH 4.5, 5 g/L Alimet® reduces the growth of *S. enteritidis* by approximately 2.8 log cfu/mL. Lower concentrations of Alimet® gives a smaller effect. Formic acid at 5 g/L reduces the growth of *S. enteritidis* by approximately 1.3 log cfu/mL. Thus, at the dose ranges studied, the antibacterial effect of Alimet® against *S. enteritidis* is greater than that of formic acid. These results are demonstrated graphically in FIG. 3.

EXAMPLE 3

Combinations of Alimet® and formic acid were studied, following the procedure described in Example 1. The results obtained are given in Table 6 and illustrated in FIGS. 4A and 4B.

TABLE 6

Effect of formic acid and Alimet ® on population of S. enteritidis
after 4 hours at pH 4.5 and 6.75
initial colony count: 5.15 log cfu/mL)

| Acid (g/L) | | pH = 4.5 | | pH = 6.75 | |
|---|---|---|---|---|---|
| Alimet ® | Formic | log cfu/mL | Δ log | log cfu/mL | Δ log |
| — | — | 4.99 | −0.17 | 6.87 | 1.80 |
| 3 | — | 4.76 | −0.39 | 5.89 | 0.82 |
| 5 | — | 2.07 | −3.08 | 5.45 | 0.38 |
| — | 3 | 4.57 | −0.58 | 6.51 | 1.44 |
| — | 5 | 3.94 | −1.21 | 6.19 | 1.12 |
| 0.75 | 2.25 | 4.78 | −0.37 | 6.27 | 1.20 |
| 1.25 | 3.75 | 4.01 | −1.14 | 5.94 | 0.88 |
| 1.50 | 1.50 | 4.73 | −0.42 | 6.11 | 1.04 |
| 2.25 | 0.75 | 4.78 | −0.37 | 5.97 | 0.90 |
| 2.50 | 2.50 | 2.48 | −2.67 | 5.74 | 0.67 |
| 3 | 5 | 1.15 | −4.00 | 5.31 | 0.24 |
| 3.75 | 1.25 | 2.11 | −3.04 | 5.54 | 0.47 |

Combinations of Alimet® and formic acid having a combined concentration of 5 g/L inhibit growth of *S. enteritidis* to a greater extent than do combinations having a combined concentration of 3 g/L. Three 5 g/L combinations were prepared, having Alimet®-to-formic acid ratios of 1:3, 1:1, and 3:1.

At pH 4.5, treatment with 3 g/L of Alimet® alone gave an approximately 0.4 log cfu/mL reduction in *S. enteritidis* growth. Treatment at that pH with 5 g/L of formic acid gave an approximately 1.2 log cfu/mL reduction. Remarkably, treatment with a combination of 3 g/L Alimet® and 5 g/L formic acid gave a reduction of 4 log cfu/mL, which was higher than expected given the individual results with Alimet® and formic acid at those levels. The results obtained suggest that at pH 4.5, combinations of 2.5 g/L Alimet® and 2.5 g/L formic acid, and with 3 g/L Alimet® and 5 g/L formic acid may have a synergistic effect. The latter combination gives the best results of all tested combinations: at pH 4.5, this combination gives 4 log (almost complete) reduction of *S. enteritidis*.

EXAMPLE 4

The effects of blends of organic acids (butyric, citric, formic, lactic, and propionic) and Alimet® on the colony counts of *E. coli* (ATCC 25922) grown in trypticase soy broth at 35 C according to the manufacturer's instructions were studied. Blends of organic acid:Alimet® of 2:1 and 5:1 were studied, at a total concentration (organic acid+Alimet®) of 6 g/L.

The pH of the solutions were originally adjusted to pH 5 by addition of HCl and/or NaOH as needed. Activated *E. coli* culture solutions were transferred to fresh soy broth twice at 24-hour intervals prior to before addition of the organic acid: Alimet® blend. *E. coli* culture solutions were centrifuged; pellet produced was re-suspended with Butterfield buffer, and the resulting solutions were diluted to approximately $10^7$ CFU *E. coil*/mL.

Bottles were inoculated with 100 µL of prepared bacterial suspension and an organic acid:Alimet® blend. Samples were taken after five and 24 hours of incubation, serially diluted and spread-plated on trypticase soy agar, and incubated at 35° C. for 24 hours. Populations of *E. coli* are reported in Table 7 below.

TABLE 7

Effect of Alimet ®/acid blends on
*E. coli* populations in trypticase soy broth
initial colony count: 4.97 log cfu/mL

| Acid | Acid:Alimet ® ratio | original pH | log cfu/mL t = 4 h | log cfu/mL t = 24 h |
|---|---|---|---|---|
| Control | — | — | 7.18 | 9.22 |
| HCl | — | — | 7.85 | 8.34 |
| lactic | 5:1 | ca. 4.2 | 4.68 | 3.98 |
|  | 2:1 | 4.1 | 4.87 | 4.45 |
| formic | 5:1 | 3.1 | 4.95 | <1 |
|  | 2:1 | 3.56 | 4.95 | 1.00 |
| citric | 5:1 | 4.75 | 6.38 | 8.59 |
|  | 2:1 | 4.59 | 5.90 | 8.66 |
| butyric | 5:1 | 4.62 | 4.77 | 3.70 |
|  | 2:1 | 4.6 | 4.85 | 3.80 |
| propionic | 5:1 | 4.54 | 4.79 | 4.57 |
|  | 2:1 | 4.53 | 4.83 | 4.53 |

Blends with formic acid were the most effective among the tested blends to control *E. coli* at both 5:1 and 2:1 blends of formic acid:Alimet®. Upon prolonged exposure (after 5 hours), both ratio give nearly complete reduction of *E. coli*. Blends of lactic, butyric and propionic acids with Alimet® suppressed the growth of *E. coli*, but did not reduce the bacterial population in 24 hours.

EXAMPLE 5

The effects of hydrochloric acid, formic acid, lactic acid, or Alimet® on the colony counts of *E. coli* were studied. Amounts of formic acid, lactic acid, or Alimet® were added to cultures of *E. coli*, grown in a soy broth, at pH 4 or 7.3. The cultures were incubated, and colony counts performed at increasing times.

Figure 5:
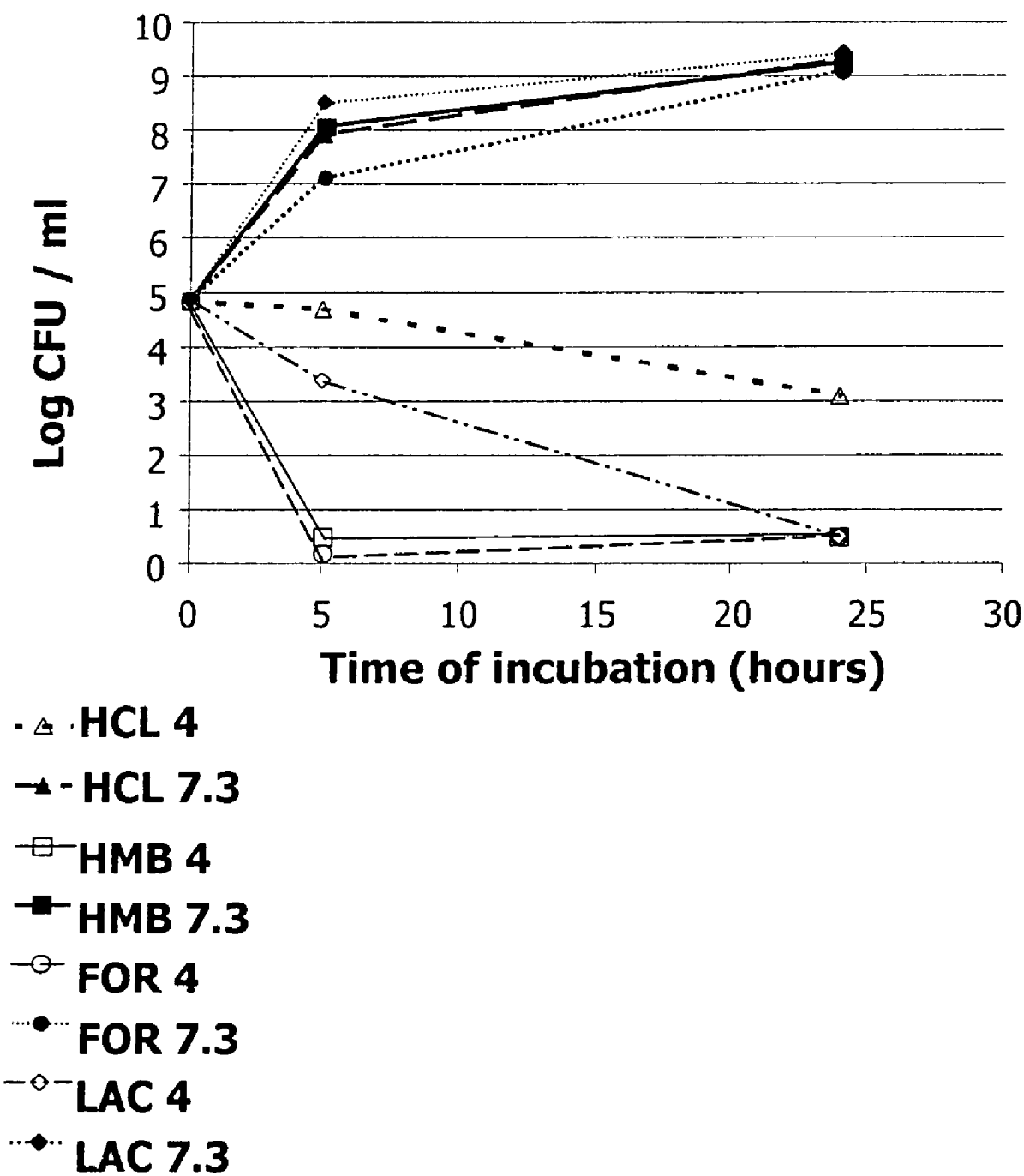
FIG. 5 is a graph comparing the effects of hydrochloric acid, formic acid, lactic acid, and Alimet® on the number of colony forming units of $E.$ $coli$ over time, at pH 4 and 7.3.
Figure 6:
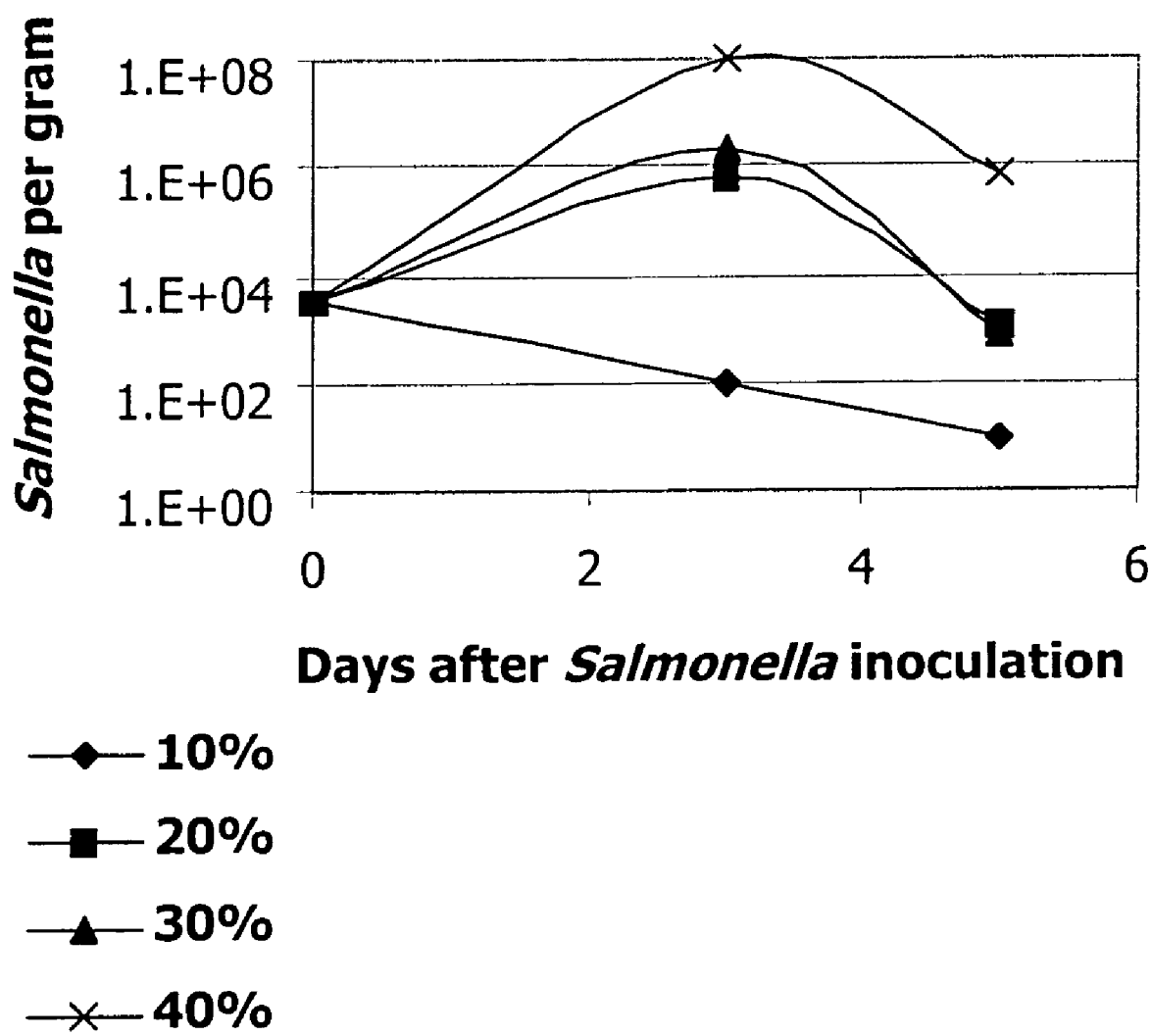
FIG. 6 is a graph showing the effect of moisture level on the number of colony forming units of $Salmonella$ in meat meal premix.

The results are illustrated in FIG. 5. Formic and lactic acid, and Alimet®, decreased the colony counts of *E. coli* better than hydrochloric acid. As in Example 1, Alimet® showed a better reduction of *E. coli* colony counts as compared to formic acids, and showed comparable reduction compared to lactic acid.

EXAMPLE 6

The effect of Alimet® on *Salmonella* in a meat meal premix was studied according to the protocol set forth by Smyser and Snoeyenbos (*Poultry Sci*. 58 (1979) 50-54). Meat meal premix (Papillon Ag Products, Inc., Easton, Md.) containing approximately 77% crude protein was used in the assays. Ten grams of premix test sample for each concentration of Alimet® studied were measured into a sterile tube (three replicates per sample). Sterile water (1 mL) was added to each tube to assure adequate moisture for *salmonella* multiplication. A final moisture level of 20% was achieved after inoculation. Each test sample was inoculated with 1.0 mL of a diluted TSB broth culture of nalidixic acid (NA) resistant *Salmonella* (approximately $10^{3.5}$ cells/g as determined from spread plate counts of the culture). The inoculated samples were mixed with a sterile tongue blade or equivalent tool and incubated at 37° C. for the duration of the trial.

Figure 7:
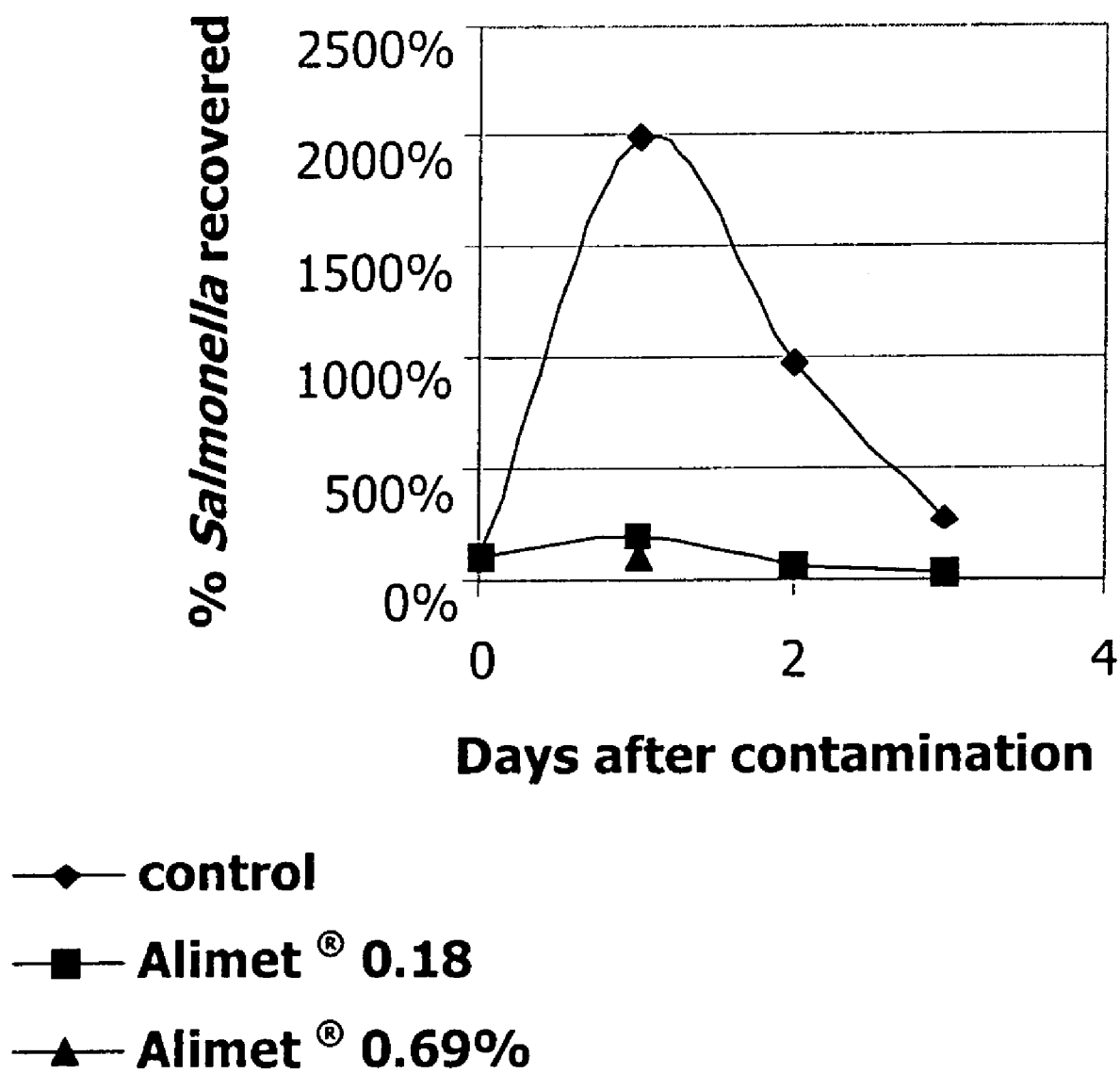
FIG. 7 is a graph showing the percent recovery of $Salmonella$ for different levels of Alimet® in meat meal premix containing 20% moisture.

*Salmonella* counts were determined using brilliant green agar containing sodium nalidixate at days 1, 2 and 3. A 1 g test sample was taken from each tube and transferred to 9 mL sterile water. This test sample was incubated at 4° C. for approximately 4 hours, then agitated for 60-90 seconds. Each test sample was serially diluted in 1:10, 1:100 and 1:1000 proportions, and 100 µL of undiluted test sample, 1:10 diluted sample, 1:100 diluted sample, and 1:1000 diluted samples were plated on brilliant green agar plates containing sodium nalidixate. The percent recovery of *Salmonella* for different levels of Alimet® is reported in Table 8 and FIG. 7.

TABLE 8

Recovery of *Salmonella* in meat meal premix
with 20% moisture; 1:10 dilution

| Alimet ® conc. (reported) | Alimet ® conc. (found) | % *Salmonella* recovered | | | |
|---|---|---|---|---|---|
|  |  | day 0 | day 1 | day 2 | day 3 |
| control (0%) |  | 100% | 1990% | 971% | 267% |
| 0.275% | 0.056% | 100% | 102% | 67% | <3%* |
| 0.18% | 0.140% | 100% | 190% | 65% | 11% |
| 0.25% | 0.188% | 100% | 476% | 139% | 25% |
| 0.36% | 0.192% | 100% | 114% | 62% | 4% |
| 0.40% | 0.220% | 100% | 343% | 267% | 53% |
| 0.69% | 0.631% | 100% | 5% | <3%* | <3%* |

*below detection limit

Figure 8:
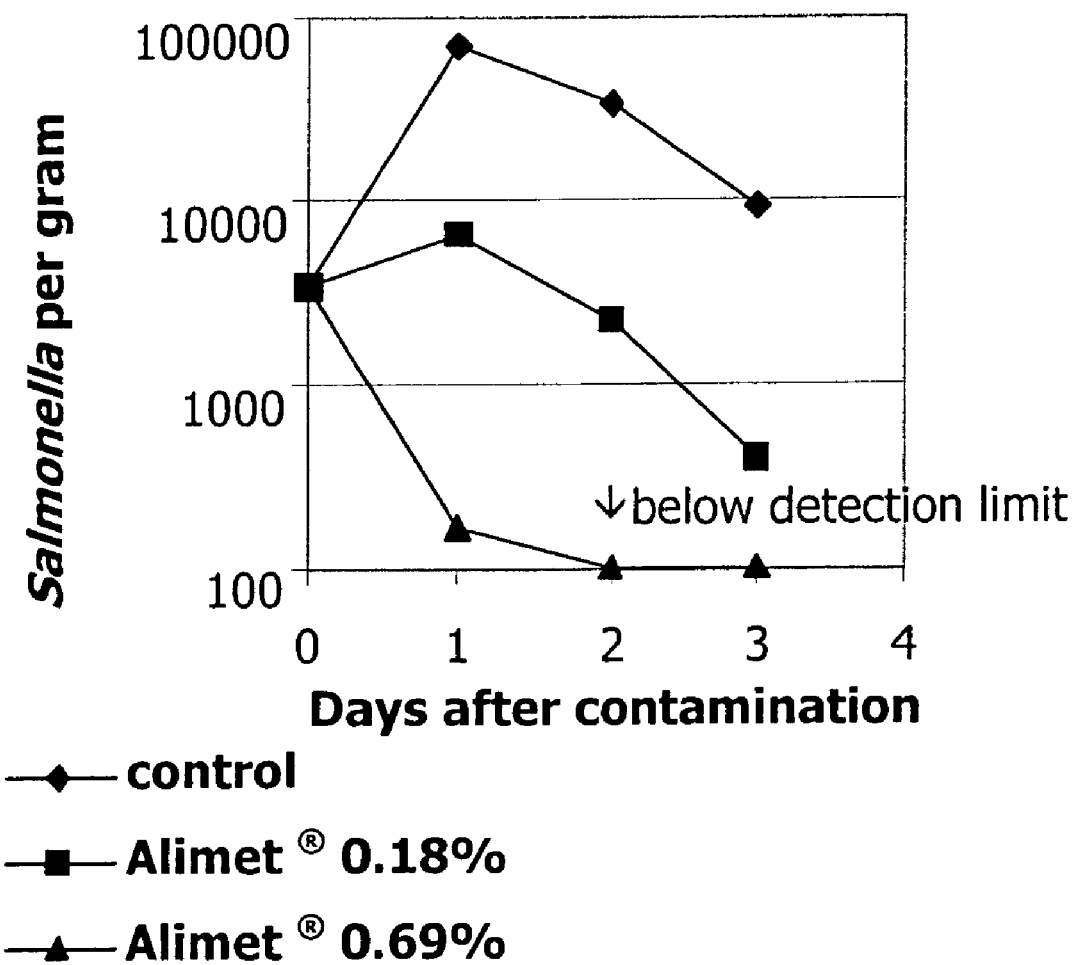
FIG. 8 is a graph showing the effect of Alimet® on the number of colony forming units of $Salmonella$ in meat meal premix containing 20% moisture.

The control sample (no Alimet® added) showed an initial steep increase in *Salmonella* population one day after inoculation, indicating multiplication of the bacteria. This multiplication was followed by a gradual decline in the bacterial counts on days 2 and 3. Results from the highest level of Alimet® tested suggest that Alimet® is bactericidal for *Sal*- monella in meat and bone meal. As FIG. 8 illustrates, Alimet® at this level gives results comparable to treatment with formic acid at 1.65% (15 kg/ton). See Liu, "Using Organic Acids to Control *Salmonella* in Poultry Production," Kemin Industries (Asia) Pte Limited, Singapore, available at http://www.kemin.com.

Alimet® in the range of 0.14-0.22% likewise showed anti-*Salmonella* effects, and does not appear to be dose-dependent in this range. However, each sample was from different batches of MBM, which may be responsible for the lack of dose-response. The initial multiplication seen in the control was significantly reduced upon addition of Alimet® at these levels. The subsequent decline occurred faster for these lower levels of Alimet® compared to the control.

EXAMPLE 7

Fungal growth in basal starter mash was studied in compositions supplemented with DLM or Alimet® as the methionine source. Total microbial growth was monitored by measuring carbon dioxide ($CO_2$) formation in sealed vessels at 28° C. over time. Measurement of $CO_2$ formation does not distinguish between bacterial and mold growth; however, the ability of mold to grow at much lower water activities, compared to bacteria, is well known, and both mold and bacteria play a part in feed degradation.

The technique of using a closed system and measuring $CO_2$ formation has been verified as an approximation of the conditions found in grain storage bins. See, e.g., Muir et al., *Trans. ASAE*, 28(5) 1673-1675 (1985), the contents of which are hereby incorporated by reference in their entirety.

A mash starter mash feed (formulation shown in Table 9, below) was subdivided into three groups: basal (control), 0.2% DLM, or 0.2% Alimet®. The feed studied had no commercial mold inhibitors added, and is representative of a typical broiler feed.

Initial moisture of the feed was 10.8%. After the addition of Alimet® or DLM, the moisture of the samples was adjusted by the addition of 2%, 4%, or 6% sterile distilled water to promote mold growth, achieving three moisture groups: 83.2% dry matter/12.8% moisture; 85.2% dry matter/14.8% moisture; and 87.2% dry matter/16.8% moisture.

For each study, four replicate samples of each moisture group were mixed, and 600 g of the mixture was placed into 1 L containers, sealed, and placed at 28° C. in a temperature-controlled room. Draeger Detector tubes ($CO_2$-measuring, obtained from Fisher Scientific) were used to measure the developed $CO_2$ at different days following vessel sealing (two measurements were made per week). Draeger Short-Term Detector Tubes are glass tubes filled with inert carrier and an indicating reagent. The reagent produces a colorimetric indication in the presence of a particular gas ($CO_2$). The concentration of gas is read directly from the discoloration on the tube's printed scale.

The specific mold species present were not identified. Statistical analysis was accomplished by using Duncan's multiple range test (SAS). Different letters on individual time points in FIGS. 9-11 indicate statistical differences of $P<0.05$.

TABLE 9

Basal starter mash formulation

| Ingredient | % by weight of total mix |
|---|---|
| Corn | 60.551 |
| Soybean meal | 32.254 |

TABLE 9-continued

Basal starter mash formulation

| Ingredient | % by weight of total mix |
|---|---|
| Fat, animal | 3.665 |
| Dical940224PhosfromD (dicalcium phosphate) | 1.861 |
| Limestone | 0.811 |
| Novus Vitamin/Mineral premix manufactured by Trouw Nutrition (Highland, Illinois) | 0.350 |
| Salt | 0.340 |
| L-lysine HCl 78% | 0.097 |
| Threonine | 0.051 |
| Santoquin-mix6 Antioxidant preservative sold by Solutia Inc. (St. Louis, Missouri) | 0.019 |
| Copper Sulfate | 0.003 |

Figure 9:
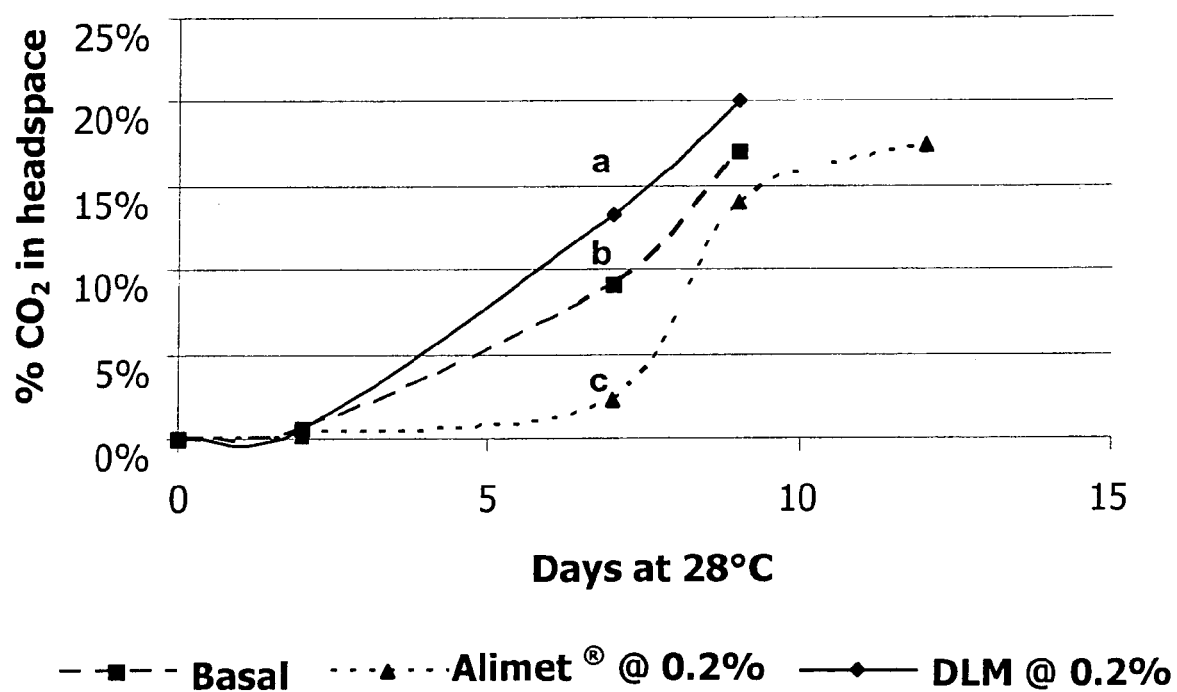
FIG. 9 is a graph illustrating the % $CO_2$ in the headspace for a starter mash with a moisture level of 16.8% having no DLM or Alimet®; with 0.2% DLM; and with 0.2% Alimet®.

As shown in FIG. 9, Alimet® effectively inhibited mold growth for up to seven days at the highest moisture level tested (83.2% dry matter/16.8% moisture), while DLM was the least effective, and, in fact, showed mold growth within two days. In fact, DLM-treated starter mash showed mold growth faster than basal mash (i.e., feed with no added methionine or methionine analog), and faster than the Alimet®-treated mash, for all moisture levels tested.

Figure 10:
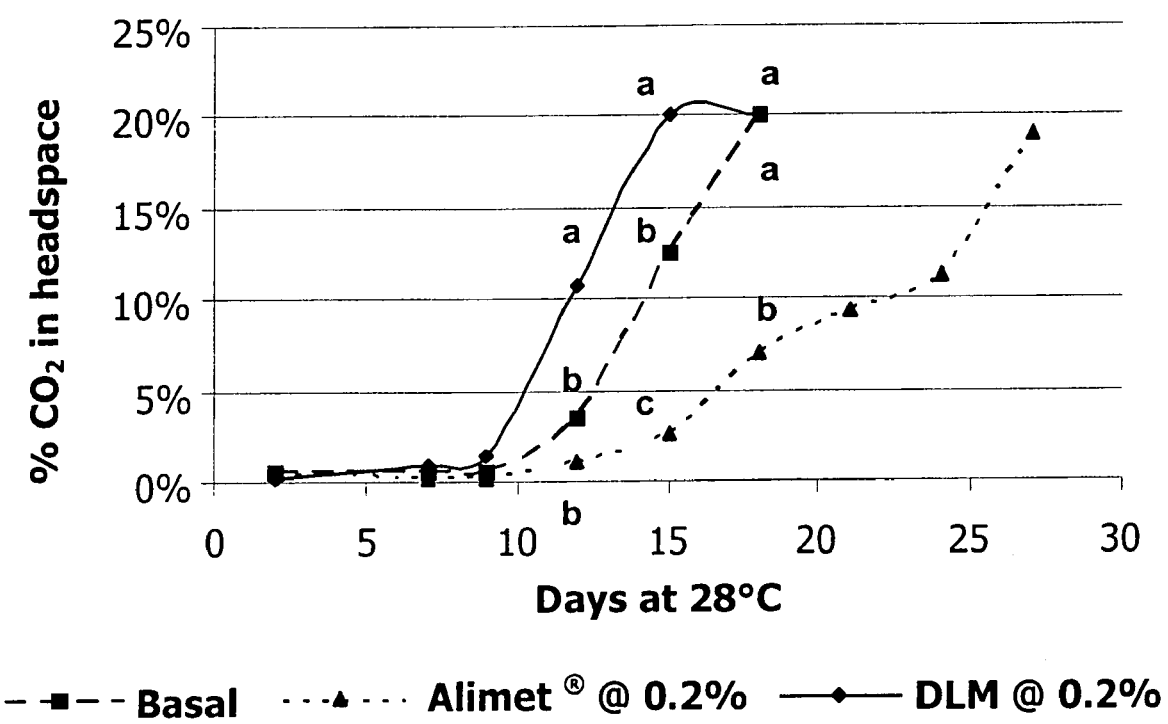
FIG. 10 is a graph illustrating the % $CO_2$ in the headspace for a starter mash with a moisture level of 14.8% having no DLM or Alimet®; with 0.2% DLM; and with 0.2% Alimet®.

As demonstrated in FIG. 10, Alimet®-treated feed showed a slower rate of mold growth in 85.2% dry matter/14.8% moisture feed, than the DLM-treated feed.

Figure 11:
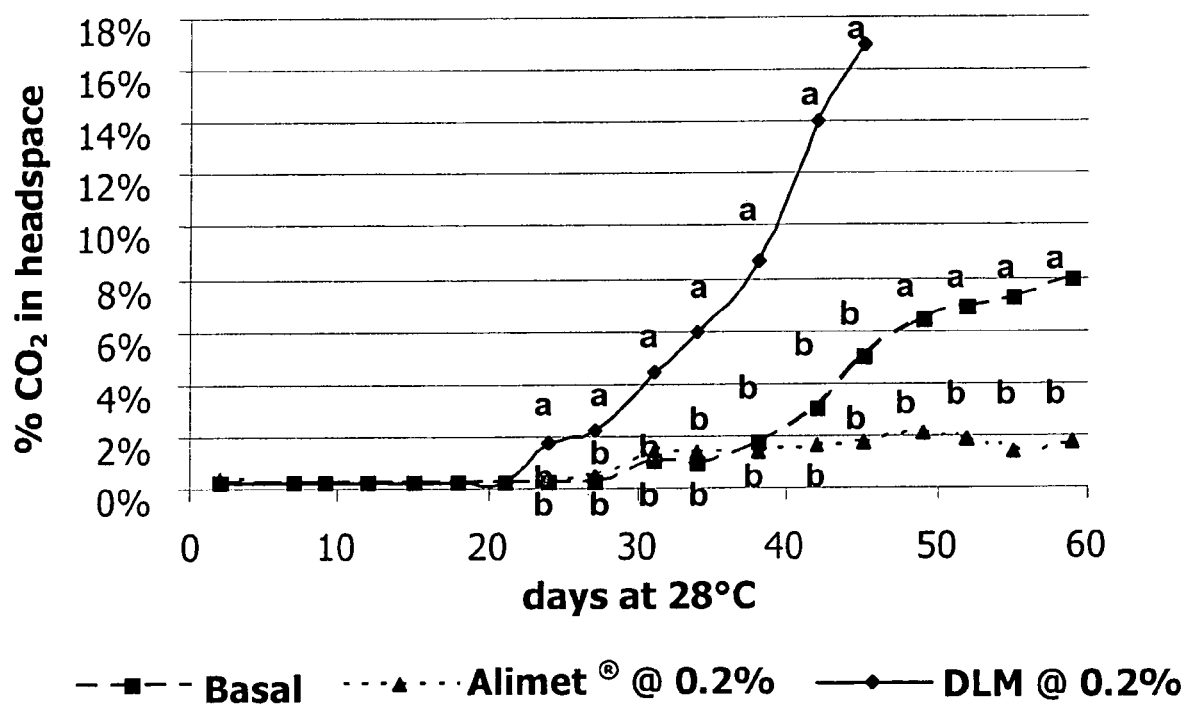
FIG. 11 is a graph illustrating the % $CO_2$ in the headspace for a starter mash with a moisture level of 12.8% having no DLM or Alimet®; with 0.2% DLM; and with 0.2% Alimet®.

For feed having 87.2% dry matter/12.8% moisture, Alimet®-treated feed shows low mold levels for up to sixty days, while DLM-treated feed shows a sharp increase in mold growth after only twenty days (see FIG. 11).

FIGS. 9, 10, and 11 each illustrate that DLM treated mash is more likely to develop mold than either methionine-deficient feed or feed treated with Alimet®, and that Alimet® was more effective in inhibiting mold growth than compared to untreated feed, or feed supplemented with DLM.

EXAMPLE 8

The experiment described above in Example 7 was repeated with blends of 2.0 lb/ton, 1.5 lb/ton, 1.0 lb/ton or 0.5 lb/ton of 65% propionic acid and either 2% Alimet® or 2% DLM. The blends were prepared according to the matrix outlined in Table 8, below. The 65% propionic acid was buffered with ammonium hydroxide to a pH of 5.5.

TABLE 10

Antifungal blends of Alimet ® or DLM with propionic acid

| Trial No. | Alimet ® (%) | Propionic (lb/ton) | DLM (%) |
|---|---|---|---|
| 1 | 0.2 | — | — |
| 2 | — | 2 | 0.2 |
| 3 | — | 1.5 | 0.2 |
| 4 | — | 1.0 | 0.2 |
| 5 | — | 0.5 | 0.2 |
| 6 | — | — | 0.2 |
| 7 | 0.2 | 2 | — |
| 8 | 0.2 | 1.5 | — |
| 9 | 0.2 | 1.0 | — |
| 10 | 0.2 | 0.5 | — |

Statistical analysis was accomplished by using Duncan's multiple range test (SAS). Different letters on individual time points in graphs indicate statistical differences of P<0.05.

Figure 12:
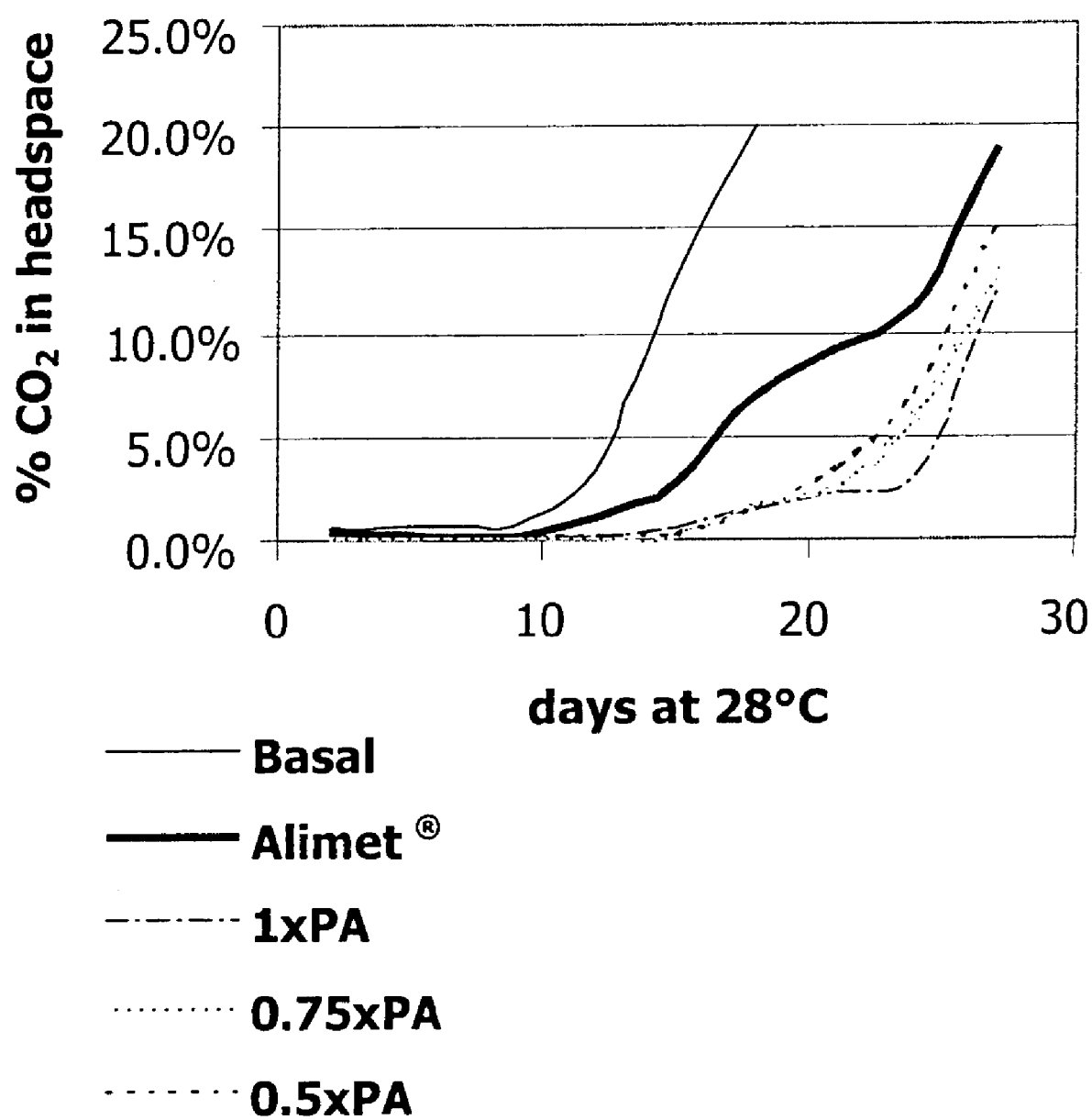
FIG. 12 is a graph illustrating the % $CO_2$ in the headspace for a starter mash with a moisture level of 14.8% having no DLM or Alimet®; with 0.2% Alimet®; with 2 lb/ton 65% propionic acid plus 0.2% DLM; with 1.5 lb/ton 65% propionic acid plus 0.2% DLM; and with 1.0 lb/ton 65% propionic acid plus 0.2% DLM.

As shown in FIG. 12, basal diet having 85.2% dry matter and containing 2.0% Alimet® delayed the onset of mold growth by 5 days; the effect of 2.0 lb/ton, 1.5 lb/ton and 1.0 lb/ton 65% propionic acid is about 11 days, i.e, no significant difference was seen when propionic acid was added beyond 1 lb/ton.

Figure 13:
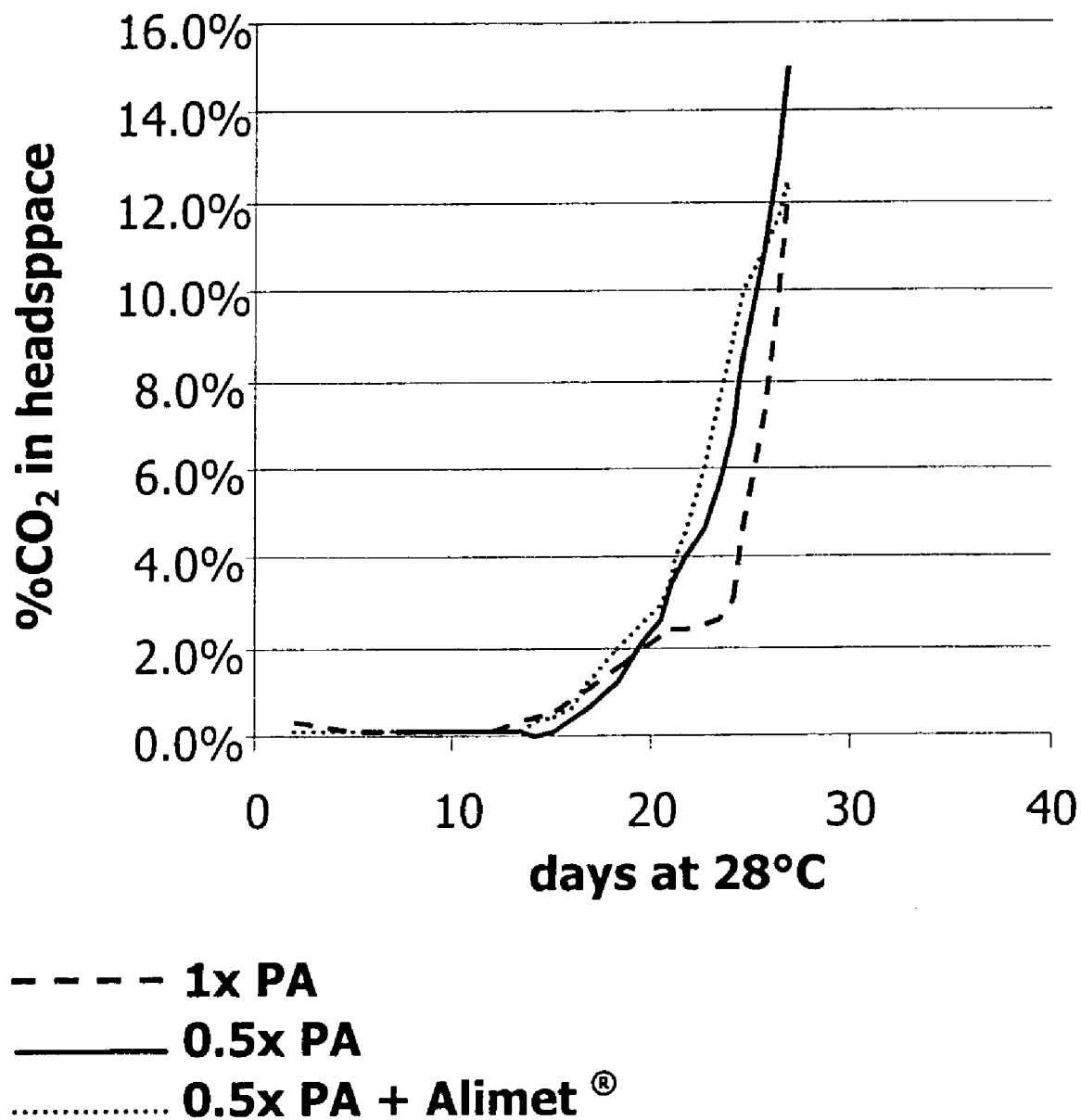
FIG. 13 is a graph illustrating the % $CO_2$ in the headspace for a starter mash with a moisture level of 14.8% with 2 lb/ton 65% propionic acid; with 1.0 lb/ton 65% propionic acid; and with 1.0 lb/ton 65% propionic acid plus 0.2% Alimet®.
Figure 14:
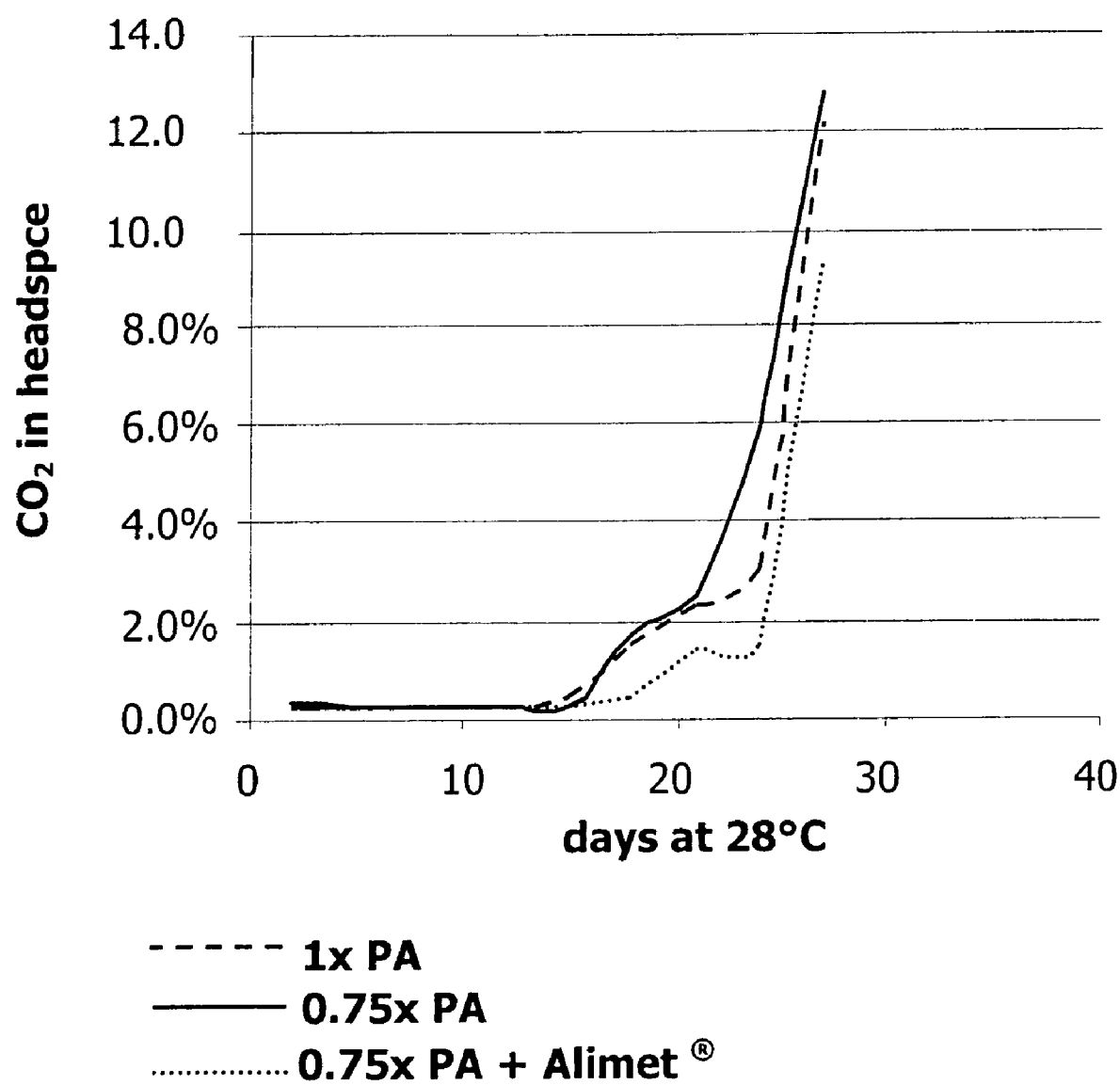
FIG. 14 is a graph illustrating the % $CO_2$ in the headspace for a starter mash with a moisture level of 14.8% with 2 lb/ton 65% propionic acid; with 1.5 lb/ton 65% propionic acid; and with 1.5 lb/ton 65% propionic acid plus 0.2% Alimet®.
Figure 15:
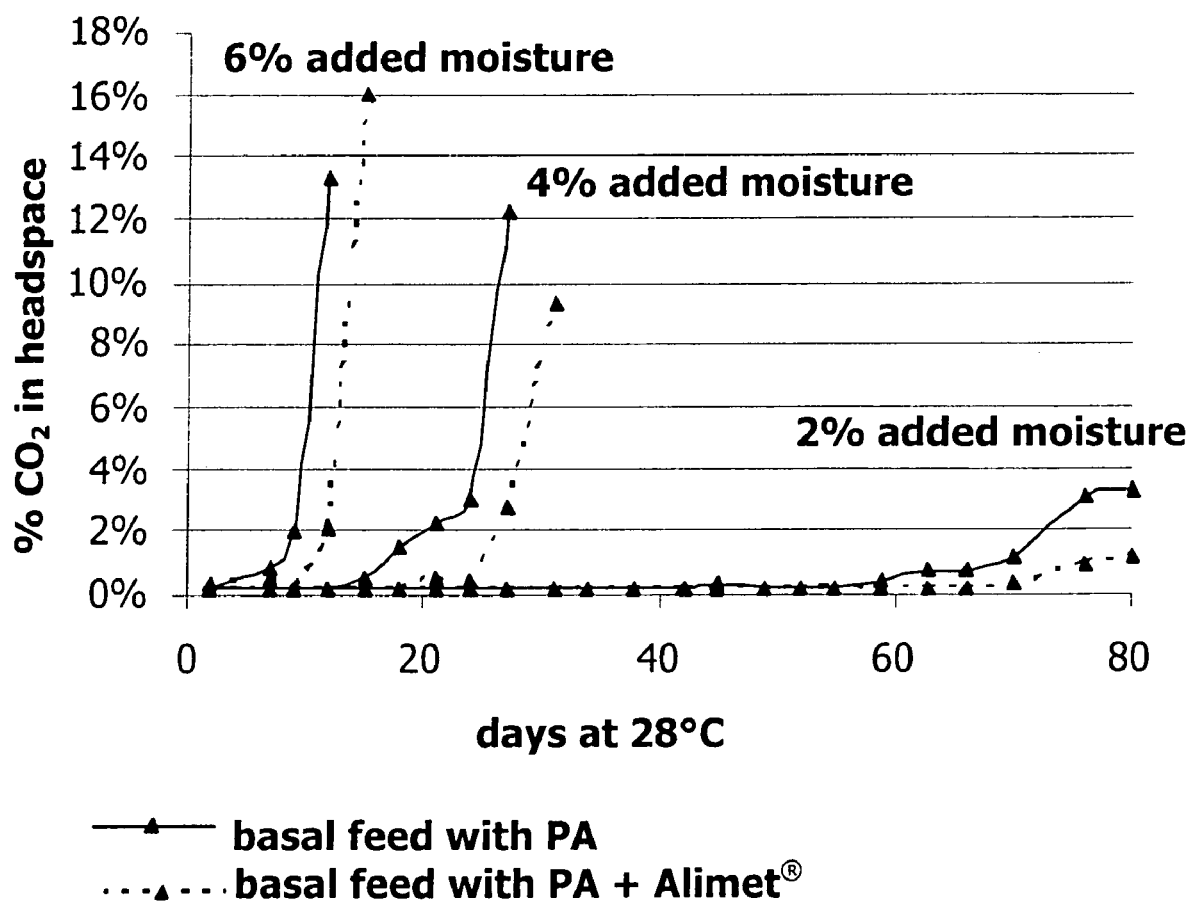
FIG. 15 is a graph illustrating the % $CO_2$ in the headspace for a starter mash treated with propionic acid and propionic acid plus 0.2% Alimet® with a moisture level of 16.8%, 14.8%, 12.8%.

Combinations of Alimet® and propionic acid were compared to feed treated with propionic acid alone, and the results are shown in FIGS. 13-15. The results indicate that, for all moisture levels studied, basal feed containing Alimet® plus propionic acid showed improved mold inhibition compared to feed containing only propionic acid.

EXAMPLE 9

The effect of formic, butyric and lactic acids on *Salmonella* populations in basal corn soy based broiler starter feed was studied to determine the levels of these acids required for complete bacteriacide.

Tests were carried out using 1 g feed (crumble ground) with 6% meat and bone meal ("MBM"). Aqueous 25% solutions of formic, butyric, and lactic acids were prepared. The acid solutions were added to the feed as indicated below; water (1 mL) and 150 mM HCl (1.8 mL) was added to bring the pH to 4.0. Naldixic Acid resistant *Salmonella* (provided by Dr. Stan Bailey, USDA/ARS, Athens, Ga.) (initial colony count=40,000 cfu/g) was added, and the feed solutions were incubated at 37 C for 90 min. Each sample was diluted with 6 mL $H_2O$, plated, and counted the following day. Colony counts are reported in Table 11 below.

TABLE 11

Effect of formic, butyric or lactic acids on *Salmonella* populations in feed
[Δ log = log$_{sample}$ − log$_{control}$]

| Acid | g/L | vol. (µL) | final pH | log cfu/g | Δ log |
|---|---|---|---|---|---|
|  | control |  | 4.47 | 5.0 | — |
| formic | 2.5 | 10 | 4.28 | 4.3 | 0.7 |
|  | 5.0 | 20 | 4.18 | 3.6 | 1.4 |
|  | 7.5 | 30 | 4.1 | 1.0 | 4.0 |
|  | 10 | 40 | 4 | 1.0 | 4.0 |
| butyric | 10 | 40 | 4.31 | 4.3 | 0.7 |
|  | 30 | 120 | 4.17 | 1.0 | 4.0 |
|  | 50 | 200 | 4.04 | 1.0 | 4.0 |
| lactic | 10 | 40 | 4.2 | 4.1 | 0.9 |
|  | 30 | 120 | 3.92 | 1.0 | 4.0 |
|  | 50 | 200 | 3.68 | 1.0 | 4.0 |
|  | control |  | 4.44 |  |  |

Complete bacteriacide was seen at the two highest doses tested for all three acids (7.5 and 10 g/L for formic acid; 30 and 50 g/L for butyric and lactic acids).

EXAMPLE 10

Following the procedure set forth in Example 9, the effect of blends of formic, butyric and/or lactic acids, with and without Alimet®, on *Salmonella* counts in basal corn soy based broiler starter feed (described in Table 9, above, crumble feed with 6% MBM) was studied. The blends studied are described in Table 12, and the results obtained in the in vitro study are reported in Tables 13-15.

TABLE 12

Acid blend formulations (concentrations reported in g/L)

| Blend | Formic Acid | Lactic Acid | Butyric Acid | Alimet ® |
|---|---|---|---|---|
| A1 | 5 | — | — | — |
| A2 | 4 | 4 | — | — |
| A3 | 4 | — | 4 | — |
| A4 | 3 | — | 8 | — |
| A5 | 3 | 4 | 4 | — |
| A6 | 3 | 8 | — | — |
| A7 | 2 | — | 12 | — |
| A8 | 2 | 4 | 8 | — |
| A9 | 2 | 8 | 4 | — |
| A10 | 2 | 12 | — | — |
| A11 | 1 | — | 16 | — |
| A12 | 1 | 4 | 12 | — |
| A13 | 1 | 8 | 8 | — |
| A14 | 1 | 12 | 4 | — |
| A15 | 1 | 16 | — | — |
| A16 | — | — | 20 | — |
| A17 | — | 4 | 16 | — |
| A18 | — | 8 | 12 | — |
| A19 | — | 12 | 8 | — |
| A20 | — | 16 | 4 | — |
| A21 | — | 20 | — | — |
| A22 | 5 | — | — | 1 |
| A23 | 4 | 4 | — | 1 |
| A24 | 4 | — | 4 | 1 |
| A25 | 3 | — | 8 | 1 |
| A26 | 3 | 4 | 4 | 1 |
| A27 | 3 | 8 | — | 1 |
| A28 | 2 | — | 12 | 1 |
| A29 | 2 | 4 | 8 | 1 |
| A30 | 2 | 8 | 4 | 1 |
| A31 | 2 | 12 | — | 1 |
| A32 | 1 | — | 16 | 1 |
| A33 | 1 | 4 | 12 | 1 |
| A34 | 1 | 8 | 8 | 1 |
| A35 | 1 | 12 | 4 | 1 |
| A36 | 1 | 16 | — | 1 |
| A37 | — | — | 20 | 1 |
| A38 | — | 4 | 16 | 1 |
| A39 | — | 8 | 12 | 1 |
| A40 | — | 12 | 8 | 1 |
| A41 | — | 16 | 4 | 1 |
| A42 | — | 20 | — | 1 |
| A43 | 5 | — | — | 2.27 |
| A44 | 4 | 4 | — | 2.27 |
| A45 | 4 | — | 4 | 2.27 |
| A46 | 3 | — | 8 | 2.27 |
| A47 | 3 | 4 | 4 | 2.27 |
| A48 | 3 | 8 | — | 2.27 |
| A49 | 2 | — | 12 | 2.27 |
| A50 | 2 | 4 | 8 | 2.27 |
| A51 | 2 | 8 | 4 | 2.27 |
| A52 | 2 | 12 | — | 2.27 |
| A53 | 1 | — | 16 | 2.27 |
| A54 | 1 | 4 | 12 | 2.27 |
| A55 | 1 | 8 | 8 | 2.27 |
| A56 | 1 | 12 | 4 | 2.27 |
| A57 | 1 | 16 | — | 2.27 |
| A58 | — | — | 20 | 2.27 |
| A59 | — | 4 | 16 | 2.27 |
| A60 | — | 8 | 12 | 2.27 |
| A61 | — | 12 | 8 | 2.27 |
| A62 | — | 16 | 4 | 2.27 |
| A63 | — | 20 | — | 2.27 |

TABLE 13

Effect of formic/butyric/lactic blends without Alimet ® on *Salmonella* populations in feed

| Blend | Final pH | log cfu/g | Δ log reduction |
|---|---|---|---|
| A1 | 4.12 | 3.1 | 1.6 |
| A2 | 4.13 | 2.9 | 1.8 |
| A3 | 4.18 | 3.1 | 1.6 |
| A4 | 4.18 | 3.0 | 1.7 |
| A5 | 4.18 | 3.2 | 1.5 |
| A6 | 4.15 | 2.6 | 2.1 |
| A7 | 4.15 | 2.8 | 1.9 |
| A8 | 4.18 | 2.8 | 1.9 |
| A9 | 4.16 | 2.5 | 2.2 |
| A10 | 4.12 | 1.8 | 2.9 |
| A11 | 4.16 | 2.7 | 2.0 |
| A12 | 4.17 | 2.7 | 2.0 |
| A13 | 4.16 | 2.8 | 1.9 |
| A14 | 4.14 | 2.9 | 1.8 |
| A15 | 4.1 | 2.6 | 2.1 |
| A16 | 4.16 | 2.7 | 2.0 |
| A17 | 4.21 | 2.7 | 2.0 |
| A18 | 4.18 | 2.5 | 2.2 |
| A19 | 4.16 | 1.7 | 3.0 |
| A20 | 4.13 | 2.7 | 2.0 |
| A21 | 4.05 | 1.8 | 2.9 |
| control | 4.33 | 4.7 | — |

TABLE 14

Effect of formic/butyric/lactic blends with 1 g/L added Alimet ® on *Salmonella* populations in feed

| Blend | Final pH | log cfu/g | Δ log reduction |
|---|---|---|---|
| A22 | 4.09 | 3.5 | 1.0 |
| A23 | 4.09 | 2.1 | 2.4 |
| A24 | 4.09 | 2.9 | 1.6 |
| A25 | 4.12 | 2.2 | 2.3 |
| A26 | 4.11 | 2.3 | 2.2 |
| A27 | 4.1 | 1.9 | 2.6 |
| A28 | 4.11 | 2.3 | 2.2 |
| A29 | 4.14 | 2.3 | 2.2 |
| A30 | 4.1 | 1.9 | 2.6 |
| A31 | 4.06 | 1.6 | 2.9 |
| A32 | 4.15 | 2.4 | 2.1 |
| A33 | 4.15 | 2.3 | 2.2 |
| A34 | 4.15 | 1.4 | 3.1 |
| A35 | 4.11 | 1.7 | 2.8 |
| A36 | 4.06 | 1.8 | 2.7 |
| A37 | 4.13 | 2.0 | 2.5 |
| A38 | 4.16 | 2.0 | 2.5 |
| A39 | 4.13 | 1.8 | 2.7 |
| A40 | 4.12 | 1.8 | 2.7 |
| A41 | 4.08 | 1.7 | 2.8 |
| A42 | 4.06 | 1.7 | 2.8 |
| control | 4.33 | 4.7 | 0.2 |
| control | 4.36 | 4.5 | — |

TABLE 15

Effect of formic/butyric/lactic blends with 2.27 g/L added Alimet ® on *Salmonella* populations in feed

| Blend | Final pH | log cfu/g | Δ log reduction |
|---|---|---|---|
| A43 | 4.21 | 2.8 | 0.7 |
| A44 | 4.17 | 2.8 | 0.7 |
| A45 | 4.18 | 3.0 | 0.5 |
| A46 | 4.18 | 2.8 | 0.7 |
| A47 | 4.15 | 3.7 | −0.2 |
| A48 | 4.11 | 2.0 | 1.5 |

TABLE 15-continued

Effect of formic/butyric/lactic blends with 2.27 g/L added Alimet ® on *Salmonella* populations in feed

| Blend | Final pH | log cfu/g | Δ log reduction |
|---|---|---|---|
| A49 | 4.19 | 2.7 | 0.8 |
| A50 | 4.19 | 2.8 | 0.7 |
| A51 | 4.16 | 2.8 | 0.7 |
| A52 | 4.13 | 2.4 | 1.1 |
| A53 | 4.2 | 2.8 | 0.7 |
| A54 | 4.2 | 2.7 | 0.8 |
| A55 | 4.14 | 2.3 | 1.2 |
| A56 | 4.13 | 1.7 | 1.8 |
| A57 | 4.08 | 1.0 | 2.5 |
| A58 | 4.21 | 2.3 | 1.2 |
| A59 | 4.23 | 2.7 | 0.8 |
| A60 | 4.17 | 2.0 | 1.5 |
| A61 | 4.14 | 2.0 | 1.5 |
| A62 | 4.12 | 0.7 | 2.8 |
| A63 | 4.07 | 0.7 | 2.8 |
| control | 4.37 | 3.5 | 0 |
| control | 4.45 | 3.5 | — |

Addition of 1 g/L Alimet® to the blend gave improved results in sixteen of the blends tested.

The formulations of the blends used in Examples 11-13 are set forth in Table 16.

TABLE 16

Organic acid/Alimet ® blend formulations

| Blend | Alimet ® | Phos.[1] | Butyric | Formic | Lactic | Prop.[2] |
|---|---|---|---|---|---|---|
| A64 | 30 | 30 | 20 | — | 20 | — |
| A65 | 30 | — | — | 50 | — | 20 |
| A66 | 20 | 20 | 12 | 30 | 18 | — |
| A67 | 10 | 10 | — | 75 | — | 5 |
| A68 | 30 | 35 | 15 | — | 20 | — |
| A69 | 30 | 5 | — | 55 | — | 10 |
| A70 | 20 | 20 | 12 | — | 18 | 30 |
| A71 | 10 | 5 | 5 | 75 | — | 5 |
| A72 | — | — | — | 50 | — | 50 |
| A73 | — | — | — | 75 | — | 25 |

[1]Phosphoric acid
[2]Propionic acid

EXAMPLE 11

The effects of blends of organic acids on the colony counts of *Salmonella* in a corn soy based diet as set forth in Table 9, above, (DLM at 0.2%) were studied, following the procedure outlined in Example 9. The results are reported in Table 17.

TABLE 17 effect of acid blends on *Salmonella* populations in corn soy based diet

| | | after 60 min. | | |
|---|---|---|---|---|
| Blend | g/kg | cfu/g[1,2] | log cfu/g | Δ log reduction |
| control | | 40,000 | 4.6 | — |
| A64 | 5 | 29,700 | 4.5 | 0.1 |
| | 10 | 2,300 | 3.4 | 1.2 |
| A65 | 5 | 3,100 | 3.5 | 1.1 |
| | 10 | 40 | 1.6 | 3.0 |
| A66 | 5 | 10,000 | 4.0 | 0.6 |
| | 10 | 40 | 1.6 | 3.0 |
| A67 | 5 | 3,000 | 3.5 | 1.1 |
| | 10 | 40 | 1.6 | 3.0 |
| control | | 46,000 | 4.7 | — 4.68 |

TABLE 17-continued effect of acid blends on *Salmonella* populations in corn soy based diet

| control | 13,900 | 4.1 | — | | after 90 min.

| Blend | g/kg | cfu/g[1,2] | log cfu/g | Δ log reduction | final pH |
|---|---|---|---|---|---|
| A64 | 5 | 19,300 | 4.3 | 0.4 | 4.45 |
|  | 10 | 2,400 | 3.4 | 1.3 | 4.32 |
| A65 | 5 | 200 | 2.3 | 2.4 | 4.44 |
|  | 10 | 40 | 1.6 | 3.1 | 4.25 |
| A66 | 5 | 13,500 | 4.1 | 0.6 | 4.37 |
|  | 10 | 40 | 1.6 | 3.1 | 4.22 |
| A67 | 5 | 200 | 2.3 | 2.4 | 4.33 |
|  | 10 | 40 | 1.6 | 3.1 | 4.02 |
| control |  | 38,800 | 4.6 | — | 4.68 |

[1]40 cfu/g (minimum detection level) reported when no *Salmonella* detected.
[2]Single reading for each treatment.

Three of the four blends tested showed complete bacteriacide at 10 g/kg (1%) application. Both the A65 and A67 blends showed significant bacteriacide at the lower application rate (0.5%)

EXAMPLE 12

The effect of blends of organic acids on *Salmonella* counts were studied using model poultry and swine diets. Blends A70 and A71 were tested using the corn soy based diet set forth in Table 9, above, with DLM added at 0.2%. The model poultry diet was a corn soy based layer diet, no meat product; the effects of blends A68 and A69 were tested with this diet.

Blends were added to 1 g of feed sample. *Salmonella* (200 μL, 40,000 cfu) were added to each feed sample, and mixed. The samples were incubated at room temperature, then diluted 1:10 with water and plated on BG plate. Results are reported in Table 18.

TABLE 18 effect of acid blends on *Salmonella* populations in corn soy based diet

|  |  | Final | after 1 h | | after 24 h | |
|---|---|---|---|---|---|---|
| blend | g/kg | pH | cfu/g | log cfu/g | cfu/g | log cfu/g |
| control (Diet #1) |  | 5.83 | 12,400 | 4.1 | 10,133 | 4.0 |
| A70 | 2 | 5.53 | 15,000 | 4.2 | 3,300 | 3.5 |
|  | 5 | 5.32 | 3,900 | 3.6 | 1,200 | 3.1 |
|  | 7.5 | 5.08 | 3,400 | 3.5 | 700 | 2.8 |
|  | 10 | 4.94 | 1,500 | 3.2 | 100 | 2.0 |
| A71 | 2 | 5.42 | 9,600 | 4.0 | 2,300 | 3.4 |
|  | 5 | 5.16 | 1,300 | 3.1 | 100 | 2.0 |
|  | 7.5 | 4.84 | 200 | 2.3 | 100 | 2.0 |
|  | 10 | 4.66 | 100 | 2.0 | 100 | 2.0 |
| control (Diet #2) |  | 5.92 | 15,300 | 4.2 | 6,300 | 3.8 |
| A68 | 2 | 5.70 | 10,400 | 4.0 | 5,600 | 3.7 |
|  | 5 | 5.67 | 6,300 | 3.8 | 4,200 | 3.6 |
|  | 7.5 | 5.54 | 9,900 | 4.0 | 2,600 | 3.4 |
|  | 10 | 5.36 | 8,300 | 3.9 | 1,300 | 3.1 |
| A69 | 2 | 5.53 | 7,800 | 3.9 | 3,300 | 3.5 |
|  | 5 | 5.29 | 3,600 | 3.6 | 1,200 | 3.1 |
|  | 7.5 | 5.22 | 1,200 | 3.1 | 300 | 2.5 |
|  | 10 | 5.08 | 1,000 | 3.0 | 100 | 2.0 |

EXAMPLE 13

The antibacterial effect of two organic acid/Alimet® blends were compared with blends containing formic and propionic acids, and with no Alimet®, following the procedure set forth in Example 12. Results after 90 minutes are reported in Table 19.

TABLE 19

| Blend | g/kg | cfu/g | log cfu/g | final pH |
|---|---|---|---|---|
| control |  | 29,400 | 4.5 | 4.54 |
| A65 | 2 | 140 | 2.1 | 4.56 |
|  | 5 | 80 | 1.9 | 4.45 |
|  | 10 | 1 | 0 | 4.32 |
| A67 | 2 | 900 | 3.0 | 4.57 |
|  | 5 | 1,100 | 3.0 | 4.49 |
|  | 10 | 1 | 0 | 4.25 |
| A72 | 2 | 2,100 | 3.3 | 4.5 |
|  | 5 | 90 | 2 | 4.39 |
|  | 10 | 1 | 0 | 4.15 |
| A73 | 2 | 2,700 | 3.4 | 4.51 |
|  | 5 | 600 | 2.8 | 4.4 |
|  | 10 | 1 | 0 | 4.1 |
| control |  | 30,650 | 4.5 | 4.68 |

EXAMPLE 14

The antibacterial effect of two different batches of Alimet® on a corn soy diet (see Example 9, above) were compared. The first batch was of an unknown age and the second batch was freshly prepared (less than two weeks old). The protocol set forth in Example 9 was used, and results are reported in Table 20.

TABLE 20 effect of two different batches of Alimet ® on *Salmonella* populations in corn soy based diet after 90 min. incubation

| Acid | g/kg added | cfu/g | log cfu/g | pH |
|---|---|---|---|---|
| control |  | 6,850 | 3.8 | 4.80 |
| Alimet ® batch 1 | 2.3 | 800 | 2.9 | 4.72 |
|  | 5.7 | 50 | 1.7 | 4.66 |
|  | 8.5 | 120 | 2.1 | 4.58 |
|  | 11.4 | 0 | — | 4.57 |
| Alimet ® batch 2 | 2.3 | 3,900 | 3.6 | 4.68 |
|  | 5.7 | 300 | 2.5 | 4.54 |
|  | 8.5 | 20 | 1.3 | 4.61 |
|  | 11.4 | 20 | 1.3 | 4.57 |
| control |  | 14,850 | 4.2 | 4.80 |

The first batch of Alimet® showed slightly improved bactericidal effects at lower concentrations. Both batches were bactericidal at higher doses.

EXAMPLE 15

The antibacterial effect of dry acids (fumaric, tartaric, and sorbic) alone and in combination with Alimet® blends were studied according to the protocol of Example 9. The formulations of the blends studied are reported in Table 21. The results after 90 minutes are reported in Table 22.

TABLE 21

|  | acid concentration (g/kg) | | | |
|---|---|---|---|---|
| Blend | Alimet ® | Fumaric | Tartaric | Sorbic |
| A74 | 10 | 0 | 0 | 0 |
| A75 | 0 | 10 | 0 | 0 |
| A76 | 0 | 0 | 10 | 0 |

TABLE 21-continued

| Blend | acid concentration (g/kg) | | | |
|---|---|---|---|---|
| | Alimet ® | Fumaric | Tartaric | Sorbic |
| A77 | 0 | 0 | 0 | 10 |
| A78 | 5 | 5 | 0 | 0 |
| A79 | 5 | 0 | 5 | 0 |
| A80 | 5 | 0 | 0 | 5 |

TABLE 22

| Blend | cfu/g | log cfu/g | Δ log reduction |
|---|---|---|---|
| control | 27900 | 4.4 | |
| A74 | 40 | 1.6 | 2.8 |
| A75 | 30 | 1.5 | 3.0 |
| A76 | 14450 | 4.2 | 0.3 |
| A77 | 1150 | 3.1 | 1.4 |
| A78 | 0 | — | 4.4 |
| A79 | 4600 | 3.7 | 0.8 |
| A80 | 170 | 2.2 | 2.2 |
| control | 13900 | 4.1 | |

EXAMPLE 16

The effect of formic acid on *Lactobacillus plantarum* was studied. As demonstrated in Example 1, addition of Alimet® at pH 3.5 to a bacteria-containing broth showed a clear lethal effect on *L. plantarum* at doses of 3 and 5 g/l. Comparable concentrations of formic acid (technical quality 85%, ex Franklin Products) were also studied and compared against Alimet®.

Fresh overnight culture *L. plantarum* in Brain Heart Infusion broth is used to inoculate medium 5 at a log 4.1 cfu/mL at pH 3.5. The tubes are incubated under oxygen reduced atmosphere for 6 hours at 37° C. Colony counts are performed according standard procedures. All analyses were performed in duplicate, and the results are reported in Table 23.

TABLE 23

Effect of Alimet ® and formic acid on *L. plantarum* colony counts in broth (after 6 hours)
initial log cfu/mL = 5.61
Δ log = log$_{6 hours}$ − log$_{initial}$

| Acid | g/kg | log cfu/mL | Δ log |
|---|---|---|---|
| control | | 5.67 | 0.06 |
| Alimet ® | 3 | 3.02 | −2.59 |
| | 5 | 0.83 | −4.78 |
| formic acid | 3 | 3.19 | −2.42 |
| | 5 | −0.30 | −5.91 |

EXAMPLE 17

Blends of various acids with Alimet® were studied at pH 4.5. The effect of these blends on *S. enteritidis* colony counts in broth were studied, using the protocol set out in Example 1. Results are reported in Tables 24-26.

TABLE 24

Effects of blends of acids and Alimet ® on *S. enteritidis* colony counts in broth

| Blend | Acid | Acid g/L | Alimet ® g/L | log cfu/mL |
|---|---|---|---|---|
| | | Control | | 5.04 |
| | | Control (Alimet ®) | | −0.30 |
| A81 | formic | 5 | 0 | 3.93 |
| A82 | | 4.5 | 0.5 | 0.74 |
| A83 | | 4 | 1 | 0.24 |
| A84 | | 3.75 | 1.25 | 0.15 |
| A85 | | 3.5 | 1.5 | −0.15 |
| A86 | | 2.5 | 2.5 | −0.30 |
| A87 | butyric | 5 | 0 | 4.44 |
| A88 | | 4.5 | 0.5 | 3.56 |
| A89 | | 4 | 1 | 1.70 |
| A90 | | 3.75 | 1.25 | 1.44 |
| A91 | | 3.5 | 1.5 | −0.15 |
| A92 | | 2.5 | 2.5 | −0.30 |
| A93 | citric | 5 | 0 | 4.74 |
| A94 | | 4.5 | 0.5 | 4.40 |
| A95 | | 4 | 1 | 4.34 |
| A96 | | 3.75 | 1.25 | 1.59 |
| A97 | | 3.5 | 1.5 | 1.19 |
| A98 | | 2.5 | 2.5 | 0.24 |

TABLE 25

Effects of blends of acids or formaldehyde and Alimet ® on *S. enteritidis* colony counts in broth

| Blend | Acid | Acid g/L | Alimet ® g/L | log cfu/mL |
|---|---|---|---|---|
| | | Control | | 5.02 |
| | | Control (Alimet ®) | | 0.00 |
| A99 | fumaric | 5 | 0 | 4.68 |
| A100 | | 4.5 | 0.5 | 4.65 |
| A101 | | 4 | 1 | 4.43 |
| A102 | | 3.75 | 1.25 | 4.38 |
| A103 | | 3.5 | 1.5 | 4.36 |
| A104 | | 2.5 | 2.5 | 2.32 |
| A105 | lactic | 5 | 0 | 4.44 |
| A106 | | 4.5 | 0.5 | 4.48 |
| A107 | | 4 | 1 | 4.43 |
| A108 | | 3.75 | 1.25 | 4.51 |
| A109 | | 3.5 | 1.5 | 4.75 |
| A110 | | 2.5 | 2.5 | 4.55 |
| A111 | malic | 5 | 0 | 5.01 |
| A112 | | 4.5 | 0.5 | 4.71 |
| A113 | | 4 | 1 | 4.77 |
| A114 | | 3.75 | 1.25 | 4.91 |
| A115 | | 3.5 | 1.5 | 4.96 |
| A116 | | 2.5 | 2.5 | 4.89 |

TABLE 26

Effects of blends of acids or formaldehyde and Alimet ® on *S. enteritidis* colony counts in broth

| Blend | Acid | Acid g/L | Alimet ® g/L | log cfu/mL |
|---|---|---|---|---|
| | | Control | | 4.95 |
| | | Control (Alimet ®) | | 0.63 |
| A117 | propionic | 5 | 0 | 4.34 |
| A118 | | 4.5 | 0.5 | 4.34 |
| A119 | | 4 | 1 | 4.10 |
| A120 | | 3.75 | 1.25 | 3.76 |
| A121 | | 3.5 | 1.5 | 3.30 |
| A122 | | 2.5 | 2.5 | 0.87 |
| A123 | phosphoric | 5 | 0 | 4.68 |
| A124 | | 4.5 | 0.5 | 4.67 |
| A125 | | 4 | 1 | 4.56 |
| A126 | | 3.75 | 1.25 | 4.62 |
| A127 | | 3.5 | 1.5 | 4.48 |

TABLE 26-continued

Effects of blends of acids or formaldehyde and Alimet® on *S. enteritidis* colony counts in broth

| Blend | Acid | Acid g/L | Alimet ® g/L | log cfu/mL |
|---|---|---|---|---|
| A128 | | 2.5 | 2.5 | 3.30 |
| A129 | formaldehyde | 5 | 0 | −0.30 |
| A130 | | 4.5 | 0.5 | −0.30 |
| A131 | | 4 | 1 | −0.30 |
| A132 | | 3.75 | 1.25 | −0.30 |
| A133 | | 3.5 | 1.5 | −0.30 |
| A134 | | 2.5 | 2.5 | −0.30 |

Phosphoric, fumaric, lactic, malic and propionic acids do not show a significant inhibitory effect at 5 g/l. Blends of these acids with Alimet® gave similar results, except for the 50:50 blend of fumaric and Alimet®, which gave greater than 2 log reduction in colony counts compared to 5 g/L of fumaric alone, and the 50:50 blend of phosphoric and Alimet®, which gave an approximately 1.3 log reduction compared to 5 g/L of phosphoric alone.

Blends of formic acid and Alimet® performed more favorably than formic acid alone for all the blends studied. Similarly, blends of butyric acid and Alimet®, and citric acid with Alimet®, gave improved bactericidal effects with increasing proportion of Alimet® added.

EXAMPLE 18

The antibacterial effect of acid blends was studied according to the protocol of Example 9. Phosphoric acid (75%) was obtained from Astaris (St. Louis, Mo.), lot # TK60. L-lactic acid (80%) was obtained from Purac America (Lincolnshire, Ill.), batch # 015703-A. Butyric acid (99+%) was obtained from Aldrich Chemical Co. (Milwaukee, Wis.), batch # 0.511A. The formulations of the blends studied are reported in Table 27. The results are reported in Table 28.

TABLE 27

| Blend | acid formulations (% of total) | | | |
|---|---|---|---|---|
| | Alimet ® | Lactic | Phosphoric | Butyric |
| A135 | 0.33 | 0.67 | — | — |
| A136 | 0.317 | 0.633 | 0.05 | — |
| A137 | 0.267 | 0.533 | 0.20 | — |
| A138 | 0.25 | 0.50 | 0.25 | — |
| A139 | 0.33 | 0.33 | — | 0.33 |
| A140 | 0.317 | 0.317 | 0.05 | 0.317 |
| A141 | 0.267 | 0.267 | 0.20 | 0.267 |
| A142 | 0.25 | 0.25 | 0.25 | 0.25 |
| A143 | 0.33 | — | — | 0.67 |
| A144 | 0.317 | — | 0.05 | 0.633 |
| A145 | 0.267 | — | 0.20 | 0.533 |
| A146 | 0.25 | — | 0.25 | 0.50 |

TABLE 28

| Blend | cfu/g | log cfu/g | final pH |
|---|---|---|---|
| control | 7,900 | 3.9 | 4.86 |
| A135 | 20 | 1.3 | 4.49 |
| A136 | 20 | 1.3 | 4.39 |
| A137 | 340 | 2.5 | 4.52 |
| A138 | 160 | 2.2 | 4.44 |
| A139 | 80 | 1.9 | 4.50 |
| A140 | 20 | 1.3 | 4.49 |
| A141 | 160 | 2.2 | 4.42 |

TABLE 28-continued

| Blend | cfu/g | log cfu/g | final pH |
|---|---|---|---|
| A142 | 160 | 2.2 | 4.43 |
| A143 | 160 | 2.2 | 4.48 |
| A144 | 40 | 1.6 | 4.48 |
| A145 | 240 | 2.4 | 4.53 |
| A146 | 20 | 1.3 | 4.42 |
| control | 22,100 | 4.3 | 4.73 |

EXAMPLE 19

The effects of blend A71 at neutral pH were tested. The blend was added to 1 g of feed sample. *Salmonella* (40,000 cfu (65 ul)) was added to each 1 g sample, mixed, and incubated at room temperature. Following incubation, samples were diluted 1:10 with water and plated on a BG plate.

Two diets were studied, as shown in Table 29. Results are reported in Table 30.

TABLE 29

| ingredients | % of total |
|---|---|
| Diet 1 (swine diet) | |
| corn | 51.60 |
| SBM, 48 | 30 |
| DairyLac 80 | 8.50 |
| Menhaden fish meal (Select) | 3.98 |
| Choice white grease | 3.00 |
| Dicalcium Phosphate | 1.24 |
| Limestone | 0.34 |
| Lysine | 0.26 |
| DL-Methionine | 0.13 |
| Threonine | 0.16 |
| Vitamins, TMs, Salt and Mecadox | 0.93 |
| Corn Starch | to 100 |
| Diet 2 (broiler diet) | |
| corn | 60.551 |
| SBM | 32.254 |
| Fat, animal | 3.665 |
| Dicalcium Phosphate | 1.861 |
| Limestone | 0.811 |
| Vitamin/Mineral premix | 0.350 |
| Salt | 0.340 |
| L-lysine HCl 78% | 0.097 |
| Threonine | 0.051 |
| Satoquin-mix6 | 0.019 |
| Copper Sulfate | 0.003 |
| DL-methionine | 0.2 |

TABLE 30

Blend tested: A71

| | 1 hour | | 24 hours | | 48 hours | | final |
|---|---|---|---|---|---|---|---|
| g/kg | cfu/g | log | cfu/g | log | cfu/g | log | pH |
| Diet 1 | | | | | | | |
| control | 27,700 | 4.4 | 6,432 | 3.8 | 2,530 | 3.4 | 5.83 |
| 2 | 4,320 | 3.6 | 80 | 1.9 | 40 | 1.6 | 5.52 |
| 5 | 3,840 | 3.6 | 40 | 1.6 | 0 | — | 5.21 |
| 7.5 | 3,080 | 3.5 | 80 | 1.9 | 0 | — | 5.01 |
| 10 | 1,560 | 3.2 | 0 | — | 0 | — | 4.87 |
| Diet 2 | | | | | | | |
| control | 25,000 | 4.4 | 6,160 | 3.8 | 2,570 | 3.4 | 6.06 |
| 2 | 8,080 | 3.9 | 40 | 1.6 | 40 | 1.6 | 5.67 |
| 5 | 7,000 | 3.8 | 40 | 1.6 | 40 | 1.6 | 5.31 |

TABLE 30-continued

| | Blend tested: A71 | | | | | | |
|---|---|---|---|---|---|---|---|
| | 1 hour | | 24 hours | | 48 hours | | final |
| g/kg | cfu/g | log | cfu/g | log | cfu/g | log | pH |
| 7.5 | 4,400 | 3.6 | 40 | 1.6 | 0 | — | 5.1 |
| 10 | 900 | 3.0 | 0 | — | 0 | — | 4.82 |

EXAMPLE 20

Following the protocol of Example 19, the effects of blend A69 at neutral pH were tested. Formic acid (85%) was obtained from BASF Corporation (Mt. Olive, N.J.), product # 019723, lot # 87656216KO. Two diets were studied, as shown in Table 31. Results are reported in Table 32.

TABLE 31

| ingredients | % of total |
|---|---|
| Diet 3 | |
| soybean meal | 33.40 |
| corn | 32.85 |
| wheat hard red | 20.00 |
| organic peas meal | 5.00 |
| fat, animal | 4.80 |
| dicalcium phophate | 1.81 |
| limestone | 0.98 |
| salt | 0.43 |
| Vitamin/Mineral premix | 0.35 |
| Threonine | 0.10 |
| Avizyme1502 | 0.10 |
| Santoquin-mix6 | 0.02 |
| Coban 60 | 0.05 |
| copper sulfate | 0.00 |
| Diet 4 | |
| corn | 60.50 |
| soybean meal | 28.46 |
| limestone | 7.76 |
| Dicalcium Phosphate | 1.63 |
| animal fat | 1.00 |
| Vitamin/Mineral premix | 0.35 |
| salt | 0.26 |
| Santoquin-mix6 | 0.02 |
| copper sulfate | 0.00 |
| choline Cl-60% | 0.00 |

TABLE 32

| | blend tested: A69 | | | | | | |
|---|---|---|---|---|---|---|---|
| | 1 hour | | 24 hours | | 48 hours | | final |
| g/kg | cfu/g | log | cfu/g | log | cfu/g | log | pH |
| Diet 3 | | | | | | | |
| control | 68,000 | 4.8 | 2,470 | 3.4 | 880 | 2.9 | 6.05 |
| 2 | 5,600 | 3.7 | 120 | 2.1 | 40 | 1.6 | 5.67 |
| 5 | 8,900 | 3.9 | 40 | 1.6 | 40 | 1.6 | 5.46 |
| 7.5 | 4,600 | 3.7 | 40 | 1.6 | 80 | 1.9 | 5.28 |
| 10 | 10,600 | 4.0 | 40 | 1.6 | 0 | — | 5.13 |
| Diet 4 | | | | | | | |
| control | 68,000 | 4.8 | 2,630 | 3.4 | 1,380 | 3.1 | 5.99 |
| 2 | 8,600 | 3.9 | 0 | — | 0 | — | 5.8 |
| 5 | 900 | 3.0 | 40 | 1.6 | 0 | — | 5.55 |
| 7.5 | 2,600 | 3.4 | 200 | 2.3 | 0 | — | 5.37 |
| 10 | 2,700 | 3.4 | 0 | — | 40 | 1.6 | 5.12 |

EXAMPLE 21

Following the protocol of Example 9, the effects of blends of Alimet®, lactic acid, formic acid, and/or butyric acid were studied. Blend formulations are set forth in Table 33. Up to five replicates were performed, and results are reported in Tables 34 and 35.

TABLE 33

| | acid formulations (g/kg) | | | |
|---|---|---|---|---|
| Blend | A[1] | L[2] | F[3] | B[4] |
| A147 | 0 | 0 | 0 | 10 |
| A148 | 2 | 0 | 0 | 8 |
| A149 | 7.5 | 0 | 0 | 2.5 |
| A150 | 3.3 | 0 | 0 | 6.7 |
| A151 | 2 | 2.67 | 0 | 5.33 |
| A152 | 7.5 | 0.8 | 0 | 1.67 |
| A153 | 0 | 0 | 3.3 | 6.7 |
| A154 | 2 | 0 | 2.67 | 5.3 |
| A155 | 7.5 | 0 | 0.8 | 1.67 |
| A156 | 0 | 6.7 | 0 | 3.3 |
| A157 | 2 | 5.3 | 0 | 2.67 |
| A158 | 7.5 | 1.67 | 0 | 0.8 |
| A159 | 0 | 3.3 | 3.3 | 3.3 |
| A160 | 2 | 2.67 | 2.67 | 2.67 |
| A161 | 7.5 | 0.8 | 0.8 | 0.8 |
| A162 | 0 | 0 | 6.7 | 3.3 |
| A163 | 2 | 0 | 5.3 | 2.67 |
| A164 | 7.5 | 0 | 1.67 | 0.8 |
| A165 | 0 | 10 | 0 | 0 |
| A166 | 2 | 8 | 0 | 0 |
| A167 | 7.5 | 2.5 | 0 | 0 |
| A168 | 0 | 6.7 | 3.3 | 0 |
| A169 | 2 | 5.3 | 2.67 | 0 |
| A170 | 7.5 | 1.67 | 0.8 | 0 |
| A171 | 0 | 3.3 | 6.7 | 0 |
| A172 | 2 | 2.67 | 5.3 | 0 |
| A173 | 7.5 | 0.8 | 1.67 | 0 |
| A174 | 0 | 0 | 10 | 0 |
| A175 | 2 | 0 | 8 | 0 |
| A176 | 7.5 | 0 | 2.5 | 0 |

[1]Alimet®
[2]Lactic acid
[3]Formic acid
[4]Butyric acid

TABLE 34

| | | | | Trial: | | | |
|---|---|---|---|---|---|---|---|
| | Average | | | 1 | 2 | 3 | 4 |
| Blend | cfu/g | log | Δ log | cfu/g | cfu/g | cfu/g | cfu/g |
| control | 49,200 | 4.7 | — | 58,200 | 43,400 | 46,000 | N/A |
| A147 | 18,800 | 4.3 | 0.4 | 22,200 | 15,400 | N/A | N/A |
| A148 | 15,700 | 4.2 | 0.5 | 19,800 | 11,600 | N/A | N/A |
| A149 | 70 | 1.8 | 2.8 | 80 | 200 | 0 | 0 |
| A150 | 12,300 | 4.1 | 0.6 | 1,200 | 23,400 | N/A | N/A |
| A151 | 6,000 | 3.8 | 0.9 | 8,200 | 3,800 | N/A | N/A |
| A152 | 60 | 1.8 | 2.9 | 40 | 40 | 120 | 40 |
| A153 | 1,600 | 3.2 | 1.5 | 3,200 | 0 | N/A | N/A |
| A154 | 20 | 1.3 | 3.4 | 40 | 40 | 0 | 0 |
| A155 | 10 | 1.0 | 3.7 | 40 | 0 | 0 | 0 |
| A156 | 11,300 | 4.1 | 0.6 | 6,000 | 16,600 | N/A | N/A |
| A157 | 2,900 | 3.5 | 1.2 | 1,000 | 4,800 | N/A | N/A |
| A158 | 400 | 2.6 | 2.1 | 800 | 0 | N/A | N/A |
| A159 | 0 | — | 4.7 | 0 | 0 | 0 | 0 |
| A160 | 0 | — | 4.7 | 0 | 0 | 0 | 0 |
| A161 | 20 | 1.3 | 3.4 | 40 | 40 | 0 | 0 |
| control | 63,133 | 4.8 | — | 56,800 | 64,000 | 68,600 | N/A |

N/A = replicate not performed

TABLE 35

| Blend | Average cfu/g | log | Δ log | Trial: 1 cfu/g | 2 cfu/g | 3 cfu/g | 4 cfu/g |
|---|---|---|---|---|---|---|---|
| control | 25,666 | 4.4 | — | 23,200 | 25,800 | 28,000 | N/A |
| A162 | 0 | — | 4.4 | 0 | 0 | 0 | 0 |
| A163 | 0 | — | 4.4 | 0 | 0 | 0 | 0 |
| A164 | 0 | — | 4.4 | 0 | 0 | 0 | 0 |
| A165 | 5,100 | 3.7 | 0.7 | 4,000 | 6,200 | N/A | N/A |
| A166 | 150 | 2.2 | 2.2 | 120 | 120 | 120 | 240 |
| A167 | 30 | 1.5 | 2.9 | 40 | 80 | 0 | 0 |
| A168 | 0 | — | 4.4 | 0 | 0 | 0 | 0 |
| A169 | 0 | — | 4.4 | 0 | 0 | 0 | 0 |
| A170 | 0 | — | 4.4 | 0 | 0 | 0 | 0 |
| A171 | 0 | — | 4.4 | 0 | 0 | 0 | 0 |
| A172 | 0 | — | 4.4 | 0 | 0 | 0 | 0 |
| A173 | 0 | — | 4.4 | 0 | 0 | 0 | 0 |
| A174 | 0 | — | 4.4 | 0 | 0 | 0 | 0 |
| A175 | 0 | — | 4.4 | 0 | 0 | 0 | 0 |
| A176 | 0 | — | 4.4 | 0 | 0 | 0 | 0 |
| control | 20000 | 4.3 | — | 20200 | 19800 | N/A | N/A |

N/A = replicate not performed

EXAMPLE 22

Following the protocol of Example 9, the effects of blends of Alimet®, lactic acid, propionic acid (99%, obtained from Sigma Chemical Co., St. Louis, Mo., lot P-1386), and/or butyric acid were studied. Blend formulations are set forth in Table 36. Up to five replicates were performed, and results are reported in Tables 37 and 38.

TABLE 36

| Blend | acid formulations (g/kg) | | | |
|---|---|---|---|---|
|  | A[1] | L[2] | P[3] | B[4] |
| A177 | 0 | 0 | 0 | 10 |
| A178 | 2 | 0 | 0 | 8 |
| A179 | 7.5 | 0 | 0 | 2.5 |
| A180 | 0 | 3.3 | 0 | 6.7 |
| A181 | 2 | 2.67 | 0 | 5.3 |
| A182 | 7.5 | 0.8 | 0 | 1.67 |
| A183 | 0 | 0 | 3.3 | 6.7 |
| A184 | 2 | 0 | 2.67 | 5.3 |
| A185 | 7.5 | 0 | 0.8 | 1.67 |
| A186 | 0 | 6.7 | 0 | 3.3 |
| A187 | 2 | 5.3 | 0 | 2.67 |
| A188 | 7.5 | 1.67 | 0 | 0.8 |
| A189 | 0 | 3.3 | 3.3 | 3.3 |
| A190 | 2 | 2.67 | 2.67 | 2.67 |
| A191 | 7.5 | 0.8 | 0.8 | 0.8 |
| A192 | 0 | 0 | 6.7 | 3.3 |
| A193 | 2 | 0 | 5.3 | 2.67 |
| A194 | 7.5 | 0 | 1.67 | 0.8 |
| A195 | 0 | 10 | 0 | 0 |
| A196 | 2 | 8 | 0 | 0 |
| A197 | 7.5 | 2.5 | 0 | 0 |
| A198 | 0 | 6.7 | 3.3 | 0 |
| A199 | 2 | 5.3 | 2.67 | 0 |
| A200 | 7.5 | 1.67 | 0.8 | 0 |
| A201 | 0 | 3.3 | 6.7 | 0 |
| A202 | 2 | 2.67 | 5.3 | 0 |
| A203 | 7.5 | 0.8 | 1.67 | 0 |
| A204 | 0 | 0 | 10 | 0 |
| A205 | 2 | 0 | 8 | 0 |
| A206 | 7.5 | 0 | 2.5 | 0 |
| A207 | 10 | 0 | 0 | 0 |

[1] Alimet®
[2] Lactic acid
[3] Propionic acid
[4] Butyric acid

TABLE 37

| Blend | Average cfu/g | log | Δ log | Trial: 1 cfu/g | 2 cfu/g | 3 cfu/g |
|---|---|---|---|---|---|---|
| control | 20,067 | 4.3 | — | 17,200 | 18,800 | 24,200 |
| A177 | 6,333 | 3.8 | 0.5 | 5,400 | 7,000 | 6,600 |
| A178 | 500 | 2.7 | 1.6 | 400 | 600 | N/A |
| A179 | 400 | 2.6 | 1.7 | 200 | 600 | N/A |
| A180 | 1,400 | 3.1 | 1.2 | 1,400 | 1,400 | N/A |
| A181 | 1,500 | 3.2 | 1.1 | 2,000 | 1,000 | N/A |
| A182 | 100 | 2.0 | 2.3 | 200 | 0 | N/A |
| A183 | 6,000 | 3.8 | 0.5 | 9,600 | 2,400 | N/A |
| A184 | 6,900 | 3.8 | 0.5 | 8,800 | 5,000 | N/A |
| A185 | 1,300 | 3.1 | 1.2 | 1,400 | 1,200 | N/A |
| A186 | 4,100 | 3.6 | 0.7 | 5,400 | 2,800 | N/A |
| A187 | 2,400 | 3.4 | 0.9 | 600 | 4,200 | N/A |
| A188 | 400 | 2.6 | 1.7 | 200 | 600 | N/A |
| A189 | 4,700 | 3.7 | 0.6 | 1,000 | 8,400 | N/A |
| A190 | 7,300 | 3.9 | 0.4 | 7,800 | 6,800 | N/A |
| A191 | 300 | 2.5 | 1.8 | 600 | 0 | N/A |
| control | 18,733 | 4.3 | — | 20,000 | 22,800 | 13400 |

N/A = replicate not performed

TABLE 38

| Blend | Average cfu/g | log | Δ log | Trial: 1 cfu/g | 2 cfu/g | 3 cfu/g | 4 cfu/g |
|---|---|---|---|---|---|---|---|
| control | 7,800 | 3.9 | — | 9,800 | 7,200 | 6,400 | N/A |
| A192 | 6,100 | 3.8 | 0.4 | 6,600 | 5,600 | N/A | N/A |
| A193 | 2,600 | 3.4 | 0.8 | 2,200 | 3,000 | N/A | N/A |
| A194 | 25 | 1.4 | 2.8 | 50 | 50 | 0 | 0 |
| A195 | 400 | 2.6 | 1.6 | 800 | 0 | N/A | N/A |
| A196 | 300 | 2.5 | 1.7 | 200 | 400 | N/A | N/A |
| A197 | 0 | — | 4.2 | 0 | 0 | 0 | 0 |
| A198 | 2,400 | 3.4 | 0.8 | 1,000 | 3,800 | N/A | N/A |
| A199 | 600 | 2.8 | 1.4 | 0 | 1,200 | N/A | N/A |
| A200 | 0 | — | 4.2 | 0 | 0 | 0 | 0 |
| A201 | 3,800 | 3.6 | 0.6 | 3,200 | 4,400 | N/A | N/A |
| A202 | 900 | 3.0 | 1.2 | 1,000 | 800 | N/A | N/A |
| A203 | 0 | — | 4.2 | 0 | 0 | 0 | 0 |
| A204 | 3,500 | 3.5 | 0.6 | 5,400 | 1,600 | N/A | N/A |
| A205 | 100 | 2.0 | 2.2 | 200 | 0 | N/A | N/A |
| A206 | 0 | — | 4.2 | 0 | 0 | 0 | 0 |
| A207 | 0 | — | 4.2 | 0 | 0 | 0 | 0 |
| control | 30,600 | 4.5 | — | 41,600 | 19,400 | 30,800 | N/A |

N/A = replicate not performed

EXAMPLE 23

The ability of Alimet® and DLM to function as palatants for dog and cat food was studied. Alimet® and DLM were added into premium-type dog and cat food in the mixer to test the acceptance of the food compared to food lacking either supplement. The food used comprised good quality protein, and was high in CP and fat. A premium palantant was also added to the food. Alimet® or DLM was added into the mixer prior to extrusion. The formulation of the feline diet is described in Table 39, and of the canine diet in Table 40. The Alimet®/DLM supplementation levels, and intake ratios, are described in Table 41. The intake ratio describes the relative incidence of selecting one food over another.

For the canine study, twenty-one dogs were used (seven small, seven medium, and seven large dogs). For the feline study, twenty mature cats were used. The animals were given two choices of food, placed in separate bowls. Over a two-day period, the dogs were given access to the food for 30 minutes; cats had access for 22 hours. The food chosen and consumed first was observed.

TABLE 39

Feline Diet

| Ingredient | % of total diet |
|---|---|
| Corn | 14.7 |
| Poultry byproduct (low ash) | 20 |
| Soybean Meal | 12.5 |
| Corn gluten meal | 12.2 |
| Meat and Bone meal | 4 |
| Animal fat | 11.4 |
| Rice brewer's | 19.4 |
| Flavor | 2 |
| Fish meal | 2 |
| Dried eggs | 0.5 |
| Salt | 0.5 |
| KCl | 0.5 |
| Vitamins | 0.2 |
| Choline | 0.1 |
| Taurine | 0.1 |
| Tocopherol | 0.05 |
| Trace Minerals | 0.05 |

TABLE 40

Canine Diet

| Ingredient | % of total diet |
|---|---|
| Corn | 33.0 |
| Barley | 15.0 |
| Poultry byproduct (low ash) | 13.0 |
| Poultry byproduct | 12.0 |
| Soybean Meal | 9.0 |
| Animal fat | 8.0 |
| Rice brewer's | 5.0 |
| Flavor | 2.0 |
| Dried eggs | 1.0 |
| Salt | 0.5 |
| Limestone | 0.36 |
| Vitamins | 0.2 |
| Choline | 0.1 |
| Tocopherol | 0.05 |
| Trace Minerals | 0.05 |

TABLE 41

| Foods compared | Intake Ratio |
|---|---|
| Canine | |
| 0.05% Alimet vs. control | 2.07:1 |
| 0.10% Alimet vs. control | 5.58:1 |
| 0.15% Alimet control | 5.13:1 |
| 0.10% DLM vs. control | 5.32:1 |
| 0.15% DLM vs. control | 4.95:1 |
| 0.10% Alimet vs. 0.05% Alimet | 2.54:1 |
| 0.15% Alimet vs. 0.05% Alimet | 1.99:1 |
| 0.15% Alimet vs. 0.10% Alimet | 2.54:1 |
| 0.15% DLM vs. 0.10% DLM | 1.57:1 |
| 0.10% DLM vs. 0.10% Alimet | 1.05:1 |
| 0.15% DLM vs. 0.15% Alimet | 2.5:1 |
| Feline | |
| 0.20% Alimet ® vs. control | 1.67:1 |
| 0.25% Alimet ® vs. control | 1.91:1 |
| 0.30% Alimet ® vs. control | 1.85:1 |
| 0.25% DLM vs. control | 1.87:1 |
| 0.30% DLM vs. control | 1.63:1 |
| 0.25% Alimet ® vs. 0.20% Alimet ® | 1.30:1 |
| 0.30% Alimet ® vs. 0.20% Alimet ® | 1.26:1 |

TABLE 41-continued

| Foods compared | Intake Ratio |
|---|---|
| 0.30% Alimet ® vs. 0.25% Alimet ® | 1.16:1 |
| 0.30% DLM vs. 0.25% DLM | 1.04:1 |
| 0.25% DLM vs. 0.25% Alimet ® | 1.24:1 |
| 0.30% DLM vs. 0.30% Alimet ® | 1.47:1 |

EXAMPLE 24

Acceptance of food containing Alimet® or DLM was studied to evaluate dietary consumption under no-choice conditions. Food was offered to the animals (18 dogs: 6 small, 6 medium, 6 large; 15 cats) for one week. The urine pH of six of the cats was also monitored.

The diets described in Tables 39 and 40 above were used. Diets were supplemented with Alimet® or DLM (0.1% for the canine study, 0.25% for the feline study). Additional urine pH tests were carried out with 0.3% Alimet®.

Results of the urine pH experiments are given in Tables 42 and 43. Results of the acceptance text are given in Table 44.

TABLE 42

| | Urine pH | | |
|---|---|---|---|
| Cat No. | Control | Alimet 0.25% | DL Met 0.25% |
| 452 | 6.35 | 6.45 | 6.39 |
| 453 | 6.44 | 6.2 | 6.38 |
| 457 | 6.29 | 6.56 | 6.39 |
| 460 | 6.25 | 6.03 | 6.36 |
| 465 | 6.22 | 6 | 6.1 |
| 475 | 6.56 | 6.44 | 6.36 |

TABLE 43

| | Urine pH | |
|---|---|---|
| Cat No. | Control | Alimet ® 0.3% |
| 450 | 6.20 | 6.03 |
| 453 | 6.44 | 6.10 |
| 465 | 6.04 | 5.53 |
| 468 | 6.40 | 5.73 |
| 469 | 6.68 | 6.31 |

TABLE 44

| | | Total grams consumed | |
|---|---|---|---|
| Supplementation level | | control | supplemented food |
| Canine | | | |
| Alimet ® | 0.05% | 5,046 | 10,420 |
| | 0.1% | 2,101 | 11,714 |
| | 0.15% | 2,419 | 12,978 |
| DLM | 0.1% | 2,114 | 11,244 |
| | 0.15% | 2,734 | 13,542 |
| Feline | | | |
| Alimet ® | 0.2% | 1,111 | 1,853 |
| | 0.25% | 955 | 1,827 |
| | 0.3% | 1,003 | 1,858 |
| DLM | 0.25% | 985 | 1,842 |
| | 0.3% | 1,078 | 1,754 |

EXAMPLE 25

Common carp, *Cyprinus carpio L.* from a commercial fish farm were acquired and sorted to common body weight and length, about 20 g and 8-11 cm, respectively. A control, fish-meal free, diet to assess basic feeding behavior consisted of 30% wheat flour and 70% of a typical vegetable based basal diet, Table 1. The tested diets were the Control diet and the HMBA provided at 0.07% Alimet, 0.14% Alimet, 0.28% Alimet, 0.077% methionine hydroxy analog (MHA), 0.154% MHA or 0.308% MHA added to the basic control diet.

TABLE

Composition of Basal Diet:

| Ingredient | Percent |
| --- | --- |
| Wheat Middling and Reddog | 30.25 |
| Rapeseed Meal | 15.50 |
| Soybean Meal | 50.50 |
| Oil | 2.15 |
| Vitamins | 0.20 |
| Mineral Premix | 0.30 |

Diets were mixed with adequate water to create a stable feed ball. The feed balls were of such a consistency that they did not disintegrate when bitten by the fish. Twenty tanks (45 cm×40 cm×45 cm) were dedicated the feeding behavior assessment. Two fish were housed in each tank with two feeding bars per tank. The control diet was placed on both bars during a pre-trial training period, with the control diet being made available for 10 minutes twice daily. The water in each tank was aerated 24 h a day and the fish were fed the control diet under the above conditions for one week prior to the study.

To evaluate preference, the control and test diets were each placed on one of the two bars in each tank. A mechanical sensor was affixed to each bar to electronically record the number of bites per feed type during the 10 minutes the fish were offered feed.

The number of bites on feeds formulated with either liquid HMTBA (Alimet) or dry HMTBA (MHA) were significantly higher than that of the control diet as detailed in the following table.

TABLE

Relative feeding rate of tested common carp

| | % Inclusion | Bites/10 minutes | T test | Preference |
| --- | --- | --- | --- | --- |
| Alimet Test | | | | |
| Alimet | 0.07 | 77.44 ± 10.46 | P < 0.01 | 2.69:1 |
| Control | | 28.75 ± 10.46 | | |
| Alimet | 0.14 | 75.17 ± 14.10 | P < 0.01 | 3.02:1 |
| Control | | 24.83 ± 14.10 | | |
| Alimet | 0.28 | 70.83 ± 13.17 | P < 0.01 | 2.43:1 |
| Control | | 29.17 ± 13.17 | | |
| MHA Test | | | | |
| MHA | 0.077 | 74.39 ± 14.14 | P < 0.01 | 2.90:1 |
| Control | | 25.61 ± 14.14 | | |
| MHA | 0.154 | 67.73 ± 23.18 | P < 0.05 | 2.07:1 |
| Control | | 32.73 ± 23.18 | | |
| MHA | 0.308 | 63.52 ± 20.23 | P < 0.05 | 1.74:1 |
| Control | | 36.48 ± 20.23 | | |

In view of the above, it will be seen that the several objects of the invention are achieved and other advantageous results attained.

As various changes could be made in the above feed rations and methods without departing from the scope of the invention, it is intended that all matter contained in the above description and shown in the accompanying drawing shall be interpreted as illustrative and not in a limiting sense.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

Unless otherwise specified, amounts expressed as percentages are in percent by weight.

What is claimed is:

1. A method for enhancing the palatability of feed for aquaculture, the method comprising treating the feed with a compound of formula I:

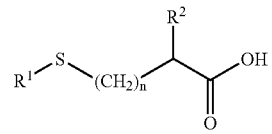

wherein $R^1$ is an alkyl group having from one to four carbon atoms;

n is an integer from 0 to 2;

$R^2$ is selected from the group consisting of hydroxy, —$OCOR^3$, or —$NHCOR^3$;

and wherein $R^3$ is an organic acid derivative;

or a salt thereof;

wherein the concentration of the compound of formula I in the feed is from about 0.005 wt. % to about 0.5 wt. %; wherein the contacts of said aquaculture with said aquaculture food during a unit time are increased relative to the contacts of the same aquaculture with an aquaculture food otherwise identical but lacking said compound of formula I.

2. The method of claim 1 wherein said compound of Formula I is 2-hydroxy-4-(methylthio)butanoic acid, or a salt, ester or amide thereof.

3. The method of claim 1 wherein said concentration of the compound of formula I is from about 0.01 wt. % to about 0.04 wt. %.

4. The method of claim 1 wherein said feed for aquaculture is fed to fish comprising fish other than catfish and salmon.

5. The method of claim 4 wherein said feed for aquaculture is fed to carp.

6. A method of feeding fish comprising administering a fish food comprising a compound of formula I:

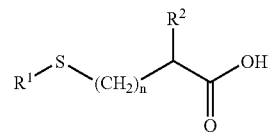

wherein $R^1$ is an alkyl group having from one to four carbon atoms;

n is an integer from 0 to 2;

$R^2$ is selected from the group consisting of hydroxy, —$OCOR^3$, or —$NHCOR^3$;

and wherein $R^3$ is an organic acid derivative;

or a salt thereof;

wherein the concentration of said compound of formula I is effective to enhance the palatability of said fish food; such that the contacts of said fish with said fish food during a unit time are increased relative to the contacts of the same fish with a fish food otherwise identical but lacking said compound of formula I.

7. The method of claim 6 wherein said compound of Formula I is 2-hydroxy-4-(methylthio)butanoic acid, or a salt, ester or amide thereof.

8. The method of claim 6 wherein the concentration of the compound of formula I is from about 0.001 wt. % to about 1.0 wt. %.

9. The method of claim 8 wherein the concentration of the compound of formula I is from about 0.01 wt. % to about 0.07 wt. %.

10. The method of claim 6 wherein said fish food is fed to carp, catfish, tilapia, salmon, trout, smelt, shrimp or prawns.

11. The method of claim 10 wherein said fish food is fed to carp.

* * * * *